(12) United States Patent
Bischof et al.

(10) Patent No.: US 10,414,699 B2
(45) Date of Patent: *Sep. 17, 2019

(54) PROCESS IMPROVEMENTS IN SELECTIVE ETHYLENE OLIGOMERIZATIONS

(71) Applicant: Chevron Phillips Chemical Company LP, The Woodlands, TX (US)

(72) Inventors: Steven M. Bischof, Humble, TX (US); Orson L. Sydora, Houston, TX (US); Jared T. Fern, Kingwood, TX (US); Uriah J. Kilgore, Kingwood, TX (US); Steven Ross Hutchison, Spring, TX (US); Ray Rios, Cypress, TX (US); Eric R. Fernandez, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/166,991

(22) Filed: May 27, 2016

(65) Prior Publication Data

US 2017/0342000 A1    Nov. 30, 2017

(51) Int. Cl.
*C07C 2/36* (2006.01)
*B01J 31/24* (2006.01)
(Continued)

(52) U.S. Cl.
CPC ............. *C07C 2/36* (2013.01); *B01J 31/24* (2013.01); *C07F 9/46* (2013.01); *C07F 9/6561* (2013.01);
(Continued)

(58) Field of Classification Search
None
See application file for complete search history.

(56) References Cited

U.S. PATENT DOCUMENTS 3,361,525 A    1/1968    De Rycke et al.
5,217,703 A    6/1993    Goodson
(Continued)

FOREIGN PATENT DOCUMENTS

CN    1490291 A    4/2004
DE    1146892 B    4/1963
(Continued)

OTHER PUBLICATIONS

Agapie, Theodor, et al., "Mechanistic Studies of Olefin and Alkyne Trimerization with Chromium Catalysts: Deuterium Labeling and Studies of Regiochemistry Using a Model Chromacyclopentane Complex," J. Am. Chem. Soc., 2007, pp. 14281-14295, vol. 129, No. 46, American Chemical Society.
(Continued)

*Primary Examiner* — In Suk C Bullock
*Assistant Examiner* — Ali Z Fadhel
(74) *Attorney, Agent, or Firm* — Conley Rose, P.C.

(57) ABSTRACT

Disclosed are processes, systems, and reaction systems for the oligomerization of ethylene to form an oligomer product in a reaction zone using a catalyst system having i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane. Ethylene can be contacted with an organic reaction medium to form an ethylene feedstock mixture prior to contact with the catalyst system. The ethylene feedstock mixture can be contacted with the catalyst system inside or outside of the reaction zone.

17 Claims, 5 Drawing Sheets

(51) Int. Cl.

| | | |
|---|---|---|
| C07F 9/46 | (2006.01) | |
| C07F 9/6561 | (2006.01) | |
| C07F 11/00 | (2006.01) | |
| C08F 4/69 | (2006.01) | |

(52) U.S. Cl.
CPC ........ *C07F 11/005* (2013.01); *C08F 4/69068* (2013.01); *C07C 2531/24* (2013.01)

(56) References Cited

U.S. PATENT DOCUMENTS

| | | | |
|---|---|---|---|
| 7,276,566 | B2 | 10/2007 | Muruganandam et al. |
| 7,300,904 | B2 | 11/2007 | Dixon et al. |
| 7,361,623 | B2 | 4/2008 | Dixon et al. |
| 7,554,001 | B2 | 6/2009 | Dixon et al. |
| 7,994,363 | B2 | 8/2011 | Gao et al. |
| 8,252,956 | B2 | 8/2012 | Gao et al. |
| 8,367,786 | B2 | 2/2013 | Dixon et al. |
| 8,680,003 | B2 | 3/2014 | Sydora et al. |
| 8,865,610 | B2 | 10/2014 | Sydora et al. |
| 9,283,555 | B2 | 3/2016 | Sydora et al. |
| 9,732,106 | B2 | 8/2017 | Sydora et al. |
| 2002/0182124 | A1 | 12/2002 | Woodard et al. |
| 2006/0247399 | A1 | 11/2006 | McConville et al. |
| 2007/0185360 | A1 | 8/2007 | Buchanan et al. |
| 2008/0207973 | A1 | 8/2008 | Palmas et al. |
| 2010/0041841 | A1 | 2/2010 | Terry et al. |
| 2010/0222622 | A1* | 9/2010 | Overett ............. C07C 2/32 585/523 |
| 2010/0240847 | A1 | 9/2010 | Dixon et al. |
| 2010/0274065 | A1 | 10/2010 | Sydora |
| 2012/0142989 | A1* | 6/2012 | Jaber ............. C07C 2/36 585/532 |
| 2012/0309965 | A1 | 12/2012 | Sydora et al. |
| 2013/0090508 | A1* | 4/2013 | Wang ............. C07C 2/32 585/508 |
| 2013/0331629 | A1* | 12/2013 | Sydora ............. B01J 31/189 585/523 |
| 2016/0375431 | A1 | 12/2016 | Carney et al. |
| 2017/0349505 | A1 | 12/2017 | Kilgore et al. |

FOREIGN PATENT DOCUMENTS

| | | |
|---|---|---|
| EP | 0780353 A1 | 6/1997 |
| EP | 2684857 A1 | 1/2014 |
| WO | 0204119 A1 | 1/2002 |
| WO | 2004056477 A1 | 7/2004 |
| WO | 2004056478 A1 | 7/2004 |
| WO | 2004056479 A1 | 7/2004 |
| WO | 2004056480 A1 | 7/2004 |
| WO | 2005039758 A1 | 5/2005 |
| WO | 2005123633 A1 | 12/2005 |
| WO | 2005123884 A2 | 12/2005 |
| WO | 2007007272 A2 | 1/2007 |
| WO | 2007088329 A1 | 8/2007 |
| WO | 2008014139 A2 | 1/2008 |
| WO | 2008119153 A1 | 10/2008 |
| WO | 2010034101 A1 | 4/2010 |
| WO | 2010034102 A1 | 4/2010 |
| WO | 2010051415 A1 | 5/2010 |
| WO | 2011130822 A1 | 10/2011 |
| WO | 2011137027 A1 | 11/2011 |
| WO | 2011140629 A1 | 11/2011 |
| WO | 2012051698 A1 | 4/2012 |
| WO | 2012071644 A1 | 6/2012 |
| WO | 2012092415 A1 | 7/2012 |
| WO | 2012142693 A1 | 10/2012 |
| WO | 2013168106 A1 | 11/2013 |
| WO | 2015094207 A1 | 6/2015 |
| WO | 2015097599 A1 | 7/2015 |
| WO | 2017010998 A1 | 1/2017 |
| WO | 2017011127 A1 | 1/2017 |

OTHER PUBLICATIONS

Bollmann, Annette, et al., "Ethylene Tetramerization: A New Route to Produce 1-Octene in Exceptionally High Selectivities," J. Am. Chem. Soc., 2004, pp. 14712-14713, vol. 126, No. 45, American Chemical Society.
Carter, Anthea, et al., "High activity ethylene trimerisation catalysts based on diphospine ligands," Chemical Communications, vol. 8, 2002, pp. 858-859 plus 2 pages Supplementary Information.
Filing receipt and specification for International application entitled "Olefin Compositions," filed Jul. 14, 2015 as International application No. PCT/US2015/040433.
Filing receipt and specification for patent application entitled, "Reduced Polymer Formation for Selective Ethylene Oligomerizations," by Jared T. Fern, et al., filed May 27, 2016 as U.S. Appl. No. 15/167,009.
Filing receipt and specification for patent application entitled "Process Improvements for Chromium Based Ethylene Oligomerizations," by Steven M. Bischof, et al., filed May 27, 2016 as U.S. Appl. No. 15/167,017.
Filing receipt and specification for patent application entitled "Reduced Polymer Formation for Selective Ethylene Oligomerizations," by Jared T. Fern, et al., filed May 27, 2016 as U.S. Appl. No. 15/617,024.
Group notation revised in periodic table, Feb. 4, 1985, C&EN, pp. 26-27.
McNaught, Alan D., et al., "Compendium of Chemical Terminology," IUPAC Recommendations, Second edition, 1997, 5 pages, Wiley-Blackwell.
Sydora, Orson L., et al., "Selective Ethylene Tri-/Tetramerization Catalysts," ACS Catalysis, 2012, pp. 2452-2455, vol. 2, American Chemical Society.
Filing receipt and specification for patent application entitled "Fouling Protection for an Oligomerization Reactor Inlet," by Steven M. Bischof, et al., filed Jun. 6, 2017 as U.S. Appl. No. 15/615,113.
Office Action dated Jul. 24, 2017 (33 pages), U.S. Appl. No. 15/167,009, filed May 27, 2016.
Foreign communication from a related counterpart application—International Search Report and Written Opinion, PCT/US2017/032199, dated Aug. 17, 2017, 14 pages.
Office Action dated Aug. 2, 2017 (36 pages), U.S. Appl. No. 15/167,024, filed May 27, 2016.
Foreign communication from a related counterpart application—International Search Report and Written Opinion, PCT/US2017/032191, dated Aug. 14, 2017, 15 pages.
Kuhlmann, S,. et al,. "Chromium catalyzed tetramerization of ethylene in a continuous tube reactor—Proof of concept and kinetic aspects," Journal of Catalysis, 2009, pp. 83-91, vol. 262, No. 1, Elsevier Inc.
Office Action dated Aug. 30, 2017 (28 pages), U.S. Appl. No. 15/167,017, filed May 27, 2017.
Foreign communication from a related counterpart application—International Search Report and Written Opinion, PCT/US2017/033165, dated Aug. 3, 2017, 11 pages.
Foreign communication from a related counterpart application—International Search Report and Written Opinion, PCT/US2017/033168, dated Aug. 3, 2017, 8 pages.
AkzoNobel Product Data Sheet MMAO-3A/Heptane Solutions, 2014, 2 pgs.
AkzoNobel Safety Data Sheet MMAO-3A 7 wt% Al in Heptane, 2016, 17 pgs.
AkzoNobel Product Data Sheet MMAO-20/Heptane Solutions, 2014, 2 pgs.
AkzoNobel Safety Data Sheet MMAO-20 11-30% in Heptane, 2007, 9 pgs.
Filing receipt and specification for patent application entitled "Oligomerization Reactions Using Aluminoxanes," by Steven M. Bischof, et al., filed Sep. 28, 2017, 2017 as U.S. Appl. No. 15/719,107.
"Kappler, B., et al., "Real-time Monitoring of Ethene/1-hexene Copolymerizations: Determination of Catalyst Activity, Copolymer Composition and Copolymerization Parameters," Polymer, 2003, vol. 44, pp. 6179-6186."

(56) References Cited

OTHER PUBLICATIONS

Office Action (Final) dated Feb. 6, 2018 (43 pages), U.S. Appl. No. 15/167,009, filed May 27, 2016.
Office Action (Final) dated Feb. 6, 2018 (53 pages), U.S. Appl. No. 15/167,024, filed May 27, 2016.
Office Action (Final) dated Feb. 28, 2018 (43 pages), U.S. Appl. No. 15/167,017, filed May 27, 2016.
Bartlett, Stuart A., et al., "Activation of [CrCl3{R-SN(H)S-R}] Catalysts for Selective Trimerization of Ethene: A Freeze-Quench Cr K-Edge XAFS Study," ACS Catalysis, Oct. 21, 2014, pp. 4201-4204, vol. 4, No. 11, American Chemical Society.
Bhaduri, Sumit, et al., "Density functional studies on chromium catalyzed ethylene trimerization," Journal of Organometallic Chemistry, Apr. 15, 2009, pp. 1297-1307, vol. 694, Elsevier B. V.
Britovsek, George, J. P.; "A DFT Mechanistic Study on Ethylene Tri- and Tetramerization with Cr/PNP Catalysts: Single versus Double Insertion Pathways," Chemistry A European Journal, Nov. 14, 2016, pp. 16891-16896, vol. 22, No. 47, Wiley-VCH Verlag GmbH & Co. KGaA, Weinheim.
Britovsek, George, J. P.; "Mechanistic study of ethylene tri- and tetramerisation with Cr/PNP catalysts: effects of additional donors," Catalysis Science & Technology, Oct. 28, 2016, pp. 8234-8241, vol. 6, No. 23, Royal Society of chemistry.
Budzelaar, Peter H.M., "Ethene trimerization at CrI/CrIII—A Density functional theory (DFT) Study," Canadian Journal of Chemistry, 2009, pp. 832-837, vol. 87, Canadian Journal of Chemistry.
Filing receipt and specification for patent application entitled "Carbonyl-Containing Perfluorohydrocarbyl-N2-Phosphinyl Amidine Compounds, Chromium Salt Complexes and Their Use to Oligomerize Ethylene," by Steven M. Bischof, et al., filed Sep. 22, 2017 as U.S. Appl. No. 15/712,295.
Filing receipt and specification for patent application entitled "Perfluorohydrocarbyl-N2-Phosphinyl Amidine Compounds, Chromium Salt Complexes, Catalyst Systems, and Their Use to Oligomerize Ethylene," by Steven M. Bischof, et al., filed Sep. 22, 2017 as U.S. Appl. No. 15/712,304.
Filing receipt and specification for patent application entitled "Fluorinated N2-Phosphinyl Amidine Compounds, Chromium Salt Complexes, Catalyst Systems, and Their Use to Oligomerize Ethylene," by Steven M. Bischof, et al., filed Sep. 22, 2017 as U.S. Appl. No. 15/712,307.
Gong, Minglan, et al., "Selective Co-Oligomerization of Ethylene and 1-Hexene by Chromium-PNP Catalysts: A DFT Study," Organometallics, Mar. 29, 2016, pp. 972-981, vol. 35, No. 7, American Chemical Society.
Hossain, Anwar, et al., "Spin-crossover in Chromium-catalyzed Ethylene Trimerization" Density Functional Theory Study,"Bulletin of the Korean Chemical Society, Sep. 2014," pp. 2835-2838, vol. 35, No. 9, Korea Chemical Society.
Marenich, Aleksandr V., et al., "Universal Solvation Model Based on Solute Electron Density and on a Continuum Model of the Solvent Defined by the Bulk Dielectric Constant and Atomic Surface Tensions," Journal of Physical Chemistry B, Apr. 14, 2009, pp. 6378-6396, vol. 113, No. 18, American Chemical Society.
Qi, Yuan, et al., "Role of 1,2-Dimethoxyethane in the Transformation from Ethylene Polymerization to Trimerization Using Chromium Tris(2-ethylhexanoate)-Based Catalyst System: A DFT Study," Organometallics, Mar. 2, 2010, pp. 1588-1602, vol. 29, No. 7, American Chemical Society.
Van Rensburg, Werner Janse, et al., "A DFT Study toward the Mechanish of Chromium-Catalyzed Ethylene Trimerization," Organometallics, Feb. 17, 2004, pp. 1207-1222, vol. 23, No. 6, American Chemical Society.
Yang, Yun, et al., "Mechanistic DFT Study on Ethylene Trimerization of Chromium Catalysts Supported by a Versatile Pyrrole Ligand System," Organometallics, May 15, 2014, pp. 2599-2607, vol. 33, No. 10, American Chemical Society.
Fawcett, F.S., et al., "Cyanogen Fluoride: Synthesis and Properties," Journal of the American Chemical Society, Jul. 5, 1964, pp. 2576-2579, vol. 86, No. 13, American Chemical Society.
Morse, J. G., et al., "Substituted Difluoro- and Dichlorophosphines," Inorganic Syntheses, 1967, pp. 147-156, vol. 10, McGraw-Hill Book Company, Inc.
Singh, Rajendra P., et al., "The first application of SelectfluorTM in electrophilic fluorination of amines: a new route to $-NF_2$, $-NHF$, and $>NF$ compounds," Chemical Communication, 2001, pp. 1196-1197, vol. 13, Royal Society of Chemistry.
Office Action dated Jul. 27, 2018 (24 pages), U.S. Appl. No. 15/167,017, filed May 27, 2016.
Office Action dated Jun. 25, 2018 (43 pages), U.S. Appl. No. 15/719,107, filed Sep. 28, 2017.
Office Action dated Jul. 17, 2018 (53 pages), U.S. Appl. No. 15/615,113, filed Jun. 6, 2017.
Imhoff, Donald W., et al., "Characterization of Methylaluminoxanes and Determination of Trimethylaluminum Using Proton NMR," Organometallics, 1998, pp. 1941-1945, vol. 17, American Chemical Society.
Office Action dated Aug. 2, 2018 (19 pages), U.S. Appl. No. 15/167,024, filed May 27, 2016.

* cited by examiner

PROCESS IMPROVEMENTS IN SELECTIVE ETHYLENE OLIGOMERIZATIONS

TECHNICAL FIELD

The present disclosure relates to processes, systems, and reaction system configurations for oligomerization of ethylene.

BACKGROUND

The development of alpha olefin oligomerization techniques for the selective production of linear alpha olefins ($C_6$ to $C_{20}$) which do not utilize triethylaluminum (TEA) as part of the catalyst system has been a challenge. Both the economics and relative efficiency of TEA-based techniques have been difficult to match in alternative techniques. Some commercial success has been achieved using alternative techniques which use homogeneous catalyst systems; however, these techniques require extended secondary processing to recover the linear alpha olefins from undesired fractions/products such as butene or waxes. Other alternative catalyst systems have been developed for selective ethylene oligomerization. These selective ethylene oligomerization catalyst systems can produce desired linear alpha olefins without the drawbacks of the alternative techniques which use homogeneous catalyst systems. There is an ongoing need for improvements to selective ethylene oligomerization techniques.

SUMMARY

Disclosed herein are processes, systems, and/or reaction systems which include contacting 1) ethylene, 2) a catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane, 3) an organic reaction medium, and optionally 4) hydrogen; and forming an oligomer product in a reaction zone.

Further disclosed are processes, systems, and/or reaction systems which include introducing (or feeding) a catalyst system (or a catalyst system mixture) to a reaction zone, the catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane; introducing (or feeding) an ethylene feedstock mixture to the reaction zone separately from the catalyst system (or catalyst system mixture), the ethylene feedstock mixture comprising ethylene and at least a portion of an organic reaction medium used in the process, wherein the ethylene feedstock mixture is substantially free of the catalyst system; optionally introducing hydrogen to the reaction zone; and contacting the catalyst system and the ethylene feedstock mixture in the reaction zone to form an oligomer product.

Further disclosed are processes, systems, and/or reaction systems which include contacting in a reaction zone 1) ethylene, 2) a catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane, 3) an organic reaction medium, and 4) optionally hydrogen to form an oligomer product; wherein the catalyst system is fed to the reaction zone, an ethylene feedstock mixture comprising the ethylene and at least a portion of the organic reaction medium is fed separately from the catalyst system to the reaction zone, and the ethylene feedstock mixture is substantially free of the catalyst system.

Further disclosed are processes, systems, and/or reaction systems which include a) diluting an ethylene feed stream by addition of at least a portion of an organic reaction medium to the ethylene feed stream prior to contact of the ethylene feed stream with a catalyst system in a reaction zone; (b) contacting in the reaction zone the diluted ethylene feed stream with the catalyst system, wherein the catalyst system comprises i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane; and c) forming an oligomer product in the reaction zone.

Further disclosed herein are processes, systems, and/or reaction systems which include a) contacting ethylene and at least a portion of an organic reaction medium to form an ethylene feedstock mixture; b) subsequent to a), contacting in a reaction zone the ethylene feedstock mixture with a catalyst system mixture comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane; and c) forming an oligomer product in the reaction zone.

Further disclosed is a system comprising a feed stream comprising a mixture of ethylene and an organic reaction medium; a catalyst stream comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane; and a reaction zone receiving the feed stream separately from the catalyst stream, wherein ethylene is dispersed with the organic reaction medium to form the mixture prior to introduction of the mixture into the reaction zone via the feed stream.

Further disclosed herein is a reaction system comprising: a reaction zone; a first reaction zone inlet configured to introduce a catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane to the reaction zone; a second reaction zone inlet configured to introduce an ethylene feedstock mixture comprising ethylene and an organic reaction medium to the reaction zone, wherein the ethylene feedstock mixture is substantially free of the catalyst system; and one or more reaction zone outlets configured to discharge a reaction zone effluent comprising an oligomer product from the reaction zone.

Further disclosed herein is a reaction system comprising: a reaction zone having a reaction zone inlet; an ethylene feed line in fluid communication with the reaction zone inlet and comprising ethylene; an organic reaction medium feed line in fluid communication with the reaction zone inlet and comprising an organic reaction medium, wherein the ethylene feed line and the organic reaction medium feed line join to produce an ethylene feedstock mixture prior to the reaction zone inlet; a catalyst system feed line in fluid communication with the reaction zone inlet and comprising a catalyst system and which can combine with the ethylene feedstock mixture to yield a combined feed line, wherein the combined feed line can flow to the reaction zone via the reaction zone inlet; a reaction zone outlet configured to discharge a reaction zone effluent comprising an oligomer product from the reaction zone; wherein the catalyst system comprises i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane.

In the disclosed processes, systems, and/or reaction systems, ethylene can be contacted with at least a portion of the organic reaction medium to form an ethylene feedstock mixture prior to contacting ethylene with the catalyst system. In these processes, systems, and/or reaction systems it is contemplated that the ethylene feedstock mixture can be contacted with the catalyst system inside the reaction zone or outside the reaction zone.

BRIEF DESCRIPTION OF THE DRAWINGS

For a detailed description, reference will now be made to the accompanying drawings.

DETAILED DESCRIPTION

Figure 1:
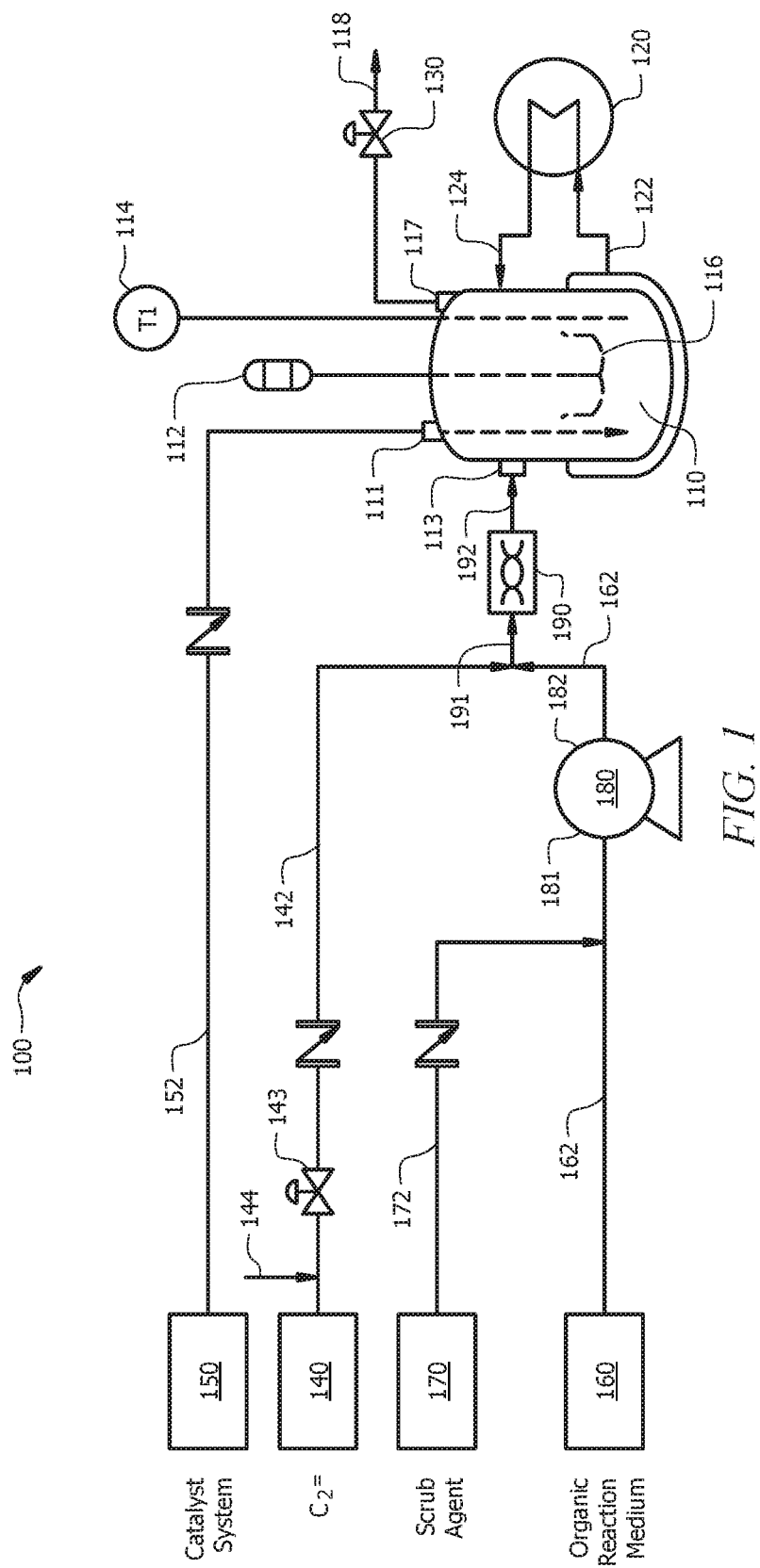
FIG. 1 shows a process flow diagram of a reaction system according to the present disclosure.

In the description herein, various ranges and/or numerical limitations can be expressly stated below. It should be recognized that unless stated otherwise, it is intended that endpoints are to be interchangeable. Further, any ranges include iterative ranges of like magnitude falling within the expressly stated ranges or limitations.

Furthermore, various modifications can be made within the scope of the invention as herein intended, and embodiments of the invention can include combinations of features other than those expressly claimed. In particular, flow arrangements other than those expressly described herein are within the scope of the invention.

Unless otherwise specified, the terms "contact" and "combine," and their derivatives, can refer to any addition sequence, order, or concentration for contacting or combining two or more components of the disclosed embodiments. Combining or contacting of oligomerization components can occur in one or more reaction zones under suitable contact conditions such as temperature, pressure, contact time, flow rates, etc.

Regarding claim transitional terms or phrases, the transitional term "comprising", which is synonymous with "including," "containing," "having" or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter composition or method to which the term is applied. For example, a feedstock consisting of a material A can include impurities typically present in a commercially produced or commercially available sample of material A. When a claim includes different features and/or feature classes (for example, a method step, feedstock features, and/or product features, among other possibilities), the transitional terms comprising, consisting essentially of, and consisting of apply only to the feature class that is utilized and it is possible to have different transitional terms or phrases utilized with different features within a claim. For example a method can comprise several recited steps (and other non-recited steps) but utilize a catalyst system preparation consisting of specific steps can utilize a catalyst system comprising recited components and other non-recited components.

Within this specification, use of "comprising" or an equivalent expression contemplates the use of the phrase "consisting essentially of," "consists essentially of," or equivalent expressions as alternative embodiments to the open-ended expression. Additionally, use of "comprising" or an equivalent expression or use of "consisting essentially of" in the specification contemplates the use of the phrase "consisting of," "consists of," or equivalent expressions as an alternative to the open-ended expression or middle ground expression, respectively. For example, "comprising" should be understood to include "consisting essentially of," and "consisting of" as alternative embodiments for the aspect, features, and/or elements presented in the specification unless specifically indicated otherwise.

While compositions and methods are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "a trialkylaluminum compound" is meant to encompass one trialkylaluminum compound, or mixtures or combinations of more than one trialkylaluminum compound unless otherwise specified.

Unless otherwise indicated, the definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition can be applied. To the extent that any definition or usage provided by any document incorporated herein by reference conflicts with the definition or usage provided herein, the definition or usage provided herein controls.

Groups of elements of the Periodic Table are indicated using the numbering scheme indicated in the version of the Periodic Table of elements published in *Chemical and*

*Engineering News*, 63(5), 27, 1985. In some instances, a group of elements can be indicated using a common name assigned to the group; for example, alkali metals for Group 1 elements, alkaline earth metals (or alkaline metals) for Group 2 elements, transition metals for Groups 3-12 elements, and halogens for Group 17 elements.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to hexene includes 1-hexene, 2-hexene, 3-hexene, and any other hydrocarbon having 6 carbon atoms (linear, branched or cyclic) and a single carbon carbon double bond. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure of a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. An "organyl group," "organylene group," or "organic group" can be aliphatic, inclusive of being cyclic or acyclic, or can be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional groups" definition includes the hydrocarbyl group as a member (among other groups). Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group which does not substantially interfere with the process described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. For example, while an ether group can complex with a metal compound, an ether group located at a para position of a substituted phenyl phosphinyl group in an $N^2$-phosphinyl amidine can be an inert functional group because a single metal compound cannot complex with both the para ether group and the $N^2$-phosphinyl amidine group in a single metal complex molecule. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), sulfidyl groups, and/or hydrocarbyl groups, among others.

The term "hydrocarbon" whenever used in this specification and claims refers to a compound containing only carbon and hydrogen. Other identifiers can be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from the carbon atom of an aliphatic compound. Aliphatic compounds and therefore aliphatic groups can contain organic functional group(s) and/or atom(s) other than carbon and hydrogen.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc. . . . carbon-carbon double bonds can be identified by use of the term "mono," "di," "tri," etc. . . . within the name of the olefin. The olefins can be further identified by the position of the carbon-carbon double bond(s).

The term "alkene" whenever used in this specification and claims refers to a linear or branched aliphatic hydrocarbon olefin that has one or more carbon-carbon double bonds. Alkenes having only one, only two, only three, etc. . . . such multiple bonds can be identified by use of the term "mono," "di," "tri," etc. . . . within the name. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of other carbon-carbon double bonds unless explicitly indicated.

The term "normal alpha olefin" whenever used in this specification and claims refers to a linear aliphatic mono-olefin having a carbon-carbon double bond between the first and second carbon atoms. It is noted that "normal alpha olefin" is not synonymous with "linear alpha olefin" as the term "linear alpha olefin" can include linear olefinic compounds having a double bond between the first and second carbon atoms and additional double bonds.

The term "reaction zone effluent," and it derivatives generally refers to all materials which exit the reaction zone through a reaction zone outlet which discharges a reaction mixture and can include reaction system feed(s) (e.g., ethylene, catalyst system or catalyst system components, and/or organic reaction medium), and/or reaction product(s) (e.g., oligomer product including oligomers and non-oligomers). The term "reaction zone effluent" and its derivatives can be qualified to refer to certain portions by use of additional qualifying terms. For example, while reaction zone effluent refers to all material which exits the reaction system through the reaction zone outlet/discharge, a reaction zone oligomer product effluent refers to only the oligomer product within the reaction zone effluent.

The terms "room temperature" or "ambient temperature" are used herein to describe any temperature from 15° C. to 35° C. wherein no external heat or cooling source is directly applied to the reaction vessel. Accordingly, the terms "room temperature" and "ambient temperature" encompass the individual temperatures and any and all ranges, subranges, and combinations of subranges of temperatures from 15° C. to 35° C. wherein no external heating or cooling source is directly applied to the reaction vessel. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa).

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" for the feature disclosed herein.

Within this disclosure the normal rules of organic nomenclature prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. References to compounds or groups having substitution at positions in addition to the indicated position can be referenced using comprising or some other alternative language. For example a reference to a phenyl group comprising a substituent at the 4 position refers to a phenyl group having a non-hydrogen substituent group at the 4 position and hydrogen or any non-hydrogen group at the 2, 3, 5, and 6 positions.

Use of the term "optionally" with respect to any element of a claim is intended to mean that the subject element is required, or alternatively, is not required. Both alternatives are intended to be within the scope of the claim.

Processes, systems, and/or reaction systems described herein can utilize steps, features, compounds and/or equipment which are independently described herein. The processes, systems, and/or reaction systems described herein may or may not utilize step identifiers (e.g., 1), 2), etc., a), b), etc., i), ii), etc., or first, second etc., among others), feature identifiers (e.g., 1), 2), etc., a), b), etc., i), ii), etc., or first, second etc., among others), and/or compound and/or composition identifiers (e.g., 1), 2), etc., a), b), etc., i), ii), etc., or first, second etc., among others). However, it should be noted that processes, systems, and/or reaction systems described herein can have multiple steps, features (e.g. reagent ratios, formation conditions, among other considerations), and/or multiple compounds and/or composition using no descriptor or sometimes having the same general identifier. Consequently, it should be noted that the processes, systems, and/or reaction systems described herein can be modified to use an appropriate step or feature identifier (e.g., 1), 2), etc., a), b), etc., i), ii), etc., or first, second etc., among others), feature identifier (e.g., 1), 2), etc., a), b), etc., i), ii), etc., or first, second etc., among others), and/or compound identifier (e.g., first, second, etc.) regardless of step, feature, and/or compound identifier utilized in the a particular aspect and/or embodiment described herein and that step or feature identifiers can be added and/or modified to indicate individual different steps/features/compounds utilized within the processes, systems, and/or reaction systems without detracting from the general disclosure.

Processes, systems, and/or reaction systems for forming oligomer products are described herein. Such processes generally comprise contacting ethylene and a catalyst system to form an oligomer product under oligomerization conditions. As used herein, the term "oligomerization" and its derivatives, refers to processes which produce a mixture of products containing at least 70 weight percent products containing from 2 to 30 ethylene units. Similarly, as used herein, an "oligomer" is a product that contains from 2 to 30 ethylene units while an "oligomer product" includes all products made by the process including the "oligomers" and products which are not "oligomers" (e.g., products which contain more than 30 monomer units). Further the terms "oligomer product" and "oligomerization product" can be used interchangeably.

As used herein, the term "trimerization," and it derivatives, refers to a process, system, and/or reaction system which produces a mixture of products containing at least 70 weight percent products containing three and only three ethylene units. As used herein a "trimer" is a product which contains three and only three ethylene units while a "trimerization product" includes all products made by the trimerization process including trimer and product which are not trimers (e.g. dimers or tetramers). Generally, a "trimerization" process using ethylene produces an oligomer product containing at least 70 weight percent hexene(s).

As used herein, the term "tetramerization," and its derivatives, refers to a process, system, and/or reaction system which produces a mixture of products containing at least 70 weight percent products containing four and only four ethylene units. As used herein a "tetramer" is a product which contains four and only four ethylene units while a "tetramerization product" includes all products made by the tetramerization process including tetramer and products which are not tetramers (e.g. dimers or trimer). Generally, a "tetramerization" process using ethylene produces an oligomer product containing at least 70 weight percent octene(s).

As used herein, the term "trimerization and tetramerization," and it derivatives, refers to a process, system, and/or reaction system which produces an oligomer product containing at least 70 weight percent products containing three and/or four and only three and/or four ethylene units. As used herein a "trimerization and tetramerization product" includes all products made by the "trimerization and tetramerization" process including trimer, tetramer, and products which are not trimers or tetramers (e.g. dimers). Generally, a "trimerization and tetramerization" process using ethylene produces an oligomer product containing at least 70 weight percent hexene(s) and/or octene(s).

Various aspects and embodiments described herein may refer to a substituted group or compound. In an embodiment, each substituent of any aspect or embodiment calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In an embodiment, each hydrocarbyl substituent can be a $C_1$ to $C_{10}$ hydrocarbyl group; or alternatively, a $C_1$ to $C_5$ hydrocarbyl group. In an embodiment, each hydrocarboxy group can be a $C_1$ to $C_{10}$ hydrocarboxy group; or alternatively, a $C_1$ to $C_5$ hydrocarboxy group.

In an embodiment, any halide substituent of any aspect or embodiment calling for a substituent can be a fluoride, chloride, bromide, or iodide; alternatively, a fluoride or chloride. In some embodiments, any halide substituent of any aspect or embodiment calling for a substituent can be a fluoride; alternatively, a chloride; alternatively, a bromide; or alternatively, an iodide.

In an embodiment, any hydrocarbyl substituent of any aspect or embodiment calling for a substituent can be an alkyl group, an aryl group, or an aralkyl group; alternatively, an alkyl group; alternatively, an aryl group; or alternatively, an aralkyl group. In an embodiment, any alkyl substituent of any aspect or embodiment calling for a substituent can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl substituent of any aspect or embodiment calling for a substituent can be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, any aralkyl substituent of any aspect or embodiment calling for a substituent can be benzyl group or an ethylphenyl group (2-phenyleth-1-yl or 1-phenyleth-1-yl); alternatively, a benzyl group; alternatively, an ethylphenyl group; alternatively a 2-phenyleth-1-yl group; or alternatively, a 1-phenyleth-1-yl group.

In an embodiment, any hydrocarboxy substituent of any aspect or embodiment calling for a substituent can be an alkoxy group, an aryloxy group, or an aralkoxy group; alternatively, an alkoxy group; alternatively, an aryloxy group, or an aralkoxy group. In an embodiment, any alkoxy substituent of any aspect or embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryloxy substituent of any aspect or embodiment calling for a substituent can be phenoxy group, a toloxy group, a xyloxy group, or a 2,4,6-trimethylphenoxy group; alternatively, a phenoxy group; alternatively, a toloxy group, alternatively, a xyloxy group; or alternatively, a 2,4,6-trimethylphenoxy group. In an embodiment, any aralkoxy substituent of any aspect or embodiment calling for a substituent can be benzoxy group.

Aspects disclosed herein can provide the materials listed as suitable for satisfying a particular feature of the embodiment delimited by the term "or." For example, a particular feature of the disclosed subject matter can be disclosed as follows: Feature X can be A, B, or C. It is also contemplated that for each feature the statement can also be phrased as a listing of alternatives such that the statement "Feature X is A, alternatively B, or alternatively C" is also an embodiment of the present disclosure whether or not the statement is explicitly recited.

Disclosed herein are processes, systems, and/or reaction systems for the oligomerization of ethylene to form an oligomer product. In an embodiment the oligomer product can comprise normal linear alpha olefins (NAO). In particular, the processes, systems, and/or reaction systems described herein can selectively trimerize, tetramerize, or trimerize and tetramerize ethylene to produce an oligomer product containing hexenes (e.g., 1-hexene) and/or octenes (e.g., 1-octene). It has been unexpectedly found that the selective ethylene oligomerization processes, systems, and/or reaction systems using the catalyst systems disclosed herein are sensitive to specific reactor feed conditions. For example, it has been found that polymer can form with use of the disclosed selective ethylene oligomerization catalyst systems when concentrated portions of ethylene are contacted with a catalyst system. The contacting of a high concentration of ethylene with the selective ethylene oligomerization catalyst system can make polymer plugging and/or fouling of reaction zone components the major limiting factor in oligomer production. It has also been found that the disclosed processes, systems, and/or reaction systems can reduce the amount of polymer in the reaction zone during operation of a selective olefin oligomerization reaction, increase hexenes and/or octenes productivity and/or production, and avoid fouling and/or plugging of reaction zone and/or reaction system components.

Figure 2:
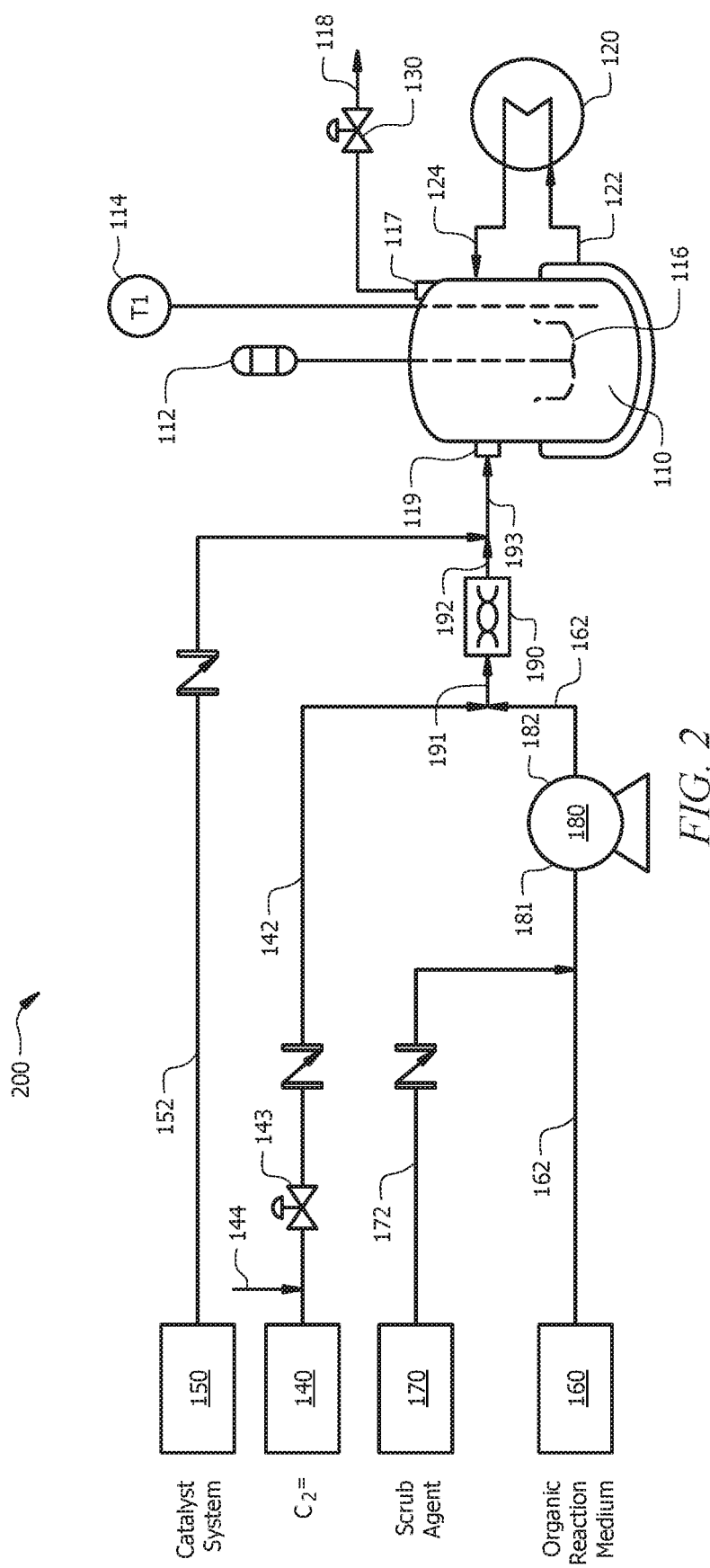
FIG. 2 shows a process flow diagram of another reaction system according to the present disclosure.

The disclosed processes, systems, and/or reaction systems (e.g., those illustrated in FIG. 1 and FIG. 2), can comprise contacting 1) ethylene, 2) a catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane, 3) an organic reaction medium, and optionally 4) hydrogen; and forming an oligomer product in a reaction zone. In the disclosed processes, systems, and/or reaction systems, ethylene can be contacted with at least a portion of the organic reaction medium to form an ethylene feedstock mixture prior to contacting ethylene with the catalyst system. In these processes, systems, and/or reaction systems it is contemplated that the ethylene feedstock mixture can be contacted with the catalyst system inside the reaction zone or outside the reaction zone. Additionally, the catalyst system and the ethylene feedstock mixture can be contacted prior entering the reaction zone or the catalyst system can be introduced into the reaction zone separately from the ethylene feedstock mixture; alternatively, the catalyst system and the ethylene feedstock mixture can be contacted prior entering the reaction zone; or alternatively, the catalyst system can be introduced into the reaction zone separately from the ethylene feedstock mixture. In an embodiment of the processes, systems, and reaction systems (e.g., reaction systems 100 and 200) disclosed herein, substantially all of the ethylene can be contacted with the catalyst system and/or introduced/fed to the reaction zone (e.g., reaction zone 110) via the ethylene feedstock mixture; or alternatively, substantially all of the ethylene can be contacted with at least a portion of the organic reaction medium prior to the ethylene contacting the catalyst system. For example, as shown in FIG. 1, the catalyst system can be introduced into the reaction zone (via line 152 which feeds to the first reaction zone inlet 111, discussed in detail herein) separately from the ethylene feedstock mixture (via line 162 which feeds to the second reaction zone inlet 113, also discussed in detail below). Alternatively, as shown in FIG. 2, the catalyst system and the ethylene feedstock mixture can be contacted prior to entering the reaction zone (line 152 combines with line 192 before the components enter the reaction zone inlet 119, discussed in detail herein). By "substantially all" it is meant that at least 95, 97, 99, 99.5, 99.75, or 99.9 mol % of the ethylene fed to the reaction zone in the process, systems, and/or reaction systems described herein is the ethylene feedstock mixture (or alternatively, contacts the at least a portion of the organic reaction medium prior to contacting the catalyst system).

Also disclosed herein, are processes, systems, and/or reaction systems (e.g., those illustrated in FIG. 1 and FIG. 2) comprising introducing (or feeding) a catalyst system (or a catalyst system mixture) to a reaction zone, the catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane; introducing (or feeding) an ethylene feedstock mixture to the reaction zone separately from the catalyst system (or catalyst system mixture), the ethylene feedstock mixture comprising ethylene and at least a portion of an organic reaction medium used in the process, wherein the ethylene feedstock mixture is substantially free of the catalyst system; optionally introducing hydrogen to the reaction zone; and contacting the catalyst system and the ethylene feedstock mixture in the reaction zone to form an oligomer product.

Further disclosed herein, are processes, systems, and/or reaction systems (e.g., those illustrated in FIG. 1 and FIG. 2) comprising contacting in a reaction zone 1) ethylene, 2) a catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane, 3) an organic reaction medium, and 4) optionally hydrogen to form an oligomer product; wherein the catalyst system is fed to the reaction zone, an ethylene feedstock mixture comprising the ethylene and at least a portion of the organic reaction medium is fed separately from the catalyst system to the reaction zone, and the ethylene feedstock mixture is substantially free of the catalyst system.

The disclosed processes, systems, and/or reaction systems (e.g., those illustrated in FIG. 1 and FIG. 2) can alternatively comprise a) diluting an ethylene feed stream by addition of at least a portion of an organic reaction medium to the ethylene feed stream prior to contact of the ethylene feed stream with a catalyst system in a reaction zone; (b) contacting in the reaction zone the diluted ethylene feed stream with the catalyst system, wherein the catalyst system comprises i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane; and c) forming an oligomer product in the reaction zone.

The disclosed processes, systems, and/or reaction systems (e.g., those illustrated in FIG. 1 and FIG. 2) can alternatively comprise a) contacting ethylene and at least a portion of an organic reaction medium to form an ethylene feedstock mixture; b) subsequent to a), contacting in a reaction zone the ethylene feedstock mixture with a catalyst system mixture comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane; and c) forming an oligomer product in the reaction zone.

Further disclosed is a system comprising a feed stream comprising a mixture of ethylene and an organic reaction medium; a catalyst stream comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane; and a reaction zone receiving the feed stream separately from the catalyst stream, wherein ethylene is dispersed with the organic reaction medium to form the mixture prior to introduction of the mixture into the reaction zone via the feed stream.

Further disclosed herein is a reaction system comprising: a reaction zone; a first reaction zone inlet configured to introduce a catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane to the reaction zone; a second reaction zone inlet configured to introduce an ethylene feedstock mixture comprising ethylene and an organic reaction medium to the reaction zone, wherein the ethylene feedstock mixture is substantially free of the catalyst system; and one or more reaction zone outlets configured to discharge a reaction zone effluent comprising an oligomer product from the reaction zone. In an embodiment, the reaction system can further comprise a catalyst system feed line flowing the catalyst system to the first reaction zone inlet, an ethylene feed line comprising the ethylene, and/or an organic reaction medium feed line comprising the organic reaction medium. In some embodiments, the organic reaction medium feed line and the ethylene feed line can be combined to yield the ethylene feedstock mixture which can be introduced to the second reaction zone inlet. In further embodiments, the reaction system can further comprise a pump in fluid communication with the second reaction zone inlet located upstream of a point where the ethylene feed line and the organic reaction medium feed line join to produce the ethylene feedstock mixture. In yet further embodiments, the reaction system can further comprise a mixing device positioned between i) the joining of the ethylene feed line and the organic reaction medium feed line, and ii) the second reaction zone inlet, to disperse the ethylene and the organic reaction medium in the ethylene feedstock mixture prior to the ethylene feedstock mixture entering the reaction zone. In some embodiments, the first reaction zone inlet can be configured to periodically or continuously introduce the catalyst system to the reaction zone, the second reaction zone inlet can be configured to periodically or continuously introduced the ethylene feedstock mixture to the reaction zone, and/or the one or more reaction zone outlets can be configured to periodically or continuously discharge the reaction zone effluent comprising the oligomer product from the reaction zone.

Further disclosed herein is a reaction system comprising: a reaction zone having a reaction zone inlet; an ethylene feed line in fluid communication with the reaction zone inlet and comprising ethylene; an organic reaction medium feed line in fluid communication with the reaction zone inlet and comprising an organic reaction medium, wherein the ethylene feed line and the organic reaction medium feed line join to produce an ethylene feedstock mixture prior to the reaction zone inlet; a catalyst system feed line in fluid communication with the reaction zone inlet and comprising a catalyst system and which can combine with the ethylene feedstock mixture to yield a combined feed line, wherein the combined feed line can flow to the reaction zone via the reaction zone inlet; a reaction zone outlet configured to discharge a reaction zone effluent comprising an oligomer product from the reaction zone; wherein the catalyst system comprises i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane. In an embodiment, the reaction system can further comprise a pump in fluid communication with the reaction zone inlet. In an embodiment the pump can be located upstream of a point where the ethylene feed line and the organic reaction medium feed line join to produce the ethylene feedstock mixture. In another embodiment, the reaction system can further comprise a mixing device positioned between i) the joining of the ethylene feed line and the organic reaction medium feed line and ii) the reaction zone inlet to disperse the ethylene and the organic reaction medium in the ethylene feedstock mixture prior to the ethylene feedstock mixture joining with the catalyst system and entering the reaction zone. In a further embodiment, the reaction zone inlet can be configured to periodically or continuously introduce the combined feed line to the reaction zone, and/or the reaction zone outlet can be configured to periodically or continuously discharge the reaction zone effluent from the reaction zone.

In an embodiment of any process, system, or reaction system disclosed, at least a portion of the organic reaction medium can be contacted with a scrub agent (e.g., alkylaluminum compound) prior to introducing/feeding of the at least a portion of the organic reaction medium to the reaction zone; or alternatively, contacting in the reaction zone ethylene feedstock mixture with a catalyst system mixture. In some embodiments, the at least a portion of the organic reaction medium can be contacted with a scrub agent (e.g., an alkylaluminum compound) prior to contact of ethylene with the at least a portion of the organic reaction medium. In other embodiments, the at least a portion of the organic reaction medium can be contacted with the ethylene feedstock mixture prior to introduction of the ethylene feedstock mixture to the reaction zone.

In any process, system, and/or reaction system disclosed herein, the catalyst system can be dispersed in a solvent and/or diluent prior to contacting ethylene. In some embodiments, the solvent and/or diluent can be any organic reaction medium disclosed herein. In some embodiments, the solvent and/or diluent can be the same as the organic reaction medium; or alternatively, the solvent and/or diluent can be a different organic reaction medium. Additionally, any process, system, and/or reaction system disclosed herein can form the oligomer product (or alternatively, the reaction zone can operate) at any condition or combination of conditions disclosed herein.

It is further contemplated, for any process, system, or reaction system disclosed herein, that ethylene and the organic reaction medium can be dispersed in the ethylene feedstock mixture prior to introducing/feeding the ethylene feedstock mixture to the reaction zone; or alternatively prior to contact of the ethylene feedstock mixture with the catalyst system outside of the reaction zone. The dispersion can be accomplished by the use of a mixing device (described further herein). For example, as shown in FIG. 1, the ethylene feedstock mixture in line 191 can pass through mixing device 190 prior to entering the reaction zone through reaction zone inlet 113 (discussed in detail herein). Alternatively, as shown in FIG. 2, the ethylene feedstock mixture in line 191 can pass through mixing device 190 prior to contacting the catalyst system in line 152 and the combined stream can enter reaction zone 110 through the reaction zone inlet 119 (discussed in detail below).

Any process, system, and/or reaction system described herein can further comprise preparing the catalyst system. In an embodiment, the catalyst system can be prepared by 1) contacting the chromium component (any described herein) and the aluminoxane compound (any described herein) to form a catalyst system mixture, and 2) aging the catalyst system mixture in the substantial absence of ethylene to form an aged catalyst system mixture. In an embodiment the catalyst system mixture can be aged for a period of time. Typically, the minimum aging time can be 5 seconds, 10 seconds, 30 seconds, 1 minute, 5 minutes, 10 minutes, or 20 minutes; additionally or alternatively, the maximum aging time can be 48 hours, 36 hours, 24 hours, 18 hours, 12 hours, 6 hours, 4 hours, or 2 hours. Generally, the aging time can be in a range from any minimum time disclosed herein to any maximum time disclosed herein. Accordingly, suitable non-limiting ranges for the aging time can include from 5 seconds to 48 hours, from 10 seconds to 36 hours, from 30 seconds to 24 hours, from 1 minute to 18 hours, from 5 minutes to 6 hours, from 10 minutes to 4 hours, or from 20 minutes to 2 hours. Other appropriate ranges for the aging time are readily apparent from this disclosure. In further embodiments, the catalyst system mixture can be aged at any suitable temperature, ranging from sub-ambient temperatures, to ambient temperature (approximately 25° C.), to elevated temperatures. While not being limited thereto, the catalyst system mixture can be aged at a temperature in a range from 0° C. to 100° C., from 10° C. to 75° C., from 15° C. to 60° C., or from 20° C. to 40° C. In these and other embodiments, these temperature ranges also are meant to encompass circumstances where the catalyst system mixture can be aged at a series of different temperatures, instead of at a single fixed temperature, falling within the respective ranges. In a non-limiting embodiment, a substantial absence of ethylene can be a maximum molar ratio of ethylene to chromium of the chromium component of 5:1, 4:1, 3:1, 2:1, 1:1, 0.5:1, 0.25:1, or 0.1:1. In some non-limiting embodiments, the substantial absence of ethylene can be a maximum ethylene partial pressure 10 psig (69 kPa), 5 psig (34 kPa), 4 psig (28 kPa), 3 psig (21 kPa), 2 psig (14 kPa), 1 psig (7 kPa), or 0.5 psig (3.4 kPa). In some embodiments, the catalyst system can be formed by contact a diluent and/or a solvent with the chromium component (any described herein) and the organoaluminum compound (any described herein). In an embodiment, the diluent and/or solvent can be any organic reaction medium described herein. In some embodiments, the catalyst system can be formed by contact a diluent and/or a solvent with the chromium component (any described herein) and the aluminoxane (any described herein). In an embodiment, the diluent and/or solvent can be any organic reaction medium described herein. In embodiments where the catalyst system can be formed by contact a diluent and/or a solvent with the chromium component (any described herein) and the aluminoxane, the chromium component to solvent and/or diluent weight ratio can range from 1:100 to 1:15,000, or 1:150 to 1:10,000.

FIG. 1 shows a process flow diagram of a reaction system 100 according to the present disclosure. The system 100 includes one or more of an ethylene source 140 in fluid communication with an ethylene feed line 142; a catalyst system source 150 in fluid communication with a catalyst system feed line 152; an organic reaction medium source 160 in fluid communication with an organic reaction medium feed line 162; an optional scrub agent source 170 in communication with a scrub agent feed line 172; an optional hydrogen feed line 144 feeding to the ethylene feed line 142; an optional pump 180; an optional mixing device 190; a reaction zone 110 having a first reaction zone inlet 111, a second reaction zone inlet 113, and a reaction zone outlet 117 representing one or more reaction zone outlets; and a heat exchanger 120. It is contemplated that reaction system 100 of FIG. 1 can include appropriate equipment (e.g., valves, control devices, sensors, electrical writing, insulation) which are not shown in FIG. 1 yet can be included according to those skilled in the art with the aid of this disclosure.

The first reaction zone inlet 111 (representing one or more reaction zone inlets) can be configured to introduce a catalyst system as described herein to the reaction zone 110, the second reaction zone inlet 113 (representing one or more reaction zone inlets) can be configured to introduce an ethylene feedstock mixture to the reaction zone 110, and the reaction zone outlet 117 representing one or more reaction zone outlets can be configured to discharge or remove a reaction zone effluent comprising an oligomer product from the reaction zone 110 via line 118. For the reaction zone 110 configuration shown in FIG. 1, the inlets 111 and 113 can be placed as far away from one another as possible. In an aspect, the inlet 111 is placed near the stirring in the reaction zone 110 to improve dispersion of the catalyst system in the reaction zone 110 before contacting ethylene which is introduced via inlet 113. Other considerations for placement of the inlets 111 and 113 as well as outlet 117 may be taken into account, for example, when the reaction zone 110 includes a recycle feature. Reaction zone effluent in line 118 can then feed to equipment (not shown) for isolating various streams (e.g., the desired oligomer) from the reaction zone effluent. Valve 130 can be used in line 118 to control a flow of the reaction zone effluent in line 118 and/or to control a pressure of the reaction zone 110.

In FIG. 1, the ethylene feedstock mixture, the catalyst system, and optionally, hydrogen can be periodically or continuously introduced to the reaction zone 110. Moreover, the reaction zone effluent can be periodically or continuously removed from the reaction zone 110. For example, the first reaction zone inlet 111 (representing one or more reaction zone inlets) is configured to periodically or continuously introduce the catalyst system to the reaction zone 110, the second reaction zone inlet 113 (representing one or more reaction zone inlets) is configured to periodically or continuously introduce the ethylene feedstock mixture to the reaction zone 110, and the reaction zone outlet 117 (representing one or more reaction zone outlets) is configured to periodically or continuously discharge or remove the reaction zone effluent comprising oligomer product from the reaction zone 110.

The catalyst system flows through catalyst system feed line 152 from the catalyst system source 150 to the first reaction zone inlet 111, where the catalyst system is fed to the reaction zone 110. The catalyst system feed line 152 can optionally include a solvent and/or a diluent with the catalyst system. The solvent and/or diluent can be any organic reaction medium described herein. In some embodiments, the solvent and/or diluent can be the organic reaction medium used in the ethylene feedstock mixture. The catalyst system can be dispersed in the solvent and/or diluent in the catalyst system feed line 152. For example, the catalyst system feed line 152 can include a mixing device (not shown), similar to mixing device 190 (described herein) or a precontactor apparatus (not shown), which is configured to disperse the catalyst system in the diluent prior to the catalyst system entering the reaction zone 110 via first reaction zone inlet 111. When solvent and/or diluent and the catalyst system are present in the catalyst system feed line 152 of FIG. 1, the chromium:solvent and/or diluent mass ratio can be any disclosed herein.

Optionally, scrub agent (described herein) can flow in the scrub agent feed line 172. In some embodiments, the scrub agent may not be the aluminoxane of the catalyst system.

Organic reaction medium can flow in organic reaction medium feed line 162 from the organic reaction medium source 160 to the suction side 181 of pump 180.

At least a portion of the organic reaction medium can be contacted with a scrub agent (e.g., an alkylaluminum compound, any described herein) prior to introduction to the reaction zone 110. FIG. 1 shows scrub agent can be added via feed line 172 to the organic reaction medium feed line 162 such that line 162 contains both the scrub agent and the organic reaction medium. Alternatively, the scrub agent is not combined with the organic reaction medium in the organic reaction medium. The scrub agent is independently disclosed herein and can be utilized to further described reaction system 100.

At least a portion of the organic reaction medium can be contacted with the scrub agent (e.g., an alkylaluminum compound, any described herein) prior to contact of the portion of organic reaction medium with ethylene. FIG. 1 shows the scrub agent can be added via line 172 to the organic reaction medium feed line 162, before the organic reaction medium contacts ethylene via combination of the organic reaction medium feed line 162 with the ethylene feed line 142. The scrub agent is independently disclosed herein and can be utilized to further described reaction system 100.

In FIG. 1, all of the organic reaction medium can be fed to the reaction zone via line 162. However, as is discussed herein, it is contemplated that only a portion of the total amount of organic reaction medium which is used in the system 100 is in line 162 and optionally contacted with the scrub agent prior to introduction to the reaction zone 110; e.g., the other portions can be mixed with the catalyst system in catalyst system feed line 152 and/or can be included in a bypass line which feeds directly to the reaction zone 110. Alternatively, the scrub agent may not combined with the organic reaction medium, and the organic reaction medium feed line 162 can flow directly to the suction side 181 of pump 180.

Ethylene flows in ethylene feed line 142 from the ethylene source 140 and can combine with organic reaction medium (which optionally can be previously combined with scrub agent) flowing in line 162 on the head side 182 of the pump 180. Alternatively, ethylene can be combined with the organic reaction medium (and any optional scrub agent) flowing in line 162 on the suction side 181 of the pump 180.

Combination of the ethylene in line 142 with the organic reaction medium in line 162 yields an ethylene feedstock mixture in ethylene feedstock mixture feed line 191. The ethylene feedstock mixture can flow through an optional mixing device 190 where ethylene and the organic reaction medium (which optionally can be previously combined with scrub agent) can be dispersed, and subsequently flow via dispersed ethylene feedstock mixture feed line 192 as a dispersed ethylene feedstock mixture to the second reaction zone inlet 113.

Hydrogen optionally can be used to control the ethylene oligomerization reaction. The optional hydrogen can be fed into the ethylene feed line 142 of reaction system 200 via hydrogen feed line 144. The combination of hydrogen with ethylene in the ethylene feed line 144 can be upstream of valve 143 as shown in FIG. 1; or alternatively, downstream of valve 143. While the hydrogen feed line 144 in FIG. 1 is shown as feeding to the ethylene feed line 142, it is contemplated that the hydrogen feed line 144 can fluidly connect to any reaction zone inlet (e.g., reaction zone inlet 111 or reaction zone inlet 113) directly or via another line (e.g., line 152, line 162, line 172, line 191, or line 192).

Reaction zone 110 is shown in FIG. 1 as a single continuous stirred-tank reactor operating in continuous mode. Various alternative reactors, reactor configurations and/or operating modes that can achieve similar ethylene oligomerization results are contemplated for the reaction zone 110 and are discussed in more detail herein. Thermocouple 114 can read the temperature of the reaction zone 110 as the ethylene oligomerization proceeds. Stirrer 116 operated by motor 112 can agitate the contents of the reaction zone 110. The stirrer can be an impeller coupled to the motor 112 via a rod. Heat exchanger 120 receives line 122 and provides line 124 to the reaction zone 110 in order to maintain a temperature of the reaction zone 110.

A reaction zone effluent comprising oligomer product formed in the reaction zone 110 flows in line 118 from reaction zone outlet 117. In some embodiments, the oligomer product in line 118 can flow to a product recovery zone (not shown). The product recovery zone can include catalyst system deactivation, an oligomer product separation where the oligomer product (e.g., hexenes and/or octenes) can be recovered from the reaction zone effluent via techniques known in the art with the aid of this disclosure (e.g., distillation, flashing, absorption, stripping), by-product separation and/or isolation, and/or any steps which can facilitate the handling of the reaction zone effluent and the isolation of the desired ethylene oligomers.

It is noted that in the system 100 of FIG. 1, the ethylene feedstock mixture comprising ethylene and at least a portion of the organic reaction medium (in the case of FIG. 1, all of the organic reaction medium used in system 100) can be fed to the reaction zone 110 separately with respect to the catalyst system. That is, the ethylene feedstock mixture is fed to the reaction zone 110 via lines 191 and 192 and via second reaction zone inlet 113; while, the catalyst system can be fed to the reaction zone 110 via line 152 and via first reaction zone inlet 111.

The separately fed ethylene feedstock mixture in any of lines 191 and 192 can be substantially free of the catalyst system. By "substantially free" it is meant that the ethylene feedstock mixture has equal to or less than 1.0, 0.9, 0.8, 0.7, 0.6, 0.5, 0.4, 0.3, 0.2, or 0.1 wt. % of the catalyst system present based on the total weight of the catalyst system entering the reaction zone 110.

FIG. 2 shows a process flow diagram of another reaction system 200 according to the present disclosure. The system 200 includes one or more of an ethylene source 140 in fluid communication with an ethylene feed line 142; a catalyst system source 150 in fluid communication with a catalyst system feed line 152; an organic reaction medium source 160 in fluid communication with an organic reaction medium feed line 162; an optional scrub agent source 170 in communication with a scrub agent feed line 172; an optional hydrogen feed line 144 feeding to the ethylene feed line 142; an optional pump 180; an optional mixing device 190; a reaction zone 110 having a reaction zone inlet 119 representing one or more reaction zone inlets and a reaction zone outlet 117 representing one or more reaction zone outlets; and a heat exchanger 120. It is contemplated that reaction system 200 of FIG. 2 can include appropriate equipment (e.g., valves, control devices, sensors, electrical writing, insulation) which are not shown in FIG. 2 yet would be included according to those skilled in the art with the aid of this disclosure.

The reaction zone inlet 119 (representing one or more reaction zone inlets) can be configured to introduce the catalyst system and the ethylene feedstock mixture to the reaction zone 110, and the reaction zone outlet 117 (representing one or more reaction zone outlets) is configured to discharge a reaction zone effluent comprising an oligomer product from the reaction zone 110 via line 118. Reaction zone effluent in line 118 can then feed to equipment (not shown) for isolating various streams (e.g., the desired oligomer) from the reaction zone effluent. Valve 130 can be used in line 118 to control a flow of the reaction zone effluent in line 118 and/or to control a pressure of the reaction zone 110.

In FIG. 2, the ethylene feedstock mixture, the catalyst system, and optionally, hydrogen can be periodically or continuously introduced to the reaction zone 110. Moreover, the reaction zone effluent can be periodically or continuously removed from the reaction zone 110. For example, the reaction zone inlet 119 can be configured to periodically or continuously introduce a combined feed line 193 comprising the catalyst system, the ethylene feedstock mixture, and optionally hydrogen to the reaction zone 110, and the reaction zone outlet 117 (representing one or more reaction zone outlets) can be configured to periodically or continuously discharge or remove the reaction zone effluent comprising oligomer product from the reaction zone 110.

The catalyst system can flow through catalyst system feed line 152 from the catalyst system source 150 to combine with an ethylene feedstock mixture (which can have the ethylene an organic reaction medium optionally dispersed using optional mixing device 190) in line 192. The catalyst system feed line 152 can optionally include a solvent and/or a diluent along with the catalyst system. The solvent and/or the diluent can be an organic reaction medium. In some embodiments, the solvent and/or diluent can be the organic reaction medium used in the ethylene feedstock mixture. The catalyst system can be dispersed in the solvent and/or the diluent in the catalyst system feed line 152. For example, the catalyst system feed line 152 can include a mixing device (not shown), similar to mixing device 190 (described herein) or a precontactor apparatus (not shown), which is configured to disperse the catalyst system in the solvent and/or the diluent prior to the catalyst system combining with the dispersed ethylene feed stock mixture in line 192. When solvent and/or diluent and the catalyst system are present in the catalyst system feed line 152 in FIG. 2, the chromium:solvent and/or diluent mass ratio can be any disclosed herein.

Optionally, scrub agent (described herein) can flow in the scrub agent feed line 172. In some embodiments, the scrub agent may not be the aluminoxane of the catalyst system.

Organic reaction medium can flow in organic reaction medium feed line 162 from the organic reaction medium source 160 to the suction side 181 of pump 180.

Similar to the system 100 of FIG. 1, at least a portion of the organic reaction medium in the system 200 of FIG. 2 can be contacted with a scrub agent (e.g., an alkylaluminum compound, any described herein) prior to introduction of the portion of the organic reaction medium to the reaction zone 110. FIG. 2 shows scrub agent can be added via feed line 172 to the organic reaction medium feed line 162 such that the organic reaction medium feed line 162 can contain both the organic reaction medium and the scrub agent.

Likewise, similar to the system 100 of FIG. 1, at least a portion of the organic reaction medium in the system 200 of FIG. 2 can be contacted with the scrub agent (e.g., an alkylaluminum compound, any described herein) prior to contact of the portion of organic reaction medium with ethylene. Alternatively (not shown), the at least a portion of the organic reaction medium in the system 200 of FIG. 2 can be contacted with the scrub agent (e.g., an alkylaluminum compound) prior to contact of the portion of organic reaction medium in the ethylene feedstock mixture with the catalyst system. FIG. 2 shows the scrub agent can be added via line 172 to the organic reaction medium feed line 162, before the organic reaction medium contacts ethylene via combination of the organic reaction medium feed line 162 with the ethylene feed line 142. The scrub agent is independently disclosed herein and can be utilized to further described reaction system 200.

In FIG. 2, all of the organic reaction medium can be fed to the reaction zone via line 162. However, as is discussed herein, it is contemplated that only a portion of the total amount of organic reaction medium which is used in the system 200 is in line 162 and optionally contacted with the scrub agent prior to introduction to the reaction zone 110; e.g., the other portions can be mixed with the catalyst system in catalyst system feed line 152 and/or can be included in a bypass line which can feed directly to the reaction zone 110. Alternatively, the scrub agent may not be combined with the organic reaction medium, and the organic reaction medium feed line 162 can flow directly to the suction side 181 of pump 180.

Ethylene can flow in ethylene feed line 142 from the ethylene source 140 and can combine with organic reaction medium (which optionally can be previously combined with scrub agent) flowing in line 162 on the head side 182 of the pump 180. Alternatively, ethylene can be combined with the organic reaction medium (and any optional scrub agent) flowing in line 162 on the suction side 181 of the pump 180.

Combination of the ethylene in line 142 with the organic reaction medium in line 162 yields an ethylene feedstock mixture in ethylene feedstock mixture line 191. The ethylene feedstock mixture can flow through an optional mixing device 190 where ethylene and the organic reaction medium (which optionally can be previously combined with scrub agent) can be dispersed, and subsequently flow as a dispersed ethylene feedstock mixture in dispersed ethylene feedstock mixture line 192.

The ethylene feedstock mixture can be contacted with the catalyst system prior to introduction of the ethylene feedstock mixture into the reaction zone 110. In FIG. 2, the ethylene feedstock mixture in the form of optionally dispersed ethylene feedstock mixture in line 192 can combine with the catalyst system in line 152 to form a combined feed line 193 which can flow to the reaction zone inlet 119 and can feed to the reaction zone 110. Alternatively, the scrub agent can be contacted with the ethylene feedstock mixture via combination with line 191, pass through the optional mixing device 190, and then contact the catalyst system.

Hydrogen optionally can be used to control the ethylene oligomerization reaction. The optional hydrogen can be fed into the ethylene feed line 142 of reaction system 200 via hydrogen feed line 144. The combination of hydrogen with ethylene in the ethylene feed line 144 can be upstream of valve 143 as shown in FIG. 2; or alternatively, downstream of valve 143. While the hydrogen feed line 144 in FIG. 2 is shown as feeding to the ethylene feed line 142, it is contemplated that the hydrogen feed line 144 can fluidly connect to the reaction zone inlet 119 via another line (e.g., line 152, line 162, line 172, line 191, line 192, or line 193).

Reaction zone 110 is shown in FIG. 2 as a single continuous stirred-tank reactor operating in continuous mode. Various alternative reactors, reactor configurations, and operating modes that can achieve similar ethylene oligomerization results are contemplated for the reaction zone 110 and are discussed in more detail herein. Thermocouple 114 can read the temperature of the reaction zone 110 as the reaction proceeds. Stirrer 116 operated by motor 112 can agitate the contents of the reaction zone 110. The stirrer can be an impeller coupled to the motor 112 via a rod. Heat exchanger 120 receives line 122 and provides line 124 to the reaction zone 110 in order to maintain a temperature of the reaction zone 110.

A reaction zone effluent comprising oligomer product formed in the reaction zone 110 flows in line 118 from reaction zone outlet 117. In some embodiments, the oligomer product in line 118 can flow to the product recovery zone (not shown). The product recovery zone can include catalyst system deactivation, oligomer product separation where the oligomer product (e.g., hexenes and/or octenes) can be recovered from the reaction zone effluent via techniques known in the art with the aid of this disclosure (e.g., distillation, flashing, absorption, stripping), by-product separation and/or isolation, and/or any steps which can facilitate the handling of the reaction zone effluent and the isolation of the desired ethylene oligomers.

Figure 3:
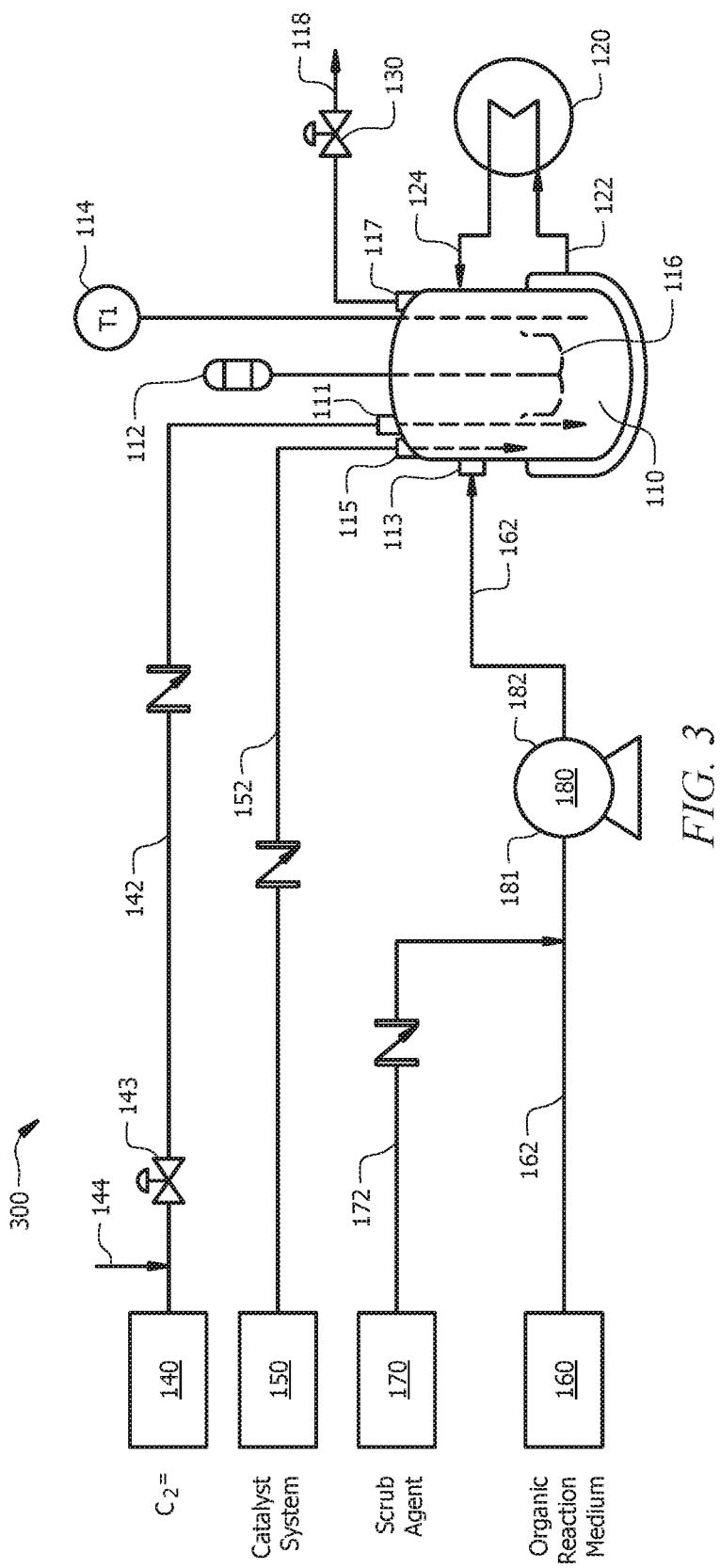
FIG. 3 shows a process flow diagram the reaction system used in Example 1.

FIG. 3 shows a reaction system 300 which was used for comparative Example 1. The components of system 300 which have like numerals designate the same components discussed for the system 100 in FIG. 1 and system 200 in FIG. 2. The configuration of feeding the catalyst system and ethylene to the reaction zone 110 of system 300 differs from system 100 and system 200. In system 300, ethylene flows in ethylene feed line 142 directly to the first reaction zone inlet 111, and the catalyst system flows in catalyst system feed line 152 to a third reaction zone inlet 115 (the second reaction zone inlet 113 receiving the organic reaction medium via line 162). Neither the catalyst system nor ethylene is combined with the organic reaction medium prior to feeding to the reaction zone 110 in system 300.

Figure 4:
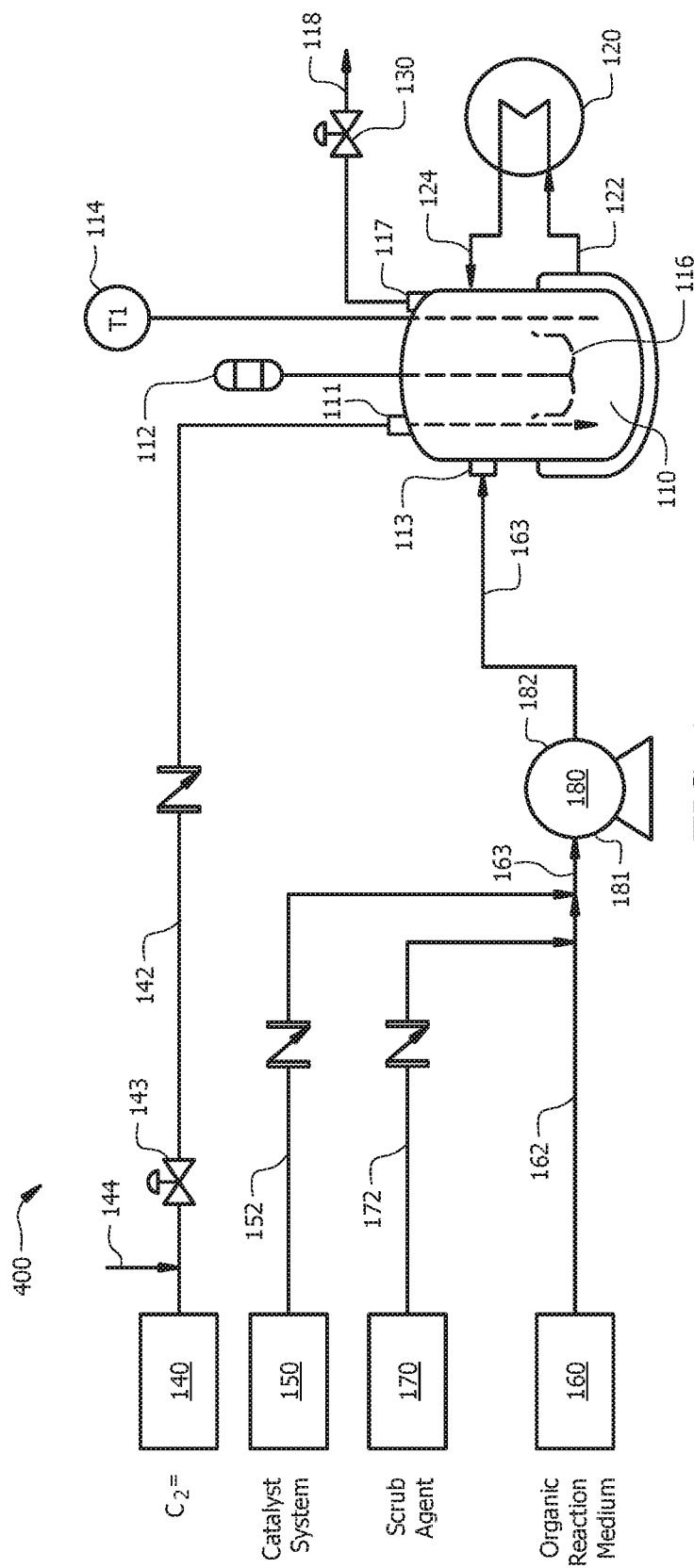
FIG. 4 shows a process flow diagram of the reaction system used in Example 2.

FIG. 4 shows a reaction system 400 which was used for comparative Example 2. The components of system 400 which have like numerals designate the same components discussed for the system 100 in FIG. 1 and system 200 in FIG. 2. The configuration of feeding the catalyst system and ethylene to the reaction zone 110 of system 400 differs from system 100 and system 200. In system 400, ethylene flows in ethylene feed line 142 directly to the first reaction zone inlet 111, and the catalyst system flows in catalyst system feed line 152 to combine with the organic reaction medium feed line 162 (containing the organic reaction medium optionally combined with scrub agent) to yield line 163. The combined mixture of organic reaction medium, catalyst system, and optional scrub agent flows in line 163 to the suction side 181 of pump 180. The pump 180 sends the combined mixture via line 163 to the second reaction zone inlet 113 and into the reaction zone 110. The catalyst system in system 400 is thus diluted with organic reaction medium prior to entering the reaction zone 110, while ethylene is not combined with the organic reaction medium or otherwise diluted prior to feeding to the reaction zone 110.

The reaction zone of any process, system and/or reaction system (e.g., reaction zone 110 of the figures) can comprise any reactor which can oligomerize ethylene to an oligomer product. In an embodiment, the reaction zone of any process, system, or reaction system described herein can comprise a stirred tank reactor, a plug flow reactor, or any combination thereof; alternatively, a stirred tank reactor; or alternatively, a plug flow reactor. In an embodiment, the reaction zone of any process, system, or reaction system described herein can comprise an autoclave reactor, continuous stirred tank reactor, a loop reactor, a gas phase reactor, a solution reactor, a tubular reactor, a recycle reactor, a bubble reactor, or any combination thereof; alternatively, autoclave reactor; alternatively, stirred tank reactor; alternatively, a loop reactor; alternatively, a gas phase reactor; alternatively, a solution reactor; alternatively, a tubular reactor; alternatively, a recycle reactor; or alternatively, a bubble reactor. In some embodiments, the reaction zone can comprise multiple reactor; or alternatively, only on reactor. When multiple reactors are present, each of the reactors can be the same or different types of reactors. The reaction zone (e.g., reaction zone 110) can comprise single or multiple reactors of any of the types disclosed herein operating in batch or continuous mode; or alternatively, in continuous mode.

Aspects and/or embodiments of the processes, systems, and/or reaction systems described herein can utilize a pump. In an embodiment, the pump can be any pump which can pump the organic reaction medium to the reaction zone. Generally, the pump can have a suction side which receives the organic reaction medium and a head side which provides the organic reaction medium at a pressure suitable for flow to the reaction zone. FIG. 1, FIG. 2, and FIG. 4 provide non-liming examples of reaction systems which can utilize a pump 180 having suction side 181 and head side 182. In FIG. 1, pump 180 is in fluid communication with the second reaction zone inlet 113. In FIG. 2, pump 180 is in fluid communication with the reaction zone inlet 119. FIG. 1 and FIG. 2 show that pump 180 can be located upstream of the point where ethylene (e.g., from the ethylene feed line 142) and the organic reaction medium (e.g., from the organic reaction medium feed line 162 which optionally contains scrub agent and/or catalyst system) join/combine to form the ethylene feedstock mixture. Feeding ethylene in this configuration can reduce flashing and recompression. In an embodiment, the pump 180 can be configured to receive the catalyst system and/or the scrub agent combined with the organic reaction medium on the suction side 181 of the pump 180; alternatively, the catalyst system and/or the scrub agent can be combined with the organic reaction medium on the head side 182 of the pump 180; alternatively, the catalyst system can be combined with the organic reaction medium on the suction side 181 of the pump 180 while the scrub agent can be combined with the organic reaction medium and catalyst system on the head side 182 of the pump; alternatively, the scrub agent can be combined with the organic reaction medium on the suction side 181 of the pump 180 while the catalyst system can be combined with the organic reaction medium and scrub agent on the head side 182 of the pump 180. In the system 400 in FIG. 4, pump 180 can be configured to receive the catalyst system combined with the organic reaction medium on the suction side 181 and to pump the catalyst system combined with the organic reaction medium and optional scrub agent on the head side 182 of the pump 180.

In configurations where the reaction zone 110 has a recycle features, a pump can be included in the path of the reaction zone 110 suitable for passing contents of the reaction zone 110 to heat exchangers. For example a pump suitable for pumping reaction zone contents can be placed in line 122 of FIG. 1 or FIG. 2 to pass the contents to the heat exchanger 120.

Aspects and/or embodiments of the processes, systems, and/or reaction systems described herein can utilize a mixing device to mix/disperse the ethylene and the organic reaction medium. In an embodiment, the mixing device can be any device which can mix/disperse the organic reaction medium and ethylene in the ethylene feedstock mixture. Such mixing/dispersing can be implemented to minimize areas of high ethylene concentration within the ethylene feedstock mixture. The mixing device can provide mixing of ethylene and the organic reaction medium via agitation of the flow there through. For example, the mixing device can be a static mixer having fixed baffles (e.g., in a helical arrangement, or any other baffle arrangement) placed within a housing, where the baffles continuously blend the ethylene and organic reaction medium to disperse the ethylene and the organic reaction medium in the ethylene feedstock mixture. Alternatively, the mixing device can have moving parts such as a propeller or impeller. FIG. 1 shows an optional mixing device 190 that can be positioned between i) the joining of the ethylene feed line 142 and the organic reaction medium feed line 162 and ii) the second reaction zone inlet 113 such that ethylene and the organic reaction medium are dispersed in the ethylene feedstock mixture prior to the ethylene feedstock mixture entering the reaction zone 110. FIG. 2 shows an optional mixing device 190 that can be positioned between i) the joining of the ethylene feed line 142 and the organic reaction medium feed line 162 and ii) the reaction zone inlet 119 such that ethylene and the organic reaction medium are dispersed in the ethylene feedstock mixture prior to the ethylene feedstock combining with the catalyst system and prior to the ethylene feedstock mixture entering the reaction zone 110. In some embodiment the mixing or dispersion of the ethylene and the organic reaction medium can be accomplished used a precontactor device such a vessel with a mixing device.

Lines 118, 122, 124, 142, 152, 162, 163, 172, 191, 192, and 193 shown in the figures can be appropriate metal piping or tubing for the ethylene oligomerization reaction system components.

The reaction zone inlets 111, 113, 115, and 119, as well as the reaction zone outlet 117, shown in the figures can be in the form of flanges and/or appropriate piping and valves for receiving the various feed components and removing the reaction zone effluent from the reaction zone 110. The reaction zone outlet 117 can be one or more physical outlets. For example, the reaction zone 110 shown in FIG. 1 and FIG. 2 can have one outlet 117; alternatively, the reaction zone 110 can have one or more other outlets in addition to outlet 117; alternatively, the reaction zone 110 can include multiple reactors, each having a single outlet or multiple outlets which amount to more than one outlet for the collection of multiple reactors which define the reaction zone 110. Additionally, each reaction zone inlet which is shown as a single reaction zone inlet can represent one or more reaction inlets feeding the designated materials to the reaction zone.

Ethylene for any of the processes, systems, and/or reaction systems described herein (e.g., ethylene source 140) can be oligomerization or polymerization grade ethylene. By "oligomerization or polymerization grade ethylene" it is meant that ethylene can be present in ethylene feed line 142 in an amount of at least 98.0, 98.5, 99.0, 99.1, 99.2, 99.3, 99.4, 99.5, 99.6, 99.7, 99.8, 99.9, 99.99, 99.999 mol % based on the total moles of components in the ethylene composition (e.g., in the ethylene feed line 142). The ethylene for any of the processes, systems, and/or reaction systems (e.g., ethylene source 140) can be any source of oligomerization or polymerization grade ethylene, for example, a storage tank or a line from a cracking process, monomer recovery process, and the like. In an embodiment of the processes, systems, and/or reaction systems (e.g., reaction systems 100 and 200) disclosed herein, substantially all of the ethylene can be contacted with the catalyst system and/or contacted with the catalyst system and/or introduced/fed to the reaction zone (e.g., reaction zone 110) via the ethylene feedstock mixture. By "substantially all" it is meant that at least 95, 97, 99, 99.5, 99.75, or 99.9 mol % of the total ethylene used in the processes, systems, and/or reaction systems (e.g., reaction systems system 100 or 200) described herein can be introduced/fed to the reaction zone via the ethylene feedstock mixture.

The processes, systems, and/or reaction systems described herein can use an organic reaction medium. Generally, the organic reaction can act as a solvent or a diluent in the processes described herein. In an aspect, the organic reaction medium can be a hydrocarbon, a halogenated hydrocarbon, or a combination thereof, for example. Hydrocarbons and halogenated hydrocarbons which can be used as an organic reaction medium can include, for example, aliphatic hydrocarbons, aromatic hydrocarbons, petroleum distillates, halogenated aliphatic hydrocarbons, halogenated aromatic hydrocarbons, or combinations thereof. Aliphatic hydrocarbons which can be useful as an organic reaction medium include $C_3$ to $C_{20}$ aliphatic hydrocarbons, or $C_4$ to $C_{15}$ aliphatic hydrocarbons, or $C_5$ to $C_{10}$ aliphatic hydrocarbons, for example. The aliphatic hydrocarbons which can be used as an organic reaction medium can be cyclic or acyclic and/or can be linear or branched, unless otherwise specified. Non-limiting examples of suitable acyclic aliphatic hydrocarbon organic reaction mediums that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), or combinations thereof. Non-limiting examples of suitable cyclic aliphatic hydrocarbons which can be used as an organic reaction medium include cyclohexane, and methyl cyclohexane, for example. Aromatic hydrocarbons which can be useful as an organic reaction medium include $C_6$ to $C_{10}$ aromatic hydrocarbons. Non-limiting examples of suitable aromatic hydrocarbons that can be utilized singly or in any combination as an organic reaction medium include benzene, toluene, xylene (including ortho-xylene, meta-xylene, para-xylene, or mixtures thereof), ethylbenzene, or combinations thereof. Halogenated aliphatic hydrocarbons which can be useful as an organic reaction medium include $C_1$ to $C_{15}$ halogenated aliphatic hydrocarbons, $C_1$ to $C_{10}$ halogenated aliphatic hydrocarbons, or $C_1$ to $C_5$ halogenated aliphatic hydrocarbons, for example. The halogenated aliphatic hydrocarbons which can be used as an organic reaction medium can be cyclic or acyclic and/or can be linear or branched, unless otherwise specified. Non-limiting examples of suitable halogenated aliphatic hydrocarbons which can be utilized as an organic reaction medium include methylene chloride, chloroform, carbon tetrachloride, dichloroethane, trichloroethane, and combinations thereof. Halogenated aromatic hydrocarbons which can be useful as an organic reaction medium include $C_6$ to $C_{20}$ halogenated aromatic hydrocarbons, or $C_6$ to $C_{10}$ halogenated aromatic hydrocarbons, for example. Non-limiting examples of suitable halogenated aromatic hydrocarbons which can be used as a solvent include chlorobenzene, dichlorobenzene, or combinations thereof, for example.

The choice of organic reaction medium can be made on the basis of convenience in processing. For example, isobutane can be chosen to be compatible with solvents and diluents used in processes using the product(s) of the process described herein (e.g., using the product for the formation of polymer in a subsequent processing step). In some embodiments, the organic reaction medium can be chosen to be easily separable from the one or more of the oligomer in the oligomer product. In some embodiments, an oligomer of the oligomer product can be utilized as the reaction system solvent. For example, when 1-hexene is an oligomer of an ethylene trimerization process, 1-hexene can be chosen as the reaction system solvent to decrease the need for separation.

The organic reaction medium source (e.g., organic reaction medium source 160) can be any source for including a storage tank of the organic reaction medium and/or any line from an oligomerization process, a polymerization process, monomer recovery process, and the like.

While in FIG. 1 and FIG. 2 the entire supply of organic reaction medium is shown flowing in line 162 from the organic reaction medium source 160 to the reaction zone 110, it is contemplated that only a portion of the total amount of organic reaction medium used in system 100 and 200 flows in line 162, and that a bypass line can be alternatively utilized to flow another portion of the organic reaction medium (e.g., a portion which is not combined with any other reaction component) directly to the reaction zone 110 and in parallel flow to line 162. Additionally or alternatively, a portion of the total amount of organic reaction medium in the system 100 or 200 can be utilized in the catalyst system feed line 152. That is, a portion of the organic reaction medium can be used to dilute or act as a carrying fluid for the catalyst system in catalyst system feed line 152.

As described herein, aspects and embodiments of the herein disclosed processes, systems, and/or reaction systems can include combining ethylene and organic reaction medium to form an ethylene feedstock mixture. The minimum ethylene concentration in the ethylene feedstock mixture can be 4 mass %, 10 mass %, 25 mass %, 35 mass %, or 40 mass % based upon the total mass in the ethylene feedstock mixture; alternatively or additionally, at a maximum ethylene concentration of the ethylene feedstock mixture cam be 65 mass %, 60 mass %, 55 mass %, 50 mass %, 48 mass % based upon the total mass in the ethylene feedstock mixture. In an embodiment, ethylene concentration in the ethylene feedstock mixture can from any minimum ethylene concentration in the ethylene feedstock mixture disclosed herein to any maximum ethylene concentration in the ethylene feedstock mixture disclosed herein. In some non-limiting embodiments, the ethylene concentration in the ethylene feedstock mixture can be in a range of from 4 mass % to 60 mass %, from 10 mass % to 60 mass %, from 25 mass % to 55 mass %, 35 mass % to 50 mass %, or 40 mass % to 48 mass % based upon the total mass in the ethylene feedstock mixture. Other ethylene concentrations in the ethylene feedstock mixture ranges that can be utilized are readily apparent to those skilled in the art with the aid of this disclosure.

Aspects and embodiments of the herein described processes, systems, and/or reaction process can utilize a catalyst system comprising i) a chromium component comprising an $N^2$-phosphinyl formamidine chromium compound complex, an $N^2$-phosphinyl amidine chromium compound complex, an $N^2$-phosphinyl guanidine chromium compound complex, or any combination thereof, and ii) an aluminoxane. In some embodiments, the catalyst system can comprise i) a chromium component comprising an $N^2$-phosphinyl formamidine chromium compound complex and ii) an aluminoxane; alternatively, i) a chromium component comprising an $N^2$-phosphinyl amidine chromium compound complex and ii) an aluminoxane; or alternatively, i) a chromium component comprising an $N^2$-phosphinyl guanidine chromium compound complex and ii) an aluminoxane. Generally, the $N^2$-phosphinyl amidine chromium compound complex, the $N^2$-phosphinyl formamidine chromium compound complex, the $N^2$-phosphinyl guanidine chromium compound complex, the aluminoxane, and any other element of the catalyst system described herein are independent elements of the catalyst systems. These catalyst system elements are independently described herein and can be utilized without limitation, and in any combination, to further describe a catalyst system utilized in aspects and/or embodiments of the processes, systems, and/or reaction systems described herein.

In an embodiment, the $N^2$-phosphinyl formamidine chromium compound complex utilized in the catalyst systems described herein can comprise, can consist essentially of, or can be, an $N^2$-phosphinyl formamidine chromium compound complex having the Structure NPFCr1. In an embodiment, the $N^2$-phosphinyl amidine chromium compound complex utilized in the catalyst systems described herein can comprise, can consist essentially of, of can be, an $N^2$-phosphinyl amidine chromium compound complex having the Structure NPACr1. In an embodiment, the $N^2$-phosphinyl guanidine chromium compound complex utilized in the catalyst systems described herein can comprise, can consist essentially of, or can be, an $N^2$-phosphinyl guanidine chromium compound complex having the Structure GuCr1, GuCr2, GuCr3, GuCr4, or GuCr5; alternatively, alternatively, an $N^2$-phosphinyl guanidine chromium compound complex having the Structure GuCr1; alternatively, an $N^2$-phosphinyl guanidine chromium compound complex having the Structure GuCr2; alternatively, an $N^2$-phosphinyl guanidine chromium compound complex having the Structure GuCr3; alternatively, an $N^2$-phosphinyl guanidine chromium compound complex having the Structure GuCr4; or alternatively, an $N^2$-phosphinyl guanidine chromium compound complex having the Structure GuCr5.

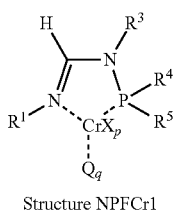

Structure NPFCr1

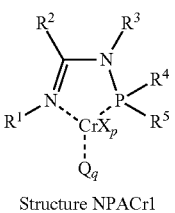

Structure NPACr1

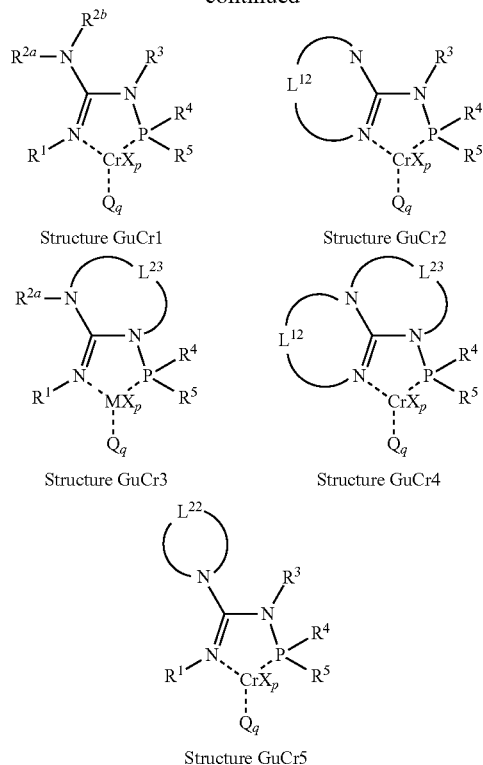

Within the $N^2$-phosphinyl formamidine chromium compound complexes and the $N^2$-phosphinyl amidine chromium compound complexes, the nitrogen participating in a double bond with the central carbon atom is referred to as the $N^1$ nitrogen and the nitrogen atom participating in a single bond with the central carbon atom is referred to as the $N^2$ nitrogen. Similarly, within the $N^2$-phosphinyl guanidine chromium compound complexes, the nitrogen participating in a double bond with the central carbon atom of the guanidine core is referred to as the $N^1$ nitrogen, the nitrogen atom participating in a single bond with the central carbon atom of the guanidine core and a bond with the phosphorus atom of the phosphinyl group is referred to as the $N^2$ nitrogen, and the remaining nitrogen atom participating in a single bond with the central carbon atom of the guanidine core is referred to as the $N^3$ nitrogen. It should be noted that the guanidine group of the guanidine in the $N^2$-phosphinyl guanidine transition metal complexes can be a portion of a larger group which does not contain guanidine in it name. For example, while the compound 7-dimethylphosphinylimidazo[1,2-a] imidazole could be classified as a compound having an imidazo[1,2-a]imidazole core (or a compound having a phosphinylimidazo imidazole group), 7-dimethylphosphinylimidazo[1,2-a]imidazole would still be classified as a compound having a guanidine core (or as a compound having an guanidine group) since it contains the defined general structure of the guanidine compound.

$R^1$, $R^3$, $R^4$, and $R^5$ within the $N^2$-phosphinyl formamidine chromium compound complexes having Structure NPFCr1, the $N^2$-phosphinyl amidine chromium compound complexes having Structure NPACr1, and the $N^2$-phosphinyl guanidine chromium compound complexes having the Structures GuCr1, GuCr2, GuCr3, GuCr4, and/or GuCr5 are independently described herein and can be utilized without limitation to further describe the $N^2$-phosphinyl formamidine chromium compound complexes having Structure NPFCr1, the $N^2$-phosphinyl amidine chromium compound complexes having Structure NPACr1, and/or the $N^2$-phosphinyl guanidine chromium compound complexes having the Structures GuCr1, GuCr2, GuCr3, GuCr4, and/or GuCr5. Similarly, $R^2$ within the $N^2$-phosphinyl amidine chromium compound complexes having Structure NPACr1 are independently described herein and can be utilized without limitation to further describe the $N^2$-phosphinyl amidine chromium compound complexes having Structure NPACr1. Similarly, $R^{2a}$, $R^{2b}$, $L^{12}$, $L^{22}$, and $L^{23}$ within the $N^2$-phosphinyl guanidine chromium compound complexes having the Structures GuCr1, GuCr2, GuCr3, GuCr4, or GuCr5 are independently described herein and can be utilized without limitation to further describe the $N^2$-phosphinyl guanidine chromium compound complexes having the Structures GuCr1, GuCr2, GuCr3, GuCr4, and/or GuCr5. $MX_p$, Q, and q of the $N^2$-phosphinyl formamidine chromium compound complexes, the $N^2$-phosphinyl amidine chromium compound complexes, and the $N^2$-phosphinyl guanidine chromium compound complexes are independently described herein and can be utilized in any combination, and without limitation, to further describe the $N^2$-phosphinyl formamidine chromium compound complexes, the $N^2$-phosphinyl amidine chromium compound complexes, the $N^2$-phosphinyl guanidine chromium compound complexes. Additionally, $MX_p$, Q, and q can be combined, without limitation, with the independently described $R^1$, $R^2$, $R^{2a}$, $R^{2b}$, $R^3$, $R^4$, $R^5$, $L^{12}$, $L^{22}$, and $L^{23}$ to further describe the appropriate $N^2$-phosphinyl formamidine chromium compound complexes, the $N^2$-phosphinyl amidine chromium compound complexes, and the $N^2$-phosphinyl guanidine chromium compound complexes described herein which have an $R^1$, $R^2$, $R^{2a}$, $R^{2b}$, $R^3$, $R^4$, $R^5$, $L^{12}$, $L^{22}$, and/or $L^{23}$.

Generally, $R^1$ of the $N^2$-phosphinyl formamidine chromium compound complexes, the $N^2$-phosphinyl amidine chromium compound complexes, and/or the $N^2$-phosphinyl guanidine chromium compound complexes which have an $R^1$ group can be an organyl group; alternatively, an organyl group consisting essentially of inert functional groups; or alternatively, a hydrocarbyl group. In an embodiment, the $R^1$ organyl group of the $N^2$-phosphinyl formamidine chromium compound complexes, the $N^2$-phosphinyl amidine chromium compound complexes, and/or the $N^2$-phosphinyl guanidine chromium compound complexes, which have an $R^1$ group, can be a $C_1$ to $C_{20}$, a $C_1$ to $C_{15}$, a $C_1$ to $C_{10}$, or a $C_1$ to $C_5$ organyl group. In an embodiment, the $R^1$ organyl group consisting essentially of inert functional groups of the $N^2$-phosphinyl formamidine chromium compound complexes, the $N^2$-phosphinyl amidine chromium compound complexes, and/or the $N^2$-phosphinyl guanidine chromium compound complexes, which have an $R^1$ group, can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, the $R^1$ hydrocarbyl group of the $N^2$-phosphinyl formamidine chromium compound complexes, the $N^2$-phosphinyl amidine chromium compound complexes, and/or the $N^2$-phosphinyl guanidine chromium compound complexes, which have an $R^1$ group, can be a $C_1$ to $C_{20}$, a $C_1$ to $C_{15}$, a $C_1$ to $C_{10}$, or a $C_1$ to $C_5$ hydrocarbyl group.

In an embodiment, $R^1$ of the $N^2$-phosphinyl formamidine chromium compound complexes, the $N^2$-phosphinyl amidine chromium compound complexes, and/or the $N^2$-phosphinyl guanidine chromium compound complexes which have an $R^1$ group can be an alkyl group, a substituted alkyl group, a cycloalkyl group, a substituted cycloalkyl group, an aryl group, a substituted aryl group, an aralkyl group, or a substituted aralkyl group. In some embodiments, $R^1$ of the $N^2$-phosphinyl formamidine chromium compound complexes, the $N^2$-phosphinyl amidine chromium compound complexes, and/or the $N^2$-phosphinyl guanidine chromium compound complexes which have an $R^1$ group can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^1$ of the $N^2$-phosphinyl formamidine chromium compound complexes, the $N^2$-phosphinyl amidine chromium compound complexes, and/or the $N^2$-phosphinyl guanidine chromium compound complexes which have an $R^1$ group can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, the alkyl group which can be utilized as $R^1$ can be a $C_1$ to $C_{20}$, a $C_1$ to $C_{10}$, or a $C_1$ to $C_5$ alkyl group. In any aspect or embodiment disclosed herein, the substituted alkyl group which can be utilized as $R^1$ can be a $C_1$ to $C_{20}$, a $C_1$ to $C_{10}$, or a $C_1$ to $C_5$ substituted alkyl group. In any aspect or embodiment disclosed herein, the cycloalkyl group which can be utilized as $R^1$ can be a $C_4$ to $C_{20}$, a $C_4$ to $C_{15}$, or a $C_4$ to $C_{10}$ cycloalkyl group. In any aspect or embodiment disclosed herein, the substituted cycloalkyl group which can be utilized as $R^1$ can be a $C_4$ to $C_{20}$, a $C_4$ to $C_{15}$, or a $C_4$ to $C_{10}$ substituted cycloalkyl group. In any aspect or embodiment disclosed herein, the aryl group which can be utilized as $R^1$ can be a $C_6$ to $C_{20}$, a $C_6$ to $C_{15}$, or a $C_6$ to $C_{10}$ aryl group. In any aspect or embodiment disclosed herein, the substituted aryl group which can be utilized as $R^1$ can be a $C_6$ to $C_{20}$, a $C_6$ to $C_{15}$, or a $C_6$ to $C_{10}$ substituted aryl group. In any aspect or embodiment disclosed herein, the aralkyl group which can be utilized as $R^1$ can be a $C_7$ to $C_{20}$, a $C_7$ to $C_{15}$, or a $C_7$ to $C_{10}$ aralkyl group. In any aspect or embodiment disclosed herein, the substituted aralkyl group which can be utilized as $R^1$ can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^1$.

In an embodiment, $R^1$ can be a methyl group, an ethyl group, a propyl group, a butyl group, a pentyl group, a hexyl group, a heptyl group, or an octyl group. In some embodiments, one or more of $R^1$ can be a methyl group, an ethyl group, a n-propyl (1-propyl) group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl)

group; alternatively, a tert-butyl (2-methyl-2-propyl) group; or alternatively, a neopentyl (2,2-dimethyl-1-propyl) group. In some embodiments, the alkyl groups which can be utilized as $R^1$ can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as $R^1$.

In an embodiment, $R^1$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an embodiment, the substituted cycloalkyl group, which can be utilized as $R^1$, can be a 2-substituted cyclohexyl group, a 2,6-disubstituted cyclohexyl group, a 2-substituted cyclopentyl group, or a 2,6-disubstituted cyclopentyl group; alternatively, a 2-substituted cyclohexyl group or a 2,6-disubstituted cyclohexyl group; alternatively, a 2-substituted cyclopentyl group or a 2,6-disubstituted cyclopentyl group; alternatively, a 2-substituted cyclohexyl group or a 2-substituted cyclopentyl group; alternatively, a 2,6-disubstituted cyclohexyl group or a 2,6-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,6-disubstituted cyclopentyl group. In an embodiment, one or more substituents of a multi-substituted cycloalkyl group utilized as $R^1$ can be the same or different; alternatively, all the substituents of a multi-substituted cycloalkyl group can be the same; or alternatively, all the substituents of a multi-substituted cycloalkyl group can be different. Each substituent of a substituted cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy (general and specific) groups are independently disclosed herein. These substituent halogens, substituent hydrocarbyl groups, and substituent hydrocarboxy groups can be utilized without limitation to further describe a substituted cycloalkyl group (general or specific) which can be utilized as $R^1$.

In a non-limiting embodiment, $R^1$ can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, or a 2,5-dialkylcyclopentyl group. Alkyl substituent groups (general and specific) are independently described herein and these alkyl substituent groups can be utilized, without limitation, to further describe alkylcyclohexyl groups (general and specific), dialkylcyclohexyl groups (general and specific), alkylcyclopentyl groups (general or specific), and/or dialkylcyclopentyl groups (general and specific) which can be utilized as $R^1$. Generally, the alkyl substituents of a dialkylcyclohexyl group or a dialkylcyclopentyl group can be the same; or alternatively, the alkyl substituents of a dialkylcyclohexyl group or a dialkylcyclopentyl group can be different. In some non-limiting embodiments, any one or more of $R^1$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting embodiments, one or more of $R^1$ can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an embodiment, $R^1$ can be a phenyl group, a substituted phenyl group; alternatively, a phenyl group; or alternatively, a substituted phenyl group. In an embodiment, the substituted phenyl group, which can be utilized as $R^1$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an embodiment, one or more substituents of a multi-substituted phenyl group utilized as $R^1$ can be the same or different; alternatively, all the substituents of a multi-substituted cycloalkyl group can be the same; or alternatively, all the substituents of a multi-substituted cycloalkyl group different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^1$.

In a non-limiting embodiment, $R^1$ can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group;

alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^1$. Generally, the alkyl substituents of a dialkylphenyl group (general or specific) or a trialkylphenyl group (general or specific) can be the same; or alternatively, the alkyl substituents of a dialkylphenyl group or trialkylphenyl group can be different. In some non-limiting embodiments, one or more of $R^1$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In an embodiment, $R^1$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group (general or specific) which can be utilized as $R^1$.

Generally, $R^2$ of the $N^2$-phosphinyl amidine chromium compound complexes can be an organyl group; alternatively, an organyl group consisting essentially of inert functional groups; or alternatively, a hydrocarbyl group. In an embodiment, $R^2$ organyl group of the $N^2$-phosphinyl amidine chromium compound complexes can be a $C_1$ to $C_{20}$, a $C_1$ to $C_{15}$, a $C_1$ to $C_{10}$, or a $C_1$ to $C_5$ organyl group. In an embodiment, $R^2$ organyl group consisting essentially of inert functional groups of the $N^2$-phosphinyl amidine chromium compound complexes can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, $R^2$ hydrocarbyl group of the $N^2$-phosphinyl amidine chromium compound complexes can be a $C_1$ to $C_{20}$, a $C_1$ to $C_{15}$, a $C_1$ to $C_{10}$, or a $C_1$ to $C_5$ hydrocarbyl group.

In an embodiment, $R^2$ of the $N^2$-phosphinyl amidine chromium compound complexes can be an alkyl group, a substituted alkyl group, a cycloalkyl group, a substituted cycloalkyl group, an aryl group, a substituted aryl group, an aralkyl group, or a substituted aralkyl group. In some embodiments, $R^2$ of the $N^2$-phosphinyl amidine chromium compound complexes can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^2$ of the $N^2$-phosphinyl amidine chromium compound complexes can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, the alkyl group which can be utilized as $R^2$ can be a $C_1$ to $C_{20}$, a $C_1$ to $C_{10}$, or a $C_1$ to $C_5$ alkyl group. In any aspect or embodiment disclosed herein, the substituted alkyl group which can be utilized as $R^2$ can be a $C_1$ to $C_{20}$, a $C_1$ to $C_{10}$, or a $C_1$ to $C_5$ substituted alkyl group. In any aspect or embodiment disclosed herein, the cycloalkyl group which can be utilized as $R^2$ can be a $C_4$ to $C_{20}$, a $C_4$ to $C_{15}$, or a $C_4$ to $C_{10}$ cycloalkyl group. In any aspect or embodiment disclosed herein, the substituted cycloalkyl group which can be utilized as $R^2$ can be a $C_4$ to $C_{20}$, a $C_4$ to $C_{15}$, or a $C_4$ to $C_{10}$ substituted cycloalkyl group. In any aspect or embodiment disclosed herein, the aryl group which can be utilized as $R^2$ can be a $C_6$ to $C_{20}$, a $C_6$ to $C_{15}$, or a $C_6$ to $C_{10}$ aryl group. In any aspect or embodiment disclosed herein, the substituted aryl group which can be utilized as $R^2$ can be a $C_6$ to $C_{20}$, a $C_6$ to $C_{15}$, or a $C_6$ to $C_{10}$ substituted aryl group. In any aspect or embodiment disclosed herein, the aralkyl group which can be utilized as $R^2$ can be a $C_7$ to $C_{20}$, a $C_7$ to $C_{15}$, or a $C_7$ to $C_{10}$ aralkyl group. In any aspect or embodiment disclosed herein, the substituted aryl group which can be utilized as $R^2$ can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^2$.

In an embodiment, $R^2$ can be a methyl group, an ethyl group, a propyl group, a butyl group, a pentyl group, a hexyl group, a heptyl group, or an octyl group. In some embodiments, one or more of $R^2$ can be a methyl group, an ethyl group, an n-propyl (1-propyl) group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some embodiments, the alkyl groups which can be utilized as $R^2$ can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group (general or specific) which can be utilized as $R^2$.

In an embodiment, $R^2$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an embodiment, the substituted cycloalkyl group, which can be utilized as $R^2$, can be a 2-substituted cyclohexyl group, a 2,6-disubstituted cyclohexyl group, a 2-substituted cyclopentyl group, or a 2,6-disubstituted cyclopentyl group; alternatively, a 2-substituted cyclohexyl group or a 2,6-disubstituted cyclohexyl group; alternatively, a 2-substituted cyclopentyl group or a 2,6-disubstituted cyclopentyl group; alternatively, a 2-substituted cyclohexyl group or a 2-substituted cyclopentyl group; alternatively, a 2,6-disubstituted cyclohexyl group or a 2,6-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,6-disubstituted cyclopentyl group. In an embodiment, one or more substituents of a multi-substituted cycloalkyl group utilized as $R^2$ can be the same or different; alternatively, all the substituents of a multi-substituted cycloalkyl group can be the same; or alternatively, all the substituents of a multi-substituted cycloalkyl group can be different. Each substituent of a cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^2$.

In a non-limiting embodiment, $R^2$ can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^2$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting embodiments, any one or more of $R^2$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting embodiments, one or more of $R^2$ can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an embodiment, $R^2$ can be a phenyl group, a substituted phenyl group; alternatively, a phenyl group; or alternatively, a substituted phenyl group. In an embodiment, the substituted phenyl group, which can be utilized as $R^2$ can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an embodiment, one or more substituents of a multi-substituted phenyl group utilized as $R^2$ can be the same or different; alternatively, all the substituents of a multi-substituted cycloalkyl group can be the same; or alternatively, all the substituents of a multi-substituted cycloalkyl group can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^2$.

In a non-limiting embodiment, $R^2$ can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^2$. Generally, the alkyl substituents of a dialkylphenyl group (general or specific) or trialkylphenyl group (general or specific) can be the same; or alternatively, the alkyl substituents of a dialkylphenyl group or trialkylphenyl group can be different. In some non-limiting embodiments, one or more of $R^2$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting embodiment, $R^2$ can be a phenyl group, a 2-alkoxyphenyl group, or a 4-alkoxyphenyl group. In some non-limiting embodiments, $R^2$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group.

In a non-limiting embodiment, $R^2$ can be a phenyl group, a 2-halophenyl group, a 4-halophenyl group, or a 2,6-dihalophenyl group. Generally, the halides of a dihalophenyl group can be the same; or alternatively, the halides of a dihalophenyl group can be different. In some embodiments, $R^2$ can be a phenyl group, a 2-fluorophenyl group, a 4-fluorophenyl group, or a 2,6-difluorophenyl group.

In an embodiment, $R^2$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group which can be utilized as $R^2$.

Generally, $R^{2a}$ and/or $R^{2b}$, of the $N^2$-phosphinyl guanidine chromium compound complexes which have an $R^{2a}$ and/or $R^{2b}$ group, independently can be hydrogen or an organyl group; alternatively, hydrogen; or alternatively, an organyl group. In another aspect, $R^{2a}$ and/or $R^{2b}$, of the $N^2$-phosphinyl guanidine chromium compound complexes which have an $R^{2a}$ and/or $R^{2b}$ group, independently can be hydrogen or an organyl group consisting essentially of inert functional groups; alternatively, hydrogen; or alternatively, an organyl group consisting essentially of inert functional groups. In an aspect, $R^{2a}$ and/or $R^{2b}$, of the $N^2$-phosphinyl guanidine chromium compound complexes which have an $R^{2a}$ and/or $R^{2b}$ group, independently can be hydrogen or a hydrocarbyl group; alternatively, hydrogen; or alternatively, a hydrocarbyl group. In an embodiment, the $R^{2a}$ and $R^{2b}$ organyl groups of the $N^2$-phosphinyl guanidine chromium compound complexes which have an $R^{2a}$ and/or $R^{2b}$ organyl group, independently can be a $C_1$ to $C_{20}$, a $C_1$ to $C_{15}$, a $C_1$ to $C_{10}$, or a $C_1$ to $C_5$ organyl group. In some embodiments, the $R^{2a}$ and/or $R^{2b}$ organyl groups consisting of inert functional groups, of the $N^2$-phosphinyl guanidine chromium compound complexes which have an $R^{2a}$ and/or $R^{2b}$ organyl consisting of inert functional groups, independently can be a $C_1$ to $C_{20}$, a $C_1$ to $C_{15}$, a $C_1$ to $C_{10}$, or a $C_1$ to $C_5$ organyl group consisting essentially of inert functional groups. In other embodiments, the $R^{2a}$ and/or $R^{2b}$ hydrocarbyl groups, of the $N^2$-phosphinyl guanidine chromium compound complexes which have an $R^{2a}$ and/or $R^{2b}$ hydrocarbyl group, independently can be a $C_1$ to $C_{20}$, a $C_1$ to $C_{15}$, a $C_1$ to $C_{10}$, or a $C_1$ to $C_5$ hydrocarbyl group.

In an embodiment, $R^{2a}$ and $R^{2b}$, of the $N^2$-phosphinyl guanidine chromium compound complexes which have an $R^{2a}$ and/or $R^{2b}$ organyl group, independently can be an alkyl group, a substituted alkyl group, a cycloalkyl group, a substituted cycloalkyl group, an aryl group, a substituted aryl group, an aralkyl group, or a substituted aralkyl group. In some embodiments, $R^{2a}$ and $R^{2b}$, of the $N^2$-phosphinyl guanidine chromium compound complexes which have an $R^{2a}$ and/or $R^{2b}$ organyl group, independently can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^{2a}$ and $R^{2b}$, of the $N^2$-phosphinyl guanidine chromium compound complexes which have an $R^{2a}$ and/or $R^{2b}$ organyl group, independently can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, $R^{2a}$ and/or $R^{2b}$ independently can be $C_1$ to $C_{20}$, a $C_1$ to $C_{10}$, or a $C_1$ to $C_5$ alkyl group. In any aspect or embodiment disclosed herein, the cycloalkyl group which can be utilized as $R^{2a}$ and/or $R^{2b}$ independently can be a $C_4$ to $C_{20}$, a $C_4$ to $C_{15}$, or a $C_4$ to $C_{10}$ cycloalkyl group. In any aspect or embodiment disclosed herein, the substituted cycloalkyl group which can be utilized as $R^{2a}$ and/or $R^{2b}$ independently can be a $C_4$ to $C_{20}$, a $C_4$ to $C_{15}$, or a $C_4$ to $C_{10}$ substituted cycloalkyl group. In any aspect or embodiment disclosed herein, the aryl group which can be utilized as $R^{2a}$ and/or $R^{2b}$ independently can be a $C_6$ to $C_{20}$, a $C_6$ to $C_{15}$, or a $C_6$ to $C_{10}$ aryl group. In any aspect or embodiment disclosed herein, the substituted aryl group which can be utilized as $R^{2a}$ and/or $R^{2b}$ independently can be a $C_6$ to $C_{20}$, a $C_6$ to $C_{15}$, or a $C_6$ to $C_{10}$ substituted aryl group. Each substituent of a substituted cycloalkyl group (general or specific) and/or a substituted aryl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^{2a}$ and/or $R^{2b}$.

In an aspect, $R^1$ and $R^{2a}$ of the $N^2$-phosphinyl guanidine chromium compound complexes can be joined to form a group, $L^{12}$, wherein $L^{12}$, the $N^1$ nitrogen atom, and the $N^3$ nitrogen atom can form a ring or a ring system. In another aspect, $R^3$ and $R^{2b}$ of the $N^2$-phosphinyl guanidine chromium compound complexes can be joined to form a group, $L^{23}$, wherein $L^{23}$, the $N^2$ nitrogen atom, and the $N^3$ nitrogen atom can form a ring or a ring system. In an embodiment, $L^{12}$ and/or $L^{23}$, of the $N^2$-phosphinyl guanidine chromium compound complexes which have an $L^{12}$ group and/or an $L^{23}$ group, independently can be an organylene group; alternatively, an organylene group consisting of inert functional groups; or alternatively, a hydrocarbylene group. The organylene group which can be utilized as $L^{12}$ and/or $L^{23}$ of the $N^2$-phosphinyl guanidine chromium compound complexes which have an $L^{12}$ group and/or an $L^{23}$ group independently can be a $C_2$ to $C_{20}$, a $C_2$ to $C_{15}$, a $C_2$ to $C_{10}$, or a $C_2$ to $C_5$ organylene group. The organylene group consisting of inert functional groups which can be utilized as $L^{12}$ and/or $L^{23}$ of the $N^2$-phosphinyl guanidine chromium compound complexes which have an $L^{12}$ group and/or an $L^{23}$ group independently can be a $C_2$ to $C_{20}$, a $C_2$ to $C_{15}$, a $C_2$ to $C_{10}$, or a $C_2$ to $C_5$ organylene group consisting of inert functional groups. The hydrocarbylene group which can be utilized as $L^{12}$ and/or $L^{23}$ of the $N^2$-phosphinyl guanidine chromium compound complexes which have an $L^{12}$ group and/or an $L^{23}$ group independently can be a $C_2$ to $C_{20}$, a $C_2$ to $C_{15}$, a $C_2$ to $C_{10}$, or a $C_2$ to $C_5$ hydrocarbylene group.

In an embodiment, $L^{12}$ and/or $L^{23}$ can have any structure provided in Table 1. In some embodiments, $L^{12}$ and/or $L^{23}$ can have Structure 1L, Structure 2L, Structure 3L, Structure 4L or Structure 5L. In some embodiments, $L^{12}$ and/or $L^{23}$ can have Structure 2L or Structure 3L; alternatively, Structure 4L or Structure 5L. In other embodiments, $L^{12}$ and/or $L^{23}$ can have Structure 1L; alternatively, Structure 2L; alternatively, Structure 3L; alternatively, Structure 4L; or alternatively, Structure 5L. In some embodiments, $L^{12}$ and/or $L^{23}$ can have Structure 6L. It should be noted that when $L^{12}$ has Structure 6L the corresponding $R^{2b}$ is null because of the double bond link (depicted as real but can be delocalized through aromatic resonance) with the $N^3$ nitrogen atom of the $N^2$-phosphinyl guanidine metal complex.

TABLE 1

Structures for Linking Groups $L^{12}$ and/or $L^{23}$.

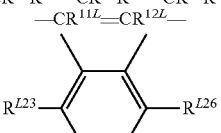

| | |
|---|---|
| $-(CR^{L1}R^{L2})_m-$ | Structure 1L |
| $-CR^{L3}R^{L4}-CR^{L5}R^{L6}-$ | Structure 2L |
| $-CR^{L3}R^{L4}-CR^{L7}R^{L8}-CR^{L5}R^{L6}-$ | Structure 3L |
| $-CR^{11L}=CR^{12L}-$ | Structure 4L |
| (phenylene structure with $R^{L23}$, $R^{L24}$, $R^{L25}$, $R^{L26}$) | Structure 5L |
| $=CR^{27}-CR^{28}=CR^{29}-$ | Structure 6L |

Within the structures of Table 1, the undesignated valences represent the points at which $L^{12}$ and/or $L^{23}$, when present, attach to the respective nitrogen atoms of the $N^2$-phosphinyl guanidine chromium compound complex. Generally, m can be an integer ranging from 2 to 5. In further embodiments, m can be 2 or 3; alternatively, m can be 2; or alternatively, m can be 3. $R^{L1}$ and $R^{L2}$ of the linking group having Structure 1L, $R^{L3}$, $R^{L4}$, $R^{L5}$, and $R^{L6}$ of the linking group having Structure 2L, $R^{L3}$, $R^{L4}$, $R^{L5}$, $R^{L6}$, $R^{L7}$, and $R^{L8}$, of the linking group having Structure 3L, $R^{L11}$ and $R^{L2}$ of the linking group having Structure 4L, $R^{L23}$, $R^{L24}$, $R^{L25}$, and $R^{L26}$ of the linking group having Structure 5L, $R^{L27}$, $R^{L28}$, and $R^{L29}$ of the linking group having Structure 6L independently can be a hydrogen or a non-hydrogen substituent group; or alternatively, hydrogen. Non-hydrogen substituent groups (general and specific) are independently disclosed herein and can be utilized without limitation to further describe the linking group having Structure 1L, Structure 2L, Structure 3L, Structure 4L, and/or Structure 5L. In an embodiment, $L^{12}$ and/or $L^{23}$ can be an eth-1,2-ylene group (—CH$_2$CH$_2$—), an ethen-1,2-ylene group (—CH=CH—), a prop-1,3-ylene group (—CH$_2$CH$_2$CH$_2$—), a 1-methylethen-1,2-ylene group (—C(CH$_3$)=CH—), a but-1,3-ylene group (—CH$_2$CH$_2$CH(CH$_3$)—), a 3-methylbut-1,3-ylene group (—CH$_2$CH$_2$C(CH$_3$)$_2$—), or a phen-1,2-ylene group. In some non-limiting embodiments, $L^{12}$ and/or $L^{23}$ be an eth-1,2-ylene group (—CH$_2$CH$_2$—), a prop-1,3-ylene group (—CH$_2$CH$_2$CH$_2$—), a 1-methylethen-1,2-ylene group (—C(CH$_3$)=CH—), a but-1,3-ylene group (—CH$_2$CH$_2$CH(CH$_3$)—), or a 3-methylbut-1,3-ylene group (—CH$_2$CH$_2$C(CH$_3$)$_2$—); alternatively, an eth-1,2-ylene group (—CH$_2$CH$_2$—), an ethen-1,2-ylene group (—CH=CH—), a prop-1,3-ylene group (—CH$_2$CH$_2$CH$_2$—), or a phen-1,2-ylene group; alternatively, an eth-1,2-ylene group (—CH$_2$CH$_2$—) or a prop-1,3-ylene group (—CH$_2$CH$_2$CH$_2$—); alternatively, an ethen-1,2-ylene group (—CH=CH—) or a phen-1,2-ylene group. In other embodiments, $L^{12}$ and/or $L^{23}$ can be an eth-1,2-ylene group (—CH$_2$CH$_2$—); alternatively, an ethen-1,2-ylene group (—CH=CH—); alternatively, a prop-1,3-ylene group (—CH$_2$CH$_2$CH$_2$—); alternatively, a 1-methylethen-1,2-ylene group (—C(CH$_3$)=CH—); alternatively, a but-,3-lene group (—CH$_2$CH$_2$CH(CH$_3$)—); alternatively, a 3-methylbut-1,3-ylene group (—CH$_2$CH$_2$C(CH$_3$)$_2$—); or alternatively, a phen-1,2-ylene group. In some embodiments, $L^{12}$ and/or $L^{23}$ can be a —CH=CH—CH= group.

In an embodiment, $L^{12}$ can have a structure that can comprise at least one substituent located on the carbon atom attached to the $N^1$ nitrogen atom of the $N^2$-phosphinyl guanidine chromium compound complex; alternatively, can comprise only one substituent located on the carbon atom attached to the $N^1$ nitrogen atom of the $N^2$-phosphinyl guanidine chromium compound complex; or alternatively, can comprise two substituents located on the carbon atom attached to the $N^1$ nitrogen atom of the $N^2$-phosphinyl guanidine chromium compound complex. In another embodiment, $L^{12}$ can have a structure that can consist of one substituent located on the carbon atom attached to the $N^1$ nitrogen atom of the $N^2$-phosphinyl guanidine chromium compound complex; or alternatively, can consist of two substituents located on the carbon atom attached to the $N^1$ nitrogen atom of the $N^2$-phosphinyl guanidine chromium compound complex.

In an embodiment, $R^{2a}$ and $R^{2b}$ of the $N^2$-phosphinyl guanidine chromium compound complexes can be joined to form a group, $L^{22}$, wherein $R^{2a}$, $R^{2b}$, and the $N^3$ nitrogen (or $L^{22}$ and the $N^3$ nitrogen) form a ring or ring system. In an embodiment, $L^{22}$ of the $N^2$-phosphinyl guanidine chromium compound complexes having an $L^{22}$ group can be an organylene group; alternatively, an organylene group consisting of inert functional groups; or alternatively, a hydrocarbylene group. The organylene group which can be utilized as $L^{22}$ of the $N^2$-phosphinyl guanidine chromium compound complexes having an $L^{22}$ group can be a $C_3$ to $C_{20}$, a $C_3$ to $C_{15}$, or a $C_3$ to $C_{10}$ organylene group. The organylene group consisting of inert functional groups which can be utilized as $L^{22}$ of the $N^2$-phosphinyl guanidine chromium compound complexes having an $L^{22}$ group can be a $C_3$ to $C_{20}$, a $C_3$ to $C_{15}$, or a $C_3$ to $C_{10}$ organylene group consisting of inert functional groups. The hydrocarbylene group which can be utilized as $L^{22}$ of the $N^2$-phosphinyl guanidine chromium compound complexes having an $L^{22}$ group can be a $C_4$ to $C_{20}$, a $C_4$ to $C_{15}$, or a $C_4$ to $C_{10}$ hydrocarbylene group.

In an embodiment, $L^{22}$ can have any structure provided in Table 2. In some embodiments, $L^{22}$ can have Structure 11L, Structure 12L, Structure 13L, Structure 14L, Structure 15L; or Structure 16L. In other embodiments, $L^{22}$ can have Structure 11L; alternatively, Structure 12L; alternatively, Structure 13L; alternatively, Structure 14L; or alternatively, Structure 15L.

TABLE 2

Structures for Linking Groups $L^{22}$.

| | |
|---|---|
| —$(CR^{L31}R^{L32})_n$— | Structure 11L |
| —$CR^{L41}R^{L42}$—$CR^{L45}R^{L46}$ $CR^{L47}R^{L48}$ $CR^{L43}R^{L44}$— | Structure 12L |
| —$CR^{L41}R^{L42}$—$CR^{L45}R^{L46}$—$CR^{L49}R^{L50}$—$CR^{L47}R^{L48}$—$CR^{L43}R^{L44}$— | Structure 13L |
| —$CR^{L41}R^{L42}$—$CR^{L45}R^{L46}$—O—$CR^{L47}R^{L48}$—$CR^{L43}R^{L44}$— | Structure 14L |
| —$CR^{L51}$=$CR^{L53}$—$CR^{L54}$=$CR^{L52}$— | Structure 15L |

Within the structures of Table 2, the undesignated valences represent the points at which $L^{22}$ of the $N^2$-phosphinyl guanidine chromium compound complexes, when present, attach to the $N^3$ nitrogen atom of the $N^2$-phosphinyl guanidine chromium compound complex. Generally, n can be an integer ranging from 4 to 7. In further embodiments, n can be 4 or 5; alternatively, n can be 4; or alternatively, n can be 5. $R^{L31}$ and $R^{L32}$ of the linking group having Structure 11L, $R^{L41}$, $R^{L42}$, $R^{L43}$, $R^{L44}$, $R^{L45}$, $R^{L46}$, $R^{L47}$, and $R^{L48}$, of the linking group having Structure 12L, $R^{L41}$, $R^{L42}$, $R^{L43}$, $R^{L44}$, $R^{L45}$, $R^{L46}$, $R^{L47}$, and $R^{L50}$ of the linking group having Structure 13L, $R^{L41}$, $R^{L42}$, $R^{L43}$, $R^{L44}$, $R^{L45}$, $R^{L46}$, $R^{L47}$, and $R^{L48}$ of the linking group having Structure 14L, and $R^{L41}$, $R^{L42}$, $R^{L43}$, $R^{L44}$, $R^{L45}$, $R^{L46}$, $R^{L47}$, and $R^{L48}$ of the linking group having Structure 15L independently can be a hydrogen or a non-hydrogen substituent group; alternatively, hydrogen. Non-hydrogen substituent groups are independently disclosed herein and can be utilized without limitation to further describe the linking group having Structure 11L, Structure 12L, Structure 13L, Structure 14L, and/or Structure 15L. In an embodiment, $L^{22}$ can be a but-1,4-ylene group, a pent-1,4-ylene group, a pent-1,5-ylene group, a hex-2,5-ylene group, a hex-1,5-ylene group, a hept-2,5-ylene group, a buta-1,3-dien-1,4-ylene group, or a bis(eth-2-yl)ether group; alternatively, a but-1,4-ylene group, a pent-1,5-ylene group, or a bis(eth-2-yl)ether group; alternatively, a but-1,4-ylene group; alternatively, a pent-1,5-ylene group; alternatively, a buta-1,3-dien-1,4-ylene group; or alternatively, a bis(eth-2-yl)ether group.

Generally, $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be hydrogen or an organyl group; hydrogen or an organyl group consisting essentially of inert functional group; alternatively, hydrogen or a hydrocarbyl group; alternatively, hydrogen; alternatively, an organyl group; alternatively, an organyl group consisting essentially of inert functional group; or alternatively, a hydrocarbyl group. In an embodiment, the organyl group which can be utilized as $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a, a $C_1$ to $C_{20}$, a $C_1$ to $C_{15}$, a $C_1$ to $C_{10}$, or a $C_1$ to $C_5$ organyl group. In an embodiment, the organyl group consisting essentially of inert functional groups which can utilized as $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, the hydrocarbyl group which can utilized as $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a, a $C_1$ to $C_{20}$, a $C_1$ to $C_{15}$, a $C_1$ to $C_{10}$, or a $C_1$ to $C_5$ hydrocarbyl group. In other embodiments, $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a $C_1$ to $C_{30}$, a $C_1$ to $C_{20}$, a $C_1$ to $C_{15}$, a $C_1$ to $C_{10}$, or a $C_1$ to $C_5$ alkyl group. In yet other embodiments, $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. Substituent groups (general and specific) are provided herein and these substituent groups can be utilized to further describe the substituted phenyl groups which can be utilized as $R^3$ of any of the $N^2$-phosphinyl formamidine chromium compound complexes, the $N^2$-phosphinyl amidine chromium compound complexes, and/or the $N^2$-phosphinyl guanidine chromium compound complexes having a non-hydrogen $R^3$ group.

Generally, $R^4$ and/or $R^5$ of the $N^2$-phosphinyl formamidine chromium compound complexes, the $N^2$-phosphinyl amidine chromium compound complexes, and/or the $N^2$-phosphinyl guanidine chromium compound complexes independently can be an organyl group; alternatively, an organyl group consisting essentially of inert functional groups; or alternatively, a hydrocarbyl group. In an embodiment, the $R^4$ and/or $R^5$ organyl groups of the $N^2$-phosphinyl formamidine chromium compound complexes, the $N^2$-phosphinyl amidine chromium compound complexes, and/or the $N^2$-phosphinyl guanidine chromium compound complexes independently can be a $C_1$ to $C_{20}$, a $C_1$ to $C_{15}$, a $C_1$ to $C_{10}$, or a $C_1$ to $C_5$ organyl group. In an embodiment, the $R^4$ and/or $R^5$ organyl groups consisting essentially of inert functional groups of the $N^2$-phosphinyl formamidine chromium compound complexes, the $N^2$-phosphinyl amidine chromium compound complexes, and/or the $N^2$-phosphinyl guanidine chromium compound complexes independently can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, the $R^4$ and/or $R^5$ hydrocarbyl groups of the $N^2$-phosphinyl formamidine chromium compound complexes, the $N^2$-phosphinyl amidine chromium compound complexes, and/or the $N^2$-phosphinyl guanidine chromium compound complexes independently can be a, a $C_1$ to $C_{20}$, a $C_1$ to $C_{15}$, a $C_1$ to $C_{10}$, or a $C_1$ to $C_5$ hydrocarbyl group. In further embodiments, $R^4$ and $R^5$ of the $N^2$-phosphinyl formamidine chromium compound complexes, the $N^2$-phosphinyl amidine chromium compound complexes, and/or the $N^2$-phosphinyl guanidine chromium compound complexes can be joined to form a ring or a ring system.

In an embodiment, $R^4$ and/or $R^5$ of the $N^2$-phosphinyl formamidine chromium compound complexes, the $N^2$-phosphinyl amidine chromium compound complexes, and/or the $N^2$-phosphinyl guanidine chromium compound complexes independently can be an alkyl group, a substituted alkyl group, a cycloalkyl group, a substituted cycloalkyl group, an aryl group, a substituted aryl group, an aralkyl group, or a substituted aralkyl group. In some embodiments, $R^4$ and/or $R^5$ of the $N^2$-phosphinyl formamidine chromium compound complexes, the $N^2$-phosphinyl amidine chromium compound complexes, and/or the $N^2$-phosphinyl guanidine chromium compound complexes independently can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^4$ and/or $R^5$ of the $N^2$-phosphinyl formamidine chromium compound complexes, the $N^2$-phosphinyl amidine chromium compound complexes, and/or the $N^2$-phosphinyl guanidine chromium compound complexes independently can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, each alkyl group which can be utilized as $R^4$ and/or $R^5$ independently can be a $C_1$ to $C_{20}$, a $C_1$ to $C_{10}$, or a $C_1$ to $C_5$ alkyl group. In any aspect or embodiment disclosed herein, each substituted alkyl group which can be utilized as $R^4$ and/or $R^5$ independently can be a $C_1$ to $C_{20}$, a $C_1$ to $C_{10}$, or $C_1$ to $C_5$ substituted alkyl group. In any aspect or embodiment disclosed herein, each cycloalkyl group which can be utilized as $R^4$ and/or $R^5$ independently can be a $C_4$ to $C_{20}$, a $C_4$ to $C_{15}$, or a $C_4$ to $C_{10}$ cycloalkyl group. In any aspect or embodiment disclosed herein, each substituted cycloalkyl group which can be utilized as $R^4$ and/or $R^5$ independently can be a $C_4$ to $C_{20}$, a $C_4$ to $C_{15}$, or a $C_4$ to $C_{10}$ substituted cycloalkyl group. In any aspect or embodiment disclosed herein, each aryl group which can be utilized as $R^4$ and/or $R^5$ independently can be a $C_6$ to $C_{20}$, a $C_6$ to $C_{15}$, or a $C_6$ to $C_{10}$ aryl group. In any aspect or embodiment disclosed herein, each substituted aryl group which can be utilized as $R^4$ and/or $R^5$ independently can be a $C_6$ to $C_{20}$, a $C_6$ to $C_{15}$, or a $C_6$ to $C_{10}$ substituted aryl group. In any aspect or embodiment disclosed herein, each aralkyl group which can be utilized $R^4$ and/or $R^5$ independently can be a $C_7$ to $C_{20}$, a $C_7$ to $C_{15}$, or a $C_7$ to $C_{10}$ aralkyl group. In any aspect or embodiment disclosed herein, each substituted aryl group which can be utilized as $R^4$ and/or $R^5$ independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^4$ and/or $R^5$.

In an embodiment, $R^4$ and $R^5$ independently can be a methyl group, an ethyl group, a propyl group, a butyl group, a pentyl group, a hexyl group, a heptyl group, or an octyl group. In some embodiments, $R^4$ and $R^5$ independently can be a methyl group, an ethyl group, an n-propyl (1-propyl) group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some embodiments, the alkyl groups which can be utilized as $R^4$ and/or $R^5$ can be substituted. Each substituent of a substituted alkyl group independently can be a halogen or a hydrocarboxy group; alternatively, a halogen; or alternatively, a hydrocarboxy group. Substituent halogens and substituent hydrocarboxy (general and specific) groups are independently disclosed herein. These substituent halogens and substituent hydrocarboxy groups can be utilized without limitation to further describe a substituted alkyl group which can be utilized as $R^4$ and/or $R^5$ independently.

In an embodiment, $R^4$ and $R^5$ independently can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an embodiment, the substituted cycloalkyl group, which can be utilized for $R^4$ and/or $R^5$, can be a 2-substituted cyclohexyl group, a 2,6-disubstituted cyclohexyl group, a 2-substituted cyclopentyl group, or a 2,6-disubstituted cyclopentyl group; alternatively, a 2-substituted cyclohexyl group or a 2,6-disubstituted cyclohexyl group; alternatively, a 2-substituted cyclopentyl group or a 2,6-disubstituted cyclopentyl group; alternatively, a 2-substituted cyclohexyl group or a 2-substituted cyclopentyl group; alternatively, a 2,6-disubstituted cyclohexyl group or a 2,6-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,6-disubstituted cyclopentyl group. In an embodiment where the substituted cycloalkyl group (general or specific) has more the one substituent, the substituents can be the same or different; alternatively, the same; or alternatively, different. Each substituent of a cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^4$ and/or $R^5$.

In a non-limiting embodiment, $R^4$ and $R^5$ independently can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, or 2,5-dialkylcyclopentyl group. Alkyl substituent groups (general and specific) are independently described herein and these alkyl substituent groups can be utilized, without limitation, to further described alkylcyclohexyl groups (general or specific), dialkylcyclohexyl groups (general or specific), alkylcyclopentyl groups (general or specific), and/or dialkylcyclopentyl groups (general or specific) which can be utilized as $R^4$ and/or $R^5$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting embodiments, $R^4$ and $R^5$ independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting embodiments, $R^4$ and $R^5$ independently can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an embodiment, $R^4$ and $R^5$ independently can be a phenyl group, a substituted phenyl group; alternatively, a phenyl group; or alternatively, a substituted phenyl group. In an embodiment, the substituted phenyl group, which can be utilized for $R^4$ and/or $R^5$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an embodiment, one or more substituents of a multi-substituted phenyl group utilized as $R^4$ and/or $R^5$ can be the same or different; alternatively, all the substituents of a multi-substituted cycloalkyl group can be the same; or alternatively, all the substituents of a multi-substituted cycloalkyl group different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^4$ and/or $R^5$.

In a non-limiting embodiment, $R^4$ and $R^5$ independently can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^4$ and/or $R^5$. Generally, the alkyl substituents of a dialkylphenyl group (general or specific) or a trialkylphenyl group (general or specific) can be the same; or alternatively, the alkyl substituents of a dialkylphenyl group (general or specific) or a trialkyl phenyl group (general or specific) can be different. In some non-limiting embodiments, $R^4$ and $R^5$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting embodiment, $R^4$ and $R^5$ can be a phenyl group, a 2-alkoxyphenyl group, or a 4-alkoxyphenyl group. In some non-limiting embodiments, $R^4$ and/or $R^5$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group.

In a non-limiting embodiment, $R^4$ and $R^5$ independently can be a phenyl group, a 2-halophenyl group, a 4-halophenyl group, or a 2,6-dihalophenyl group. Generally, the halides of a dihalophenyl group can be the same; or alternatively, the halides of a dihalophenyl group can be different. In some embodiments, $R^4$ and $R^5$ independently can be a phenyl group, a 2-fluorophenyl group, a 4-fluorophenyl group, or a 2,6-difluorophenyl group.

In an embodiment, $R^4$ and $R^5$ independently can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl which can be utilized as $R^4$ and/or $R^5$.

Generally, the chromium compound of the $N^2$-phosphinyl formamidine chromium compound complexes, the $N^2$-phosphinyl amidine chromium compound complexes, and/or the $N^2$-phosphinyl guanidine chromium compound complexes described herein can have the formula $CrX_p$ where X represents a monoanionic ligand, and p represent the number of monoanionic ligands (and the oxidation state of the chromium in the chromium compound). The monoanionic ligand (X) and p are independent elements of the chromium compound and are independently described herein. The independent descriptions of the monoanionic ligand (X) and p can be utilized without limitation, and in any combination, to further describe the chromium compound of the $N^2$-phosphinyl formamidine chromium compound complexes, the $N^2$-phosphinyl amidine chromium compound complexes, and/or the $N^2$-phosphinyl guanidine chromium compound complexes.

Generally, the chromium atom of the chromium compound ($CrX_p$) can have any positive oxidation state available to a chromium atom. In an embodiment, the chromium atom can have an oxidation state of from +2 to +6; alternatively, from +2 to +4; or alternatively, from +2 to +3. In some embodiments, the chromium atom of the chromium compound ($CrX_p$) can have an oxidation state of +1; alternatively, +2; alternatively, +3; or alternatively, +4.

The monoanion, X, of the chromium compound can be any monoanion. In an embodiment, the monoanion, X, can be a halide, a carboxylate, a β-diketonate, a hydrocarboxide, a nitrate, or a chlorate. In some embodiments, the monoanion, X, can be a halide, a carboxylate, a β-diketonate, or a hydrocarboxide. In any aspect or embodiment, the hydrocarboxide can be an alkoxide, an aryloxide, or an aralkoxide. Generally, hydrocarboxide (and subdivisions of hydrocarboxide) are the anion analogues of the hydrocarboxy group. In other embodiments, the monoanion, X, can be a halide, a carboxylate, a β-diketonate, or an alkoxide; or alternatively, a halide or a β-diketonate. In other embodiments, the monoanion, X, can be a halide; alternatively, a carboxylate; alternatively, a β-diketonate; alternatively, a hydrocarboxide; alternatively, an alkoxide; or alternatively, an aryloxide. Generally, the number, p, of monoanions can equal the oxidation state of the metal atom. In an embodiment, the number, p, of monoanions, X, can be from 2 to 6; alternatively, from 2 to 4; alternatively, from 2 to 3; alternatively, 1; alternatively, 2; alternatively, 3; or alternatively, 4.

Generally, each halide monoanion, X, of the chromium compound independently can be fluorine, chlorine, bromine, or iodine; or alternatively, chlorine, bromine, or iodine. In an embodiment, each halide monoanion, X, of the chromium compound can be chlorine; alternatively, bromine; or alternatively, iodine.

Generally, each carboxylate monoanion of the chromium compound independently can be a $C_1$ to $C_{20}$ carboxylate; or alternatively, a $C_1$ to $C_{10}$ carboxylate. In an embodiment, each carboxylate monoanion of the chromium compound independently can be acetate, a propionate, a butyrate, a pentanoate, a hexanoate, a heptanoate, an octanoate, a nonanoate, a decanoate, an undecanoate, or a dodecanoate; or alternatively, a pentanoate, a hexanoate, a heptanoate, an octanoate, a nonanoate, a decanoate, an undecanoate, or a dodecanoate. In some embodiments, each carboxylate monoanion of the chromium compound independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, capronate (n-hexanoate); alternatively, n-heptanoate; alternatively, caprylate (n-octanoate); or alternatively, 2-ethylhexanoate. In some embodiments, the carboxylate monoanion of the chromium compound can be triflate (trifluoroacetate).

Generally, each β-diketonate monoanion of the chromium compound independently can be any $C_1$ to $C_{20}$ a β-diketonate; or alternatively, any $C_1$ to $C_{10}$ β-diketonate. In an embodiment, each β-diketonate monoanion of the chromium compound independently can be acetylacetonate (i.e., 2,4-pentanedionate), hexafluoroacetylacetone (i.e., 1,1,1,5,5,5-hexafluoro-2,4-pentanedionate), or benzoylacetonate; alternatively, acetylacetonate; alternatively, hexafluoroacetylacetone; or alternatively, benzoylacetonate.

Generally, each hydrocarboxide monoanion of the chromium compound independently can be any $C_1$ to $C_{20}$ hydrocarboxide; or alternatively, any $C_1$ to $C_{10}$ hydrocarboxide. In an embodiment, each hydrocarboxide monoanion of the chromium compound independently can be a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide. In an embodiment, each alkoxide monoanion of the chromium compound independently can be methoxide, ethoxide, a propoxide, or a butoxide. In some embodiments, each alkoxide monoanion of the chromium compound independently can be methoxide, ethoxide, isopropoxide, or tert-butoxide; alternatively, methoxide; alternatively, an ethoxide; alternatively, an iso-propoxide; or alternatively, a tert-butoxide. In an aspect, the aryloxide can be phenoxide.

In a non-limiting embodiment, the chromium compound of any of the $N^2$-phosphinyl formamidine chromium compound complexes, $N^2$-phosphinyl amidine chromium compound complexes, and/or the $N^2$-phosphinyl guanidine chromium compound complexes described herein can comprise, can consist essentially of, or consist of, a chromium(II) halide, a chromium(III) halide, a chromium(II) carboxylate, chromium(III) carboxylate, a chromium(II) β-diketonate, or a chromium(III) β-diketonate. In some non-limiting embodiments, the chromium compound of any of the $N^2$-phosphinyl formamidine chromium compound complexes, $N^2$-phosphinyl amidine chromium compound complexes, and/or the $N^2$-phosphinyl guanidine chromium compound complexes described herein can comprise, can consist essentially of, or consist of, a chromium(II) halide, a chromium(II) carboxylate, or a chromium(II) β-diketonate; or alternatively, a chromium(III) halide, a chromium(III) carboxylate, or a chromium(III) β-diketonate. In other non-limiting embodiments, the chromium compound of any of the $N^2$-phosphinyl formamidine chromium compound complexes, $N^2$-phosphinyl amidine chromium compound complexes, and/or $N^2$-phosphinyl guanidine chromium compound complexes described herein can comprise, can consist essentially of, or consist of, a chromium(II) halide; alternatively, a chromium(III) halide; alternatively, a chromium (II) carboxylate; alternatively, a chromium(III) carboxylate; alternatively, a chromium(II) β-diketonate; or alternatively, a chromium(III) β-diketonate.

In a non-limiting embodiment, the chromium compound of any of the $N^2$-phosphinyl formamidine chromium compound complexes, $N^2$-phosphinyl amidine chromium compound complexes, and/or $N^2$-phosphinyl guanidine chromium compound complexes described herein can comprise, can consist essentially of, or consist of, chromium(II) chloride, chromium(III) chloride, chromium(II) fluoride, chromium(III) fluoride, chromium(II) bromide, chromium(III) bromide, chromium(II) iodide, chromium(III) iodide, chromium(II) acetate, chromium(III) acetate, chromium(II) 2-ethylhexanoate, chromium(III) 2-ethylhexanoate, chromium(II) triflate, chromium(III) triflate, chromium(II) nitrate, chromium(III) nitrate, chromium(II) acetylacetonate, chromium(III) acetylacetonate, chromium(II) hexafluoracetylacetonate, chromium(III) hexafluoracetylacetonate, chromium (III) benzoylacetonate, or chromium(III) benzoylacetonate. In some non-limiting embodiments, the chromium compound of any of the $N^2$-phosphinyl formamidine chromium compound complexes, $N^2$-phosphinyl amidine chromium compound complexes, and/or $N^2$-phosphinyl guanidine chromium compound complexes described herein can comprise, can consist essentially of, or consist of, chromium(III) chloride, chromium(III) fluoride, chromium(III) bromide, chromium(III) iodide, chromium(III) chloride (THF) complex, chromium(III) acetate, chromium(III) 2-ethylhexanoate, chromium(III) triflate, chromium(III) nitrate, chromium (III) acetylacetonate, chromium(III) hexafluoracetylacetonate, or chromium(III) benzoylacetonate. In further embodiments, the chromium compound of any of the $N^2$-phosphinyl formamidine chromium compound complexes, $N^2$-phosphinyl amidine chromium compound complexes, and/or $N^2$-phosphinyl guanidine chromium compound complexes described herein can be chromium(III) chloride, or chromium(III) acetylacetonate; alternatively, chromium(III) chloride; or alternatively, chromium(III) acetylacetonate.

Generally, the neutral ligand, Q, of any of the $N^2$-phosphinyl formamidine chromium compound complexes, the $N^2$-phosphinyl amidine chromium compound complexes, and/or the $N^2$-phosphinyl guanidine chromium compound complexes described herein, if present, independently can be any neutral ligand that forms an isolatable compound with the $N^2$-phosphinyl formamidine chromium compound complex, the $N^2$-phosphinyl amidine chromium compound complex, and/or the $N^2$-phosphinyl guanidine chromium compound complex. In an aspect, each neutral ligand independently can be a nitrile or an ether; alternatively, a nitrile; or alternatively, an ether. The number of neutral ligands, q, can be any number that forms an isolatable compound with the $N^2$-phosphinyl formamidine chromium compound complexes, the $N^2$-phosphinyl amidine chromium compound complexes, and/or the $N^2$-phosphinyl guanidine chromium compound complexes. In an aspect, the number of neutral ligands of any of the $N^2$-phosphinyl formamidine chromium compound complexes, the $N^2$-phosphinyl amidine chromium compound complexes, and/or the $N^2$-phosphinyl guanidine chromium compound complexes described herein can be from 0 to 6; alternatively, 0 to 3; alternatively, 0; alternatively, 1; alternatively, 2; alternatively, 3; or alternatively, 4.

Generally, each nitrile ligand independently can be a $C_2$ to $C_{20}$ nitrile; or alternatively, a $C_2$ to $C_{10}$ nitrile. In an embodiment, each nitrile ligand independently can be a $C_2$ to $C_{20}$ aliphatic nitrile, a $C_7$ to $C_{20}$ aromatic nitrile, a $C_8$ to $C_{20}$ aralkane nitrile, or any combination thereof; alternatively, a $C_2$ to $C_{20}$ aliphatic nitrile; alternatively, a $C_7$ to $C_{20}$ aromatic nitrile; or alternatively, a $C_8$ to $C_{20}$ aralkane nitrile. In some embodiments, each nitrile ligand independently can be a $C_2$ to $C_{10}$ aliphatic nitrile, a $C_7$ to $C_{10}$ aromatic nitrile, a $C_8$ to $C_{10}$ aralkane nitrile, or any combination thereof; alternatively, a $C_1$ to $C_{10}$ aliphatic nitrile; alternatively, a $C_7$ to $C_{10}$ aromatic nitrile; or alternatively, a $C_8$ to $C_{10}$ aralkane nitrile. In an embodiment, each aliphatic nitrile independently can be acetonitrile, propionitrile, a butyronitrile, benzonitrile, or any combination thereof; alternatively, acetonitrile; alternatively, propionitrile; alternatively, a butyronitrile; or alternatively, benzonitrile.

Generally, each ether ligand independently can be a $C_2$ to $C_{40}$ ether; alternatively, a $C_2$ to $C_{30}$ ether; or alternatively, a $C_2$ to $C_{20}$ ether. In an embodiment, each ether ligand independently can be a $C_2$ to $C_{40}$ aliphatic ether, a $C_3$ to $C_{40}$ aliphatic cyclic ether, a $C_4$ to $C_{40}$ aromatic cyclic ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; or alternatively, a $C_4$ to $C_{40}$ aromatic cyclic ether. In some embodiments, each ether ligand independently can be a $C_2$ to $C_{30}$ aliphatic ether, a $C_3$ to $C_{30}$ aliphatic cyclic ether, a $C_4$ to $C_{30}$ aromatic cyclic ether; alternatively, a $C_2$ to $C_{30}$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other embodiments, each ether ligand independently can be a $C_2$ to $C_{20}$ aliphatic ether, a $C_3$ to $C_{20}$ aliphatic cyclic ether, a $C_4$ to $C_{20}$ aromatic cyclic ether; alternatively, a $C_2$ to $C_{20}$ aliphatic acyclic ether or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In some embodiments, each ether ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, dibenzofuran, diphenyl ether, a ditolyl ether, or any combination thereof; alternatively, dimethyl ether, diethyl ether, a dipropyl ether, a dibutyl ether, methyl ethyl ether, a methyl propyl ether, a methyl butyl ether, or any combination thereof; tetrahydrofuran, a dihydrofuran, 1,3-dioxolane, tetrahydropyran, a dihydropyran, a pyran, a dioxane, or any combination thereof; furan, benzofuran, isobenzofuran, dibenzofuran, or any combination thereof; diphenyl ether, a ditolyl ether, or any combination thereof; alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, dibenzofuran; alternatively, diphenyl ether; or alternatively, a ditolyl ether.

In a non-limiting embodiment, the $N^2$-phosphinyl formamidine chromium compound complex can be any one or more of NPFCr I, NPFCr II, NPFCrR III, NPFCr IV, NPFCr V, and NPFCr VI. In a non-limiting embodiment, the $N^2$-phosphinyl amidine chromium compound complex can be any one or more of NPACR I, NPACR II, NPACr III, NPACr IV, NPACr V, NPACr VI, NPACr VII, NPACr VIII, NPACr IX, NPACr X, NPACr XI, and NPACr XII. In a non-limiting embodiment, the $N^2$-phosphinyl guanidine chromium compound complex can be any one or more of GuFCr I, GuCr II, GuCr III, GuCr IV, GuCr V, and GuCr VI. In a non-limiting embodiments, the chromium compound, $CrX_3$, of any of NPFCr I, NPFCr II, NPFCrR III, NPFCr IV, NPFCr V, NPFCr VI, NPACR I, NPACR II, NPACr III, NPACr IV, NPACr V, NPACr VI, NPACr VII, NPACr VIII, NPACr IX, NPACr X, NPACr XI, NPACr XII, GuFCr I, GuCr II, GuCr III, GuCr IV, GuCr V, and GuCr VI can be chromium(III) chloride or chromium(III) acetylacetonate; alternatively, chromium(III) chloride; or alternatively, chromium(III) acetylacetonate.

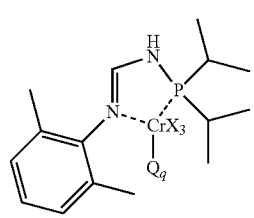

NPFCr I

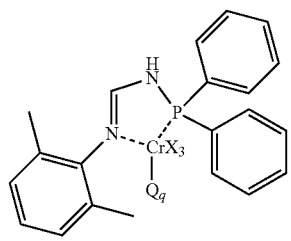

NPFCr II

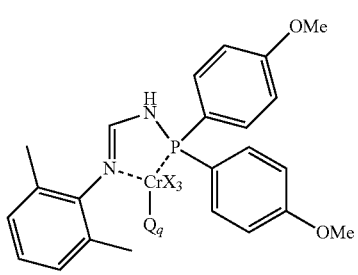

NPFCr III

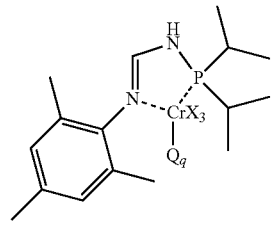

NPFCr IV

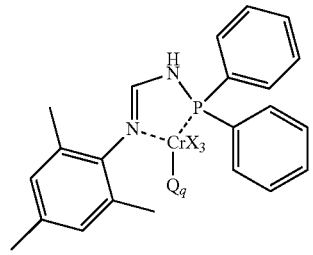

NPFCr V

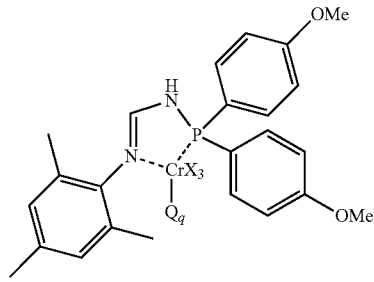

NPFCr VI

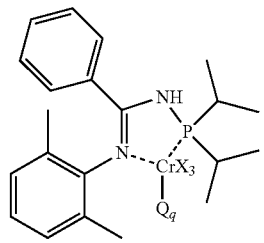

NPACr I

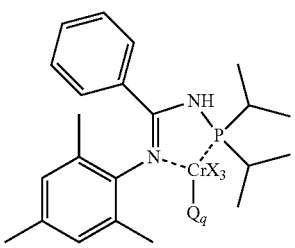

NPACr II

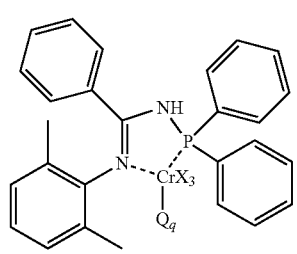

NPACr III

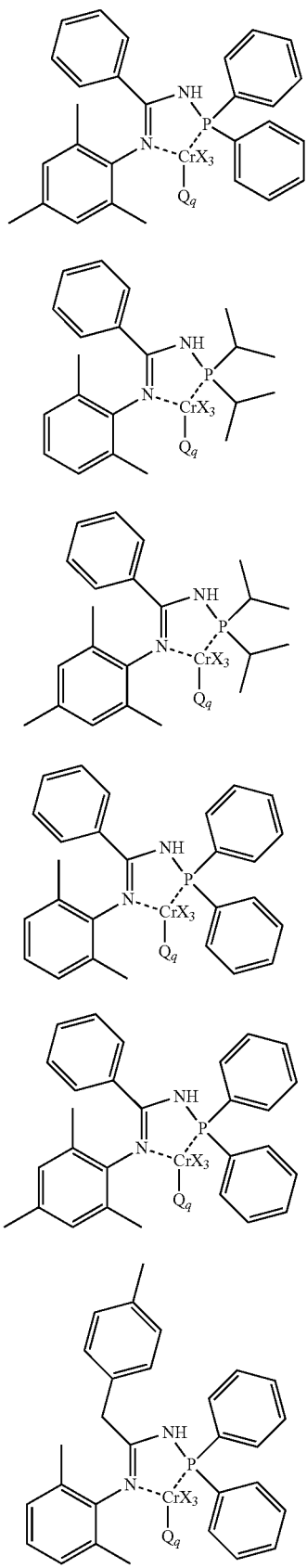
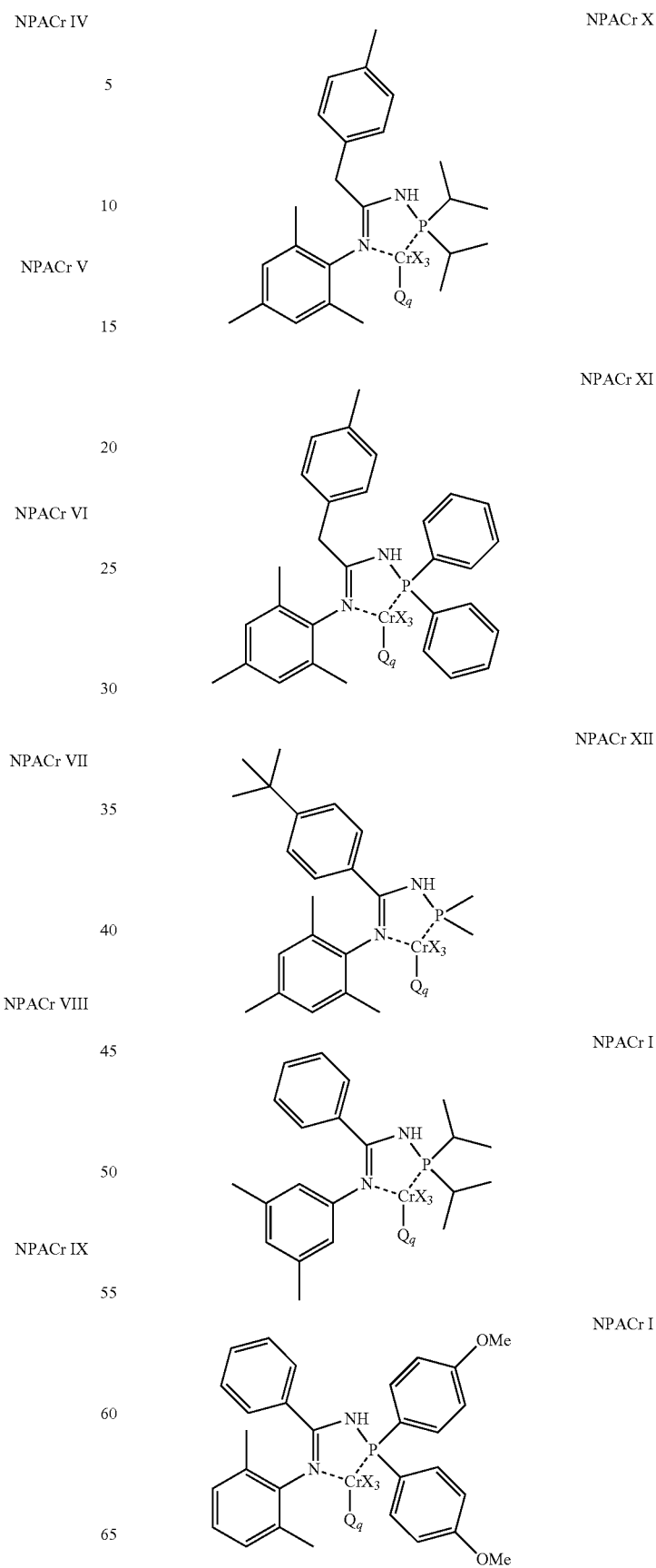

NPACr I

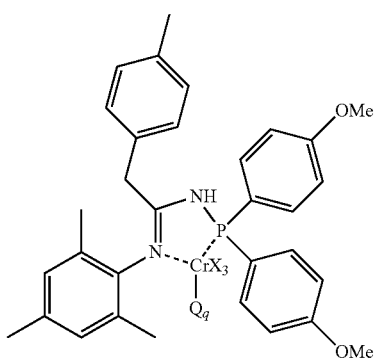

NPACr I

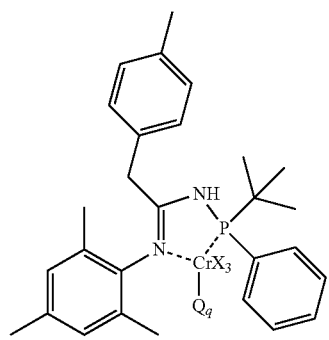

GuCr I

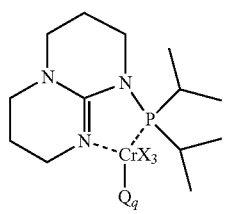

GuCr II

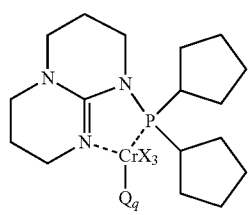

GuCr III

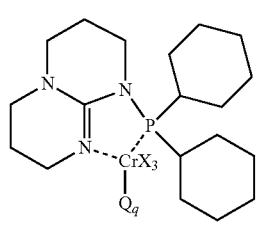

GuCr IV

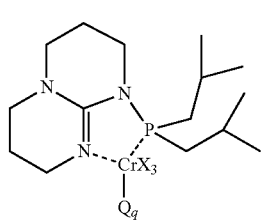

GuCr V

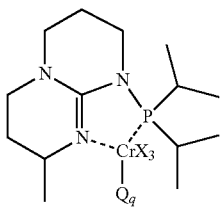

GuCrV I

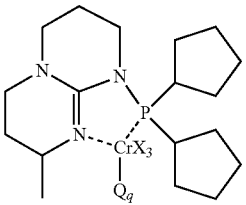

Generally, the aluminoxane utilized in the catalyst systems which are utilized in the processes, systems, and/or reaction systems can be any aluminoxane which can, in conjunction with the $N^2$-phosphinyl formamidine chromium compound complex, the $N^2$-phosphinyl amidine chromium compound complex, and/or the $N^2$-phosphinyl guanidine chromium compound complex, catalyze the formation of an oligomer product. In a non-limiting embodiment, the aluminoxane can have a repeating unit characterized by the Formula I:

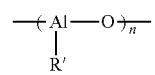

Formula I wherein R' is a linear or branched alkyl group. Alkyl groups for metal alkyl compounds are independently described herein and can be utilized without limitation to further describe the aluminoxanes having Formula I. Generally, n of Formula I can be greater than 1; or alternatively, greater than 2. In an embodiment, n can range from 2 to 15; or alternatively, range from 3 to 10.

In an aspect, each alkyl group of the aluminoxane independently can be, comprise, or consist essentially of, a $C_1$ to $C_{20}$ alkyl group; alternatively, a $C_1$ to $C_{10}$ alkyl group; or alternatively, a $C_1$ to $C_6$ alkyl group. In an embodiment, each alkyl group of the aluminoxane independently can be, comprise, or consist essentially of, a methyl group, an ethyl group, a propyl group, a butyl group, a pentyl group, a hexyl group, a heptyl group, or an octyl group; alternatively, a methyl group, a ethyl group, a butyl group, a hexyl group, or an octyl group. In some embodiments, each alkyl group or the aluminoxane independently can be, comprise, or consist essentially of, a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group. In a non-limiting embodiment, the aluminoxane can be, comprise, or consist essentially of, methylaluminoxane (MAO), ethylaluminoxane, modified methylaluminoxane (MMAO), n-propylaluminoxane, iso-propyl-aluminoxane, n-butylaluminoxane, sec-butylaluminoxane, iso-butylaluminoxane, t-butylaluminoxane, 1-pentylaluminoxane, 2-pentylaluminoxane, 3-pentyl-aluminoxane, iso-pentyl-aluminoxane, neopentylaluminoxane, or mixtures thereof. In some non-limiting embodiments, the aluminoxane can be, comprise, or consist essentially of, methylaluminoxane (MAO), modified methylaluminoxane (MMAO), isobutyl aluminoxane, t-butyl aluminoxane, or mixtures thereof. In other non-limiting embodiments, the aluminoxane can be, comprise, or consist essentially of, methylaluminoxane (MAO); alternatively, ethylaluminoxane; alternatively, modified methylaluminoxane (MMAO); alternatively, n-propylaluminoxane; alternatively, iso-propyl-aluminoxane; alternatively, n-butylaluminoxane; alternatively, sec-butylaluminoxane; alternatively, iso-butylaluminoxane; alternatively, t-butyl aluminoxane; alternatively, 1-pentyl-aluminoxane; alternatively, 2-pentylaluminoxane; alternatively, 3-pentyl-aluminoxane; alternatively, iso-pentyl-aluminoxane; or alternatively, neopentylaluminoxane.

The scrub agent which can be utilized in aspects and embodiments of any of the processes, systems, and/or reaction systems described herein can be any compound(s) which can remove water, oxygen, and/or other species detrimental to the ability of the catalyst system oligomerizing ethylene. In some embodiments, the scrub agent can be an organoaluminum compound. In an embodiment, the organoaluminum compound can be an alkylaluminum compound. In an embodiment, the alkylaluminum compound can be a trialkylaluminum, an alkylaluminum halide, an alkylaluminum alkoxide, or any combination thereof. In some embodiments, the alkylaluminum compound can be a trialkylaluminum, an alkylaluminum halide, or any combination thereof; alternatively, a trialkylaluminum, an alkylaluminum halide, or any combination thereof; or alternatively, a trialkylaluminum. In other embodiments, the alkylaluminum compound can be a trialkylaluminum; alternatively, an alkylaluminum halide; or alternatively, an alkylaluminum alkoxide. In yet other embodiments, the alkylaluminum compound which can be utilized as the scrub agent can be an aluminoxane (described herein and any of the general or specific aluminoxane can be utilized as the scrub agent. In a non-limiting embodiment, the trialkylaluminum compound can be, comprise, or consist essentially of, trimethylaluminum, triethylaluminum, tripropylaluminum, tributylaluminum, trihexylaluminum, trioctylaluminum, or mixtures thereof. In some non-limiting embodiments, the trialkylaluminum compound can be, comprise, or consist essentially of, trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting embodiments, the trialkylaluminum compound can be, comprise, or consist essentially of, trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum. In a non-limiting embodiment, the alkylaluminum halide can be, comprise, or consist essentially of, diethylaluminum chloride, diethylaluminum bromide, ethylaluminum dichloride, ethylaluminum sesquichloride, or mixtures thereof. In some non-limiting embodiments, the alkylaluminum halide can be, comprise, or consist essentially of, diethylaluminum chloride, ethylaluminum dichloride, ethylaluminum sesquichloride, or mixtures thereof. In other non-limiting embodiments, the alkylaluminum halide can be, comprise, or consist essentially of, diethylaluminum chloride; alternatively, diethylaluminum bromide; alternatively, ethylaluminum dichloride; or alternatively, ethylaluminum sesquichloride. In particular aspects of this invention, the organoaluminum compound can comprise trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, diisobutylaluminum hydride, diethylaluminum ethoxide, diethylaluminum chloride, or combinations thereof.

In an embodiment, the alkylaluminum compound which can be utilized as the scrub agent can be an aluminoxane. Aluminoxanes are independently disclosed herein (e.g., as a component of the catalyst system) and any of the general or specific aluminoxanes disclosed herein can be utilized without limitation as the scrub agent utilized in the processes, systems, and/or reaction systems disclosed herein.

The herein disclosed scrub agent(s) optionally can be indirectly introduced to the reaction zone 110 from a scrub agent source 170 via feed line 172. The scrub agent feed line 172, when present in system 100 or 200, is defined as having at least one scrub agent. While the scrub agent is shown in FIG. 1 and FIG. 2 as feeding into organic reaction medium feed line 162, it is contemplated the scrub agent alternatively can feed into any of line 142, line 152, line 191, line 192, and line 193.

Generally, the oligomer product that can be produced using the processes, systems, and/or reaction system described herein can be formed at conditions (or alternatively, the reaction zone can have any conditions) which can 1) facilitate oligomer product formation, 2) provide a desired oligomer product formation rate, 3) provide acceptable catalyst system productivity, 4) provide acceptable oligomer selectivity, and/or 5) provide acceptable polymer formation. In an embodiment, conditions under which the oligomer product can be formed (or alternatively, the reaction zone can have conditions) that can include one or more of catalyst system component ratios, chromium concentration, pressure, ethylene partial pressure, ethylene concentration, presence of hydrogen (and its partial pressure and/or hydrogen to ethylene weight ratio), temperature, reaction time, single pass ethylene conversion, and catalyst system productivity. Catalyst system component ratios, chromium concentration, pressure, ethylene partial pressure, ethylene concentration, presence of hydrogen (and its partial pressure and/or hydrogen to ethylene weight ratio), temperature, reaction time, single pass ethylene conversion, and catalyst system productivity are independently described herein and these independent descriptions can be used without limitation, and in any combination, to describe the process and/or reaction zone conditions at which the oligomer product can be formed for any of the processes, systems, and/or reaction systems described herein.

In an embodiment, the oligomer product can be formed (or the reaction zone can operate) at a minimum aluminum of the aluminoxane to chromium of the chromium component (e.g., $N^2$-phosphinyl formamidine chromium compound complex, the $N^2$-phosphinyl amidine chromium compound complex, and/or the $N^2$-phosphinyl guanidine chromium compound complex) molar ratio (i.e., minimum Al to Cr molar ratio) of 10:1, 50:1, 75:1, or 100:1; alternatively or additionally, at a maximum aluminum of the aluminoxane to chromium of the chromium component (e.g., $N^2$-phosphinyl formamidine chromium compound complex, the $N^2$-phosphinyl amidine chromium compound complex, and/or the $N^2$-phosphinyl guanidine chromium compound complex) molar ratio (i.e., maximum Al to Cr molar ratio) of 5,000:1, 3,000:1, 2,000:1, 1,500:1, or 1,000:1. In an embodiment, the oligomer product can be formed (or the reaction zone can operate) at an Al to Cr molar ratio ranging from any minimum Al to Cr molar ratio disclosed herein to any maximum Al to Cr molar ratio disclosed herein. In a non-limiting embodiment, the Al to Cr molar ratio can range from 10:1 to 5,000:1, from 50:1 to 3,000:1, from 50:1 to 3,000:1, from 75:1 to 2,000:1, from 100:1 to 2,000:1, of from 100:1 to 1,000:1. Other Al to Cr molar ratio ranges that can be utilized are readily apparent to those skilled in the art with the aid of this disclosure.

In an embodiment, the oligomer product can be formed (or the reaction zone can operate) at a minimum reaction zone chromium concentration of the chromium component (e.g., $N^2$-phosphinyl formamidine chromium compound complex, the $N^2$-phosphinyl amidine chromium compound complex, and/or the $N^2$-phosphinyl guanidine chromium compound complex) concentration (i.e., minimum chromium concentration) of $1 \times 10^{-6}$ Cr equivalents/liter, $1 \times 10^{-5}$ Cr equivalents/liter, or $5 \times 10^{-4}$ Cr equivalents/liter; alternatively or additionally, at a maximum reaction zone chromium concentration of the chromium component (e.g., $N^2$-phosphinyl formamidine chromium compound complex, the $N^2$-phosphinyl amidine chromium compound complex, and/or the $N^2$-phosphinyl guanidine chromium compound complex) concentration (i.e., maximum chromium concentration) of 1 Cr equivalents/liter, $5 \times 10^{-1}$ Cr equivalents/liter, or $1 \times 10^{-1}$ Cr equivalents/liter. In an embodiment, the oligomer product can be formed (or the reaction zone can operate) at a reaction zone chromium concentration ranging from any minimum chromium concentration disclosed herein to any maximum chromium concentration disclosed herein. In a non-limiting embodiment, the reaction zone chromium concentration can range from $1 \times 10^{-6}$ Cr equivalents/liter to 1 Cr equivalents/liter, from $1 \times 10^{-5}$ Cr equivalents/liter to $5 \times 10^{-1}$ Cr equivalents/liter, from $5 \times 10^{-4}$ Cr equivalents/liter to $1 \times 10^{-1}$ Cr equivalents/liter. Other chromium concentration ranges that can be utilized are readily apparent to those skilled in the art with the aid of this disclosure.

In an embodiment, the oligomer product can be formed (or the reaction zone can operate) at a minimum pressure of 5 psi (34.5 kPa), 50 psi (345 kPa); 100 psi (689 kPa), 150 psi (1.03 MPa), 250 psi (1.72 MPa), 500 psi (3.5 MPa), or 600 psi (4.1 MPa); alternatively of additionally, at a maximum pressure of 2,500 psi (17.2 MPa), 2,000 psi (13.8 MPa), 1,500 psi (10.3 MPa), 1400 psi (9.65 MPa), 1250 psi (8.62 MPa), or 1000 psi (6.89 MPa). In an embodiment, the oligomer product can be formed (or the reaction zone can operate) at a pressure ranging from any minimum pressure disclosed herein to any maximum pressure disclosed herein. In some non-limiting embodiments, the oligomer product can be formed (or the reaction zone can operate) at a pressure from 5 psi (34.5 kPa) to 2,500 psi (17.2 MPa), from 5 psi (34.5 kPa) to 2,000 psi (13.8 MPa), from 50 psi (345 kPa) to 2,000 psi (13.8 MPa), from 100 psi (689 kPa) to 2,000 psi (13.8 MPa), from 100 psi (689 kPa) to 1,500 psi (10.3 MPa), from 500 psi (3.5 MPa) to 1500 psi (10.3 MPa), from 150 psi (1.03 MPa) to 1250 psi (8.62 MPa), from 250 psi (1.72 MPa) to 1000 psig (6.89 MPa), or from 600 psi (4.1 MPa) to 1400 psi (9.65 MPa). Other pressure ranges that can be utilized are readily apparent to those skilled in the art with the aid of this disclosure.

In an embodiment, the oligomer product can be formed (or the reaction zone can operate) at a minimum ethylene partial pressure of 5 psi (34.5 kPa), 50 psi (345 kPa); 100 psi (689 kPa), 150 psi (1.03 MPa), 250 psi (1.72 MPa), or 500 psi (3.5 MPa); alternatively or additionally, at a maximum ethylene partial pressure of 2,500 psi (17.2 MPa), 2,000 psi (13.8 MPa), 1,500 psi (10.3 MPa), 1250 psi (8.62 MPa), or 1000 psi (6.89 MPa). In an embodiment, the oligomer product can be formed (or the reaction zone can operate) at an ethylene partial pressure ranging from any minimum ethylene partial pressure disclosed herein to any maximum ethylene partial pressure disclosed herein. In some non-limiting embodiments, the oligomer product can be formed (or the reaction zone can operate) at an ethylene partial pressure from 5 psi (34.5 kPa) to 2,500 psi (17.2 MPa), from 5 psi (34.5 kPa) to 2,000 psi (13.8 MPa), from 50 psi (345 kPa) to 2,000 psi (13.8 MPa), from 100 psi (689 kPa) to 2,000 psi (13.8 MPa), from 100 psi (689 kPa) to 1,500 psi (10.3 MPa), from 500 psi (3.5 MPa) to 1500 psi (10.3 MPa), from 150 psi (1.03 MPa) to 1250 psi (8.62 MPa), from 150 psi (1.03 MPa) to 1250 psi (8.62 MPa), or from 250 psi (1.72 MPa) to 1000 psi (6.89 MPa). Other ethylene partial pressure ranges are readily apparent to those skilled in the art with the aid of this disclosure.

In an embodiment, the oligomer product can be formed (or the reaction zone can operate) at a minimum ethylene concentration of 4 mass %, 10 mass %, 25 mass %, 35 mass %, or 40 mass % based upon the total mass in the reaction zone; alternatively or additionally, at a maximum ethylene concentration of 70 mass %, 65 mass %, 60 mass %, 55 mass %, 50 mass %, 48 mass % based upon the total mass in the reaction zone. In an embodiment, the oligomer product can be formed (or the reaction zone can operate) at an ethylene concentration ranging from any minimum ethylene concentration disclosed herein to any maximum ethylene concentration disclosed herein. In some non-limiting embodiments, the oligomer product can be formed (or the reaction zone can operate) at an ethylene concentration from 4 mass % to 70 mass %, from 4 mass % to 60 mass %, from 10 mass % to 60 mass %, from 25 mass % to 55 mass %, 35 mass % to 50 mass %, or 40 mass % to 48 mass % based upon the total mass in the reaction zone. Other ethylene concentration ranges that can be utilized are readily apparent to those skilled in the art with the aid of this disclosure.

In an embodiment, the oligomer product can be formed (or the reaction zone can operate) at a minimum ethylene:chromium mass ratio of 50,000:1, 150,000:1, 250,000:1, or 400,000:1; alternatively, or additionally, at a maximum ethylene:chromium mass ratio of 5,000,000:1, 2,500,000:1, 1,500,000:1, or 1,000,000:1. In an embodiment, the oligomer product can be formed (or the reaction zone can operate) at an ethylene:chromium mass ratio ranging from any minimum ethylene:chromium mass ratio disclosed herein to any maximum ethylene:chromium mass ratio disclosed herein. In some non-limiting embodiments, the oligomer product can be formed (or the reaction zone can operate) at an ethylene:chromium mass ratio from 50,000:1 to 5,000,000:1, 150,000:1 to 2,500,000:1, 250,000:1 to 1,500,000:1, or 400,000:1 to 1,000,000:1. Other ethylene: chromium mass ratio ranges that can be utilized are readily apparent to those skilled in the art with the aid of this disclosure.

In an embodiment wherein hydrogen is utilized, the oligomer product can be formed (or the reaction zone can operate) at a minimum hydrogen partial pressure of 1 psi (6.9 kPa), 2 psi (14 kPa); 5 psi (34 kPa), 10 psi (69 kPa), or 15 psi (103 kPa); alternatively or additionally at a maximum hydrogen partial pressure of 200 psi (1.4 MPa), 150 psi (1.03 MPa), 100 psi (689 kPa), 75 psig (517 kPa), or 50 psi (345 kPa). In an embodiment, the oligomer product can be formed (or the reaction zone can operate) at a hydrogen partial pressure ranging from any minimum hydrogen partial pressure disclosed herein to any maximum hydrogen partial pressure disclosed herein. In some non-limiting embodiments wherein hydrogen is utilized, the oligomer product can be formed (or the reaction zone can operate) at a hydrogen partial pressure from 1 psi (6.9 kPa) to 200 psi (1.4 MPa), from 5 psi (34 kPa) to 150 psi (1.03 MPa), from 10 psi (69 kPa) to 100 psi (689 kPa), or from 15 psi (100 kPa) to 75 psig (517 kPa). Other hydrogen partial pressure ranges that can be utilized are readily apparent to those skilled in the art with the aid of this disclosure.

In an embodiment wherein hydrogen is utilized, the oligomer product can be formed (or the reaction zone can operate) at a minimum hydrogen to ethylene mass ratio of (0.05 g hydrogen)/(kg ethylene), (0.1 g hydrogen)/(kg ethylene), (0.25 g hydrogen)/(kg ethylene), (0.4 g hydrogen)/(kg ethylene), or (0.5 g hydrogen)/(kg ethylene); alternatively or additionally, at a maximum hydrogen to ethylene mass ratio can be (5 g hydrogen)/(kg ethylene), (3 g hydrogen)/(kg ethylene), (2.5 g hydrogen)/(kg ethylene), (2 g hydrogen)/(kg ethylene), or (1.5 g hydrogen)/(kg ethylene). In an embodiment, the oligomer product can be formed (or the reaction zone can operate) at a hydrogen to ethylene mass ratio ranging from any minimum hydrogen to ethylene mass ratio disclosed herein to any maximum hydrogen to ethylene mass ratio disclosed herein. In some non-limiting embodiments, the oligomer product can be formed (or the reaction zone can operate) at a hydrogen to ethylene mass ratio from (0.05 g hydrogen)/(kg ethylene) to (5 g hydrogen)/(kg ethylene), from (0.25 g hydrogen)/(kg ethylene) to (5 g hydrogen)/(kg ethylene), from (0.25 g hydrogen)/(kg ethylene) to (4 g hydrogen)/(kg ethylene), from (0.4 g hydrogen)/(kg ethylene) to (3 g hydrogen)/(kg ethylene), from (0.4 g hydrogen)/(kg ethylene) to (2.5 g hydrogen)/(kg ethylene), from (0.4 g hydrogen)/(kg ethylene) to (2 g hydrogen)/(kg ethylene), or from (0.5 g hydrogen)/(kg ethylene) to (2 g hydrogen)/(kg ethylene). Other hydrogen to ethylene mass ratio ranges that can be utilized are readily apparent to those skilled in the art with the aid of this disclosure.

In an embodiment, the oligomer product can be formed (or the reaction zone can operate) at a minimum hydrogen:chromium mass ratio of 1:1, 50:1, 100:1, or 200:1; alternatively or additionally, at a maximum hydrogen:chromium mass ratio of 100,000:1, 50,000:1, 10,000:1, or 3,000:1. In an embodiment, the oligomer product can be formed (or the reaction zone can operate) at a hydrogen:chromium mass ratio ranging from any minimum hydrogen:chromium mass ratio disclosed herein to any maximum hydrogen:chromium mass ratio disclosed herein. In some non-limiting embodiments, the oligomer product can be formed (or the reaction zone can operate) at a hydrogen:chromium mass ratio from 1:1 to 100,000:1, 50:1 to 50,000:1, 100:1 to 10,000:1, or 200:1 to 3,000:1. Other hydrogen:chromium mass ratio ranges that can be utilized are readily apparent to those skilled in the art with the aid of this disclosure.

In an embodiment, the oligomer product can be formed (or the reaction zone can operate) at a minimum temperature of 0° C., 25° C., 40° C., or 50° C.; alternatively, or additionally, at a maximum temperature of 200° C., 150° C., 100° C., or 90° C. In an embodiment, the oligomer product can be formed (or the reaction zone can operate) at a temperature ranging from any minimum temperature disclosed herein to any maximum temperature disclosed herein. In some non-limiting embodiments, the oligomer product can be formed (or the reaction zone can operate) at a temperature from 0° C. to 200° C., from 25° C. to 150° C., from 40° C. to 100° C., from 50° C. to 100° C., or from 50° C. to 90° C. Other temperature ranges that can be utilized are readily apparent to those skilled in the art with the aid of this disclosure.

The reaction time (or residence time), for example, in the reaction zone can comprise any time that can produce the desired quantity of oligomer product; alternatively, any reaction time (or residence time) that can provide a desired catalyst system productivity; alternatively, any reaction time (or residence time) that can provide a desired ethylene conversion. Relating to forming the oligomer product, the oligomer product can be formed over a period of time (or an average time) that can produce the desired quantity of olefin product or polymer product, provide a desired catalyst system productivity, and/or provide a desired conversion of monomer. In some embodiments, the time can range from 1 minute to 5 hours; alternatively, ranges from 5 minutes to 2.5 hours; alternatively, ranges from 10 minutes to 2 hours; or alternatively, ranges from 15 minutes to 1.5 hours. In some embodiments (in continuous process embodiments), the reaction time (or residence time) can be stated as an average reaction time (or average residence time) and can range from 1 minute to 5 hours; alternatively, ranges from 5 minutes to 2.5 hours; alternatively, ranges from 10 minutes to 2 hours; or alternatively, ranges from 15 minutes to 1.5 hours.

In an embodiment, the processes, systems, and/or reaction systems described herein can have an ethylene conversion of at least 30%, 35%, 40%, or 45%.

In an embodiment, the processes, systems, and/or reaction systems (e.g., reaction systems 100 or 200) described herein can have a catalyst system productivity of greater than 10,000, 50,000, 100,000, 150,000, 200,000, 300,000, or 400,000 grams ($C_6+C_8$) per gram of chromium. In some embodiments (but not all embodiments), the processes, systems, and/or reaction systems (e.g., reaction systems 100 or 200) described herein can have a productivity higher than a productivity in an otherwise similar process which does not contact ethylene with the at least a portion of the organic reaction medium prior to contact of ethylene with the catalyst system; alternatively, does not introduce or feed the ethylene feedstock mixture into the reaction zone separately from the catalyst system; or alternatively, productivity greater than a productivity in an otherwise similar process which does not: i) contact ethylene with the at least a portion of the organic reaction medium prior to contact of ethylene with the catalyst system, and/or ii) introduce or feed the ethylene feedstock mixture into the reaction zone separately from the catalyst system. In an embodiment (but not all embodiments), the productivity can be increased by at least 5%, 7.5%, 10%, or 12.5%.

In some aspects and/or embodiments (but not necessarily all aspects and/or embodiments), the processes, systems, and/or reaction systems (e.g., reaction systems 100 or 200) described herein can produce less polymer per gram of oligomer product than an otherwise similar process which does not contact ethylene with the at least a portion of the organic reaction medium prior to contact of ethylene with the catalyst system; alternatively, does not introduce or feed the ethylene feedstock mixture into the reaction zone separately from the catalyst system; or alternatively, produces less polymer per gram of oligomer product than an otherwise similar process which does not: i) contact ethylene with the at least a portion of the organic reaction medium prior to contact of ethylene with the catalyst system, and/or ii) introduce or feed the ethylene feedstock mixture into the reaction zone separately from the catalyst system. In an embodiment (but not all embodiments), the mass of polymer per mass of oligomer in the reaction zone can be decreased by at least 10%, 25%, 40%, 50%, 60%, 70%, or 80%.

Depending upon the catalyst system utilized, the processes, systems, and/or reaction systems described herein can be an ethylene oligomerization process, system, and/or reaction system, an ethylene trimerization process, system, or reaction system, an ethylene tetramerization process, system, or reaction system or an ethylene trimerization and tetramerization process system, or reaction system; alternatively, an ethylene oligomerization process system, or reaction system; alternatively, an ethylene trimerization process, system, or reaction system; alternatively, an ethylene tetramerization process, system, or reaction system; or alternatively an ethylene trimerization and tetramerization process, system, or reaction system. In an ethylene trimerization embodiment, the oligomer product can comprise at least 70 wt. % hexenes, at least 75 wt. % hexenes, at least 80 wt. % hexenes, at least 85 wt. % hexenes, or at least 90 wt. % hexene based upon the weight of the oligomer product. In some ethylene trimerization embodiments, the oligomer product can comprise from 70 wt. % to 99.8 wt. % hexenes, from 75 wt. % to 99.7 wt. % hexenes, or from 80 wt. % to 99.6 wt. % hexenes based upon the weight of the oligomer product. In an ethylene tetramerization embodiment, the oligomer product can comprise at least 70 wt. % octene, at least 75 wt. % octene, at least 80 wt. % octenes, at least 85 wt. % octenes, or at least 90 wt. % octenes based upon the weight of the oligomer product. In some ethylene tetramerization embodiments, the oligomer product can comprise from 70 wt. % to 99.8 wt. % octenes, from 75 wt. % to 99.7 wt. % octenes, or from 80 wt. % to 99.6 wt. % octenes based upon the weight of the oligomer product. In an ethylene trimerization and tetramerization embodiment, the oligomer product can comprise at least 70 wt. % hexenes and octenes, at least 75 wt. % hexenes and octenes, at least 80 wt. % hexenes and octenes, at least 85 wt. % hexene and octene, or at least 90 wt. % hexenes and octenes based upon the weight of the oligomer product. In some ethylene trimerization and tetramerization embodiments, the oligomer product can comprise from 70 wt. % to 99.8 wt. % hexenes and octenes, from 75 wt. % to 99.7 wt. % hexenes and octenes, or from 80 wt. % to 99.6 wt. % hexenes and octenes based upon the weight of the oligomer product.

In ethylene oligomerization, ethylene trimerization, or ethylene trimerization and tetramerization embodiments, the ethylene trimer can comprise at least 85 wt. % 1-hexene; alternatively, at least 87.5 wt. % 1-hexene; alternatively, at least 90 wt. % 1-hexene; alternatively, at least 92.5 wt. % 1-hexene; alternatively, at least 95 wt. % 1-hexene; alternatively, at least 97 wt. % 1-hexene; or alternatively, at least 98 wt. % 1-hexene by weight of the ethylene trimer, or from 85 wt. % to 99.9 wt. % 1-hexene; alternatively, from 87.5 wt. % to 99.9 wt. % 1-hexene; alternatively, from 90 wt. % to 99.9 wt. % 1-hexene; alternatively, from 92.5 wt. % to 99.9 wt. % 1-hexene; alternatively, from 95 wt. % to 99.9 wt. % 1-hexene; alternatively, from 97 wt. % to 99.9 wt. % 1-hexene; or alternatively, from 98 wt. % to 99.9 wt. % 1-hexene by weight of the ethylene trimer.

In ethylene oligomerization, ethylene tetramerization, or ethylene trimerization and tetramerization embodiments, the ethylene tetramer can comprise at least 85 wt. % 1-octene; alternatively, at least 87.5 wt. % 1-octene; alternatively, at least 90 wt. % 1-octene; alternatively, at least 92.5 wt. % 1-octene; alternatively, at least 95 wt. % 1-octene; alternatively, at least 97 wt. % 1-octene; or alternatively at least 98 wt. % 1-octene by weight of the ethylene tetramer or from 85 wt. % to 99.9 wt. % 1-octene; alternatively, from 87.5 wt. % to 99.9 wt. % 1-octene; alternatively, from 90 wt. % to 99.9 wt. % 1-octene; alternatively, from 92.5 wt. % to 99.9 wt. % 1-octene; alternatively, from 95 wt. % to 99.9 wt. % 1-octene; alternatively, from 97 wt. % to 99.9 wt. % 1-octene; or alternatively, from 98 wt. % to 99.9 wt. % 1-octene by weight of the ethylene tetramer.

The processes, systems, and/or reaction systems (e.g., reaction systems 100 and/or 200) described herein can provide various advantages. Without being limited to theory, it is believed that one source of polymer formation can result when high concentrations of ethylene contact the catalyst system. One advantage that can be realized by the processes, systems, and/or reaction systems (e.g., reaction systems 100 and/or 200) described herein is that the mass of polymer (e.g., polyethylene in contrast to desired oligomers of ethylene) per mass of oligomer in the reaction zone (e.g., reaction zone 110 in systems 100 and/or 200) can be reduced (or alternatively can be less than a mass of polymer per mass of oligomer product formed) as compared to otherwise similar processes, systems and/or reaction systems (e.g., reaction systems of FIG. 3 and FIG. 4) which do not contact ethylene with at least a portion of the organic reaction medium prior to contact of ethylene with the catalyst systems disclosed herein. The mass of polymer per mass of oligomer in the reaction zone of the processes, systems, and/or reaction systems (e.g., reaction zone 110 in reaction systems 100 and 200) can be reduced (or alternatively, can be less than a mass of polymer per mass of oligomer product) as compared to otherwise similar processes, systems, and/or reaction systems (e.g., reaction systems of FIG. 3 and FIG. 4) which do not introduce or feed the ethylene feedstock mixture to the reaction zone separately from the chromium component of the catalyst systems disclosed herein.

Additionally, as is seen in the examples below, the productivity of the processes, systems, and/or reaction systems (e.g., reaction systems 100 and 200) implemented therein is higher than other similar processes, systems, and/or reaction systems (e.g., reaction systems of FIG. 3 and FIG. 4) which do not contact ethylene with at least a portion of the organic reaction medium prior to contact of ethylene with the catalyst systems disclosed herein. For example, the productivity of the processes, systems, and/or reaction systems (e.g., reaction systems 100 and 200) implemented therein can be greater than other similar processes, systems, and/or reaction systems which do not introduce or feed the ethylene feedstock mixture to the reaction zone (reaction zone 110) separately from the catalyst systems disclosed herein. Productivity is defined as the mass of liquid oligomer product (or alternatively, $C_6$ product, $C_8$ product, or ($C_6+C_8$) product) formed per mass of chromium or aluminum.

The herein disclosed processes, systems, and/or reaction systems also can provide improved commercial applicability for the use of catalysts systems in ethylene oligomerization. While not wishing to be bound by theory, it is believed that longer operating times are possible because the disclosed processes, systems, and reaction systems can reduce the amount of polymer in the reaction zone during oligomerization, thus reducing the levels of problematic fouling and plugging which can occur in the reaction system components.

Further, as is seen in the examples below, the disclosed processes, systems, and/or reaction systems provide improved ethylene utilization as indicated by improved ethylene conversion and higher $C_6$ purity in the oligomer product.

EXAMPLES

The subject matter having been generally described, the following examples are given as particular aspects of the disclosure and to demonstrate the practice and advantages thereof. It is understood that the examples are given by way of illustration and are not intended to limit the specification of the claims to follow in any manner.

In an inert atmosphere drybox, a catalyst system was prepared by adding 25 mg of Complex A to a 40 mL vial containing a magnetic stir bar. Complex A was then dissolved in 5 mL of ethylbenzene and stirred on a magnetic stir plate until visual observation indicated complete Complex A dissolution. To this solution, 18.5 mL of 7 wt. % MMAO-3A in heptane was added to the vial and stirred to assure complete mixing. A charge vessel was prepared with 68 mL of methylcyclohexane and a portion of MMAO-3A to act as quench for any contaminants in the methylcyclohexane. The Complex A solution was then added to the charger and the charger was then shaken, sealed, and removed from the drybox. The contents of the charger were then charged to the catalyst system source 150 of the reaction system to provide the catalyst system for Example 1, Example 2, and Example 3.

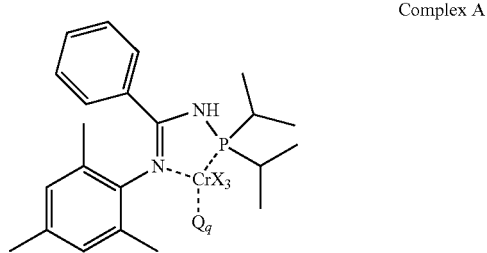

Complex A

Examples 1-3 used the desired steady state ethylene oligomerization conditions and operating parameters provided in Table 3.

TABLE 3

| Desired Steady State Operating Parameters | |
|---|---|
| Temperature (° C.) | 70 |
| Pressure (psig; MPag) | 750; 5.17 |
| Organic Reaction Medium | Cyclohexane |
| Organic Reaction Medium Feed Rate (g/h) | 500 |
| Ethylene Feed Rate (g/h) | 400 |
| Hydrogen Feed Rate (sccm) | 40 |
| Catalyst System Solution Feed Rate (mL/h) | 12.5 |
| Al:Cr Molar Ratio | 812:1 |
| Residence Time (minutes) | 15-25 |

In Table 1 and the other tables included herein, use of "g" refers to grams, "h" refers to hours, "mL" refers to milliliters, "min" refers to minutes, "sccm" refers to standard cubic centimeters per minute, "MPag" refers to megapascals gauge, and "psig" refers to pounds per square inch gauge.

Example 1

Comparative

Example 1 (comparative) used a reaction system having the feed line configurations shown in FIG. 3 with an autoclave reactor as the reaction zone 110. In this example, the ethylene feed line 142 (comprising ethylene and hydrogen) is not diluted with the organic reaction medium and was fed directly to the reaction zone 110. Likewise, the catalyst system feed line 152 was fed to the reaction zone 110 without any combination with other streams or dilution.

Prior to run initiation, the reaction zone 110 was treated with a pretreatment solution composed of 5 mL neat triethylaluminum, 5 mL ethylbenzene, and 60 mL of methylcyclohexane. The reaction zone pretreatment was accomplished by charging reaction zone 110 with 20 mL of the pretreatment solution and heating reaction zone 110 to 70° C. The flow of the pretreatment solution from the scrub agent source 170 to the reaction zone 110 via line 172, line 162, and pump 180 was then adjusted to a flow rate of 20 mL/hour. The organic reaction medium (cyclohexane) flow was then initiated from organic reaction medium source 160 to reaction zone 110 via line 162, and pump 180. The organic reaction medium flow rate was adjusted to a flow rate of 500 g/hour. Then the hydrogen flow was initiated from the hydrogen source to the reaction zone 110 via lines 144 and 142. The pretreatment solution flowed through the reactor for 1 hour at 70° C.

The ethylene oligomerization was initiated by discontinuing the flow of the pretreatment solution and initiating the flow of catalyst system solution from catalyst system source 150 to reaction zone 110 via line 152 at the designated flow rate indicated in Table 3. Thirty minutes after the catalyst system flow to reaction zone 110 was initiated, ethylene flow was initiated from ethylene source 140 to reaction zone 100 via line 142 at a rate of 100 g/hour by opening valve 143. At initiation of ethylene flow to reaction zone 110, the catalyst feed line 152 plugged and no run data was obtained.

Example 2

Comparative

Example 2 (comparative) used a reaction system having the configuration shown in FIG. 4 with an autoclave reactor as the reaction zone 110. The catalyst system feed line 152 is shown in FIG. 4 as combining with the organic reaction medium feed line 162 on the suction side 181 of the pump 180. Thus, in comparison with Example 1, Example 2 diluted the catalyst system with organic reaction medium prior to introduction to the reaction zone 110.

Prior to run initiation, the reaction zone 110 was treated with pretreatment solution composed of 5 mL neat triethylaluminum, 5 mL ethylbenzene, and 60 mL of methylcyclohexane. The reaction zone pretreatment was accomplished by charging reaction zone 110 with 20 mL of the pretreatment solution and heating reaction zone 110 to 70° C. The flow of the pretreatment solution from the scrub agent source 170 to the reaction zone 110 via line 172, line 162, pump 180, and line 163 was then adjusted to a flow rate of 20 mL/hour. The organic reaction medium (cyclohexane) flow was then initiated from organic reaction medium source 160 to reaction zone 110 via line 162, pump 180, and line 163. The organic reaction medium flow rate was then adjusted to a flow rate of 500 g/hour. Then the hydrogen flow was initiated from the hydrogen source to the reaction zone 110 via lines 144 and 142. The pretreatment solution flowed through the reactor for 1 hour at 70° C.

The ethylene oligomerization was initiated by discontinuing the flow of the pretreatment solution and initiating the flow of catalyst system solution from catalyst system source 150 to reaction zone 110 via line 152, line 163, and pump 180 at the designated flow rate indicated in Table 3. Thirty minutes after the catalyst system flow to reaction zone 110 was initiated, ethylene flow was initiated from ethylene source 140 to reaction zone 100 via line 142 at a rate of 100 g/hour by opening valve 143. The ethylene flow rate was then gradually increased from 100 g/hour to 400 g/hour over a period of 2 hours. As the ethylene flow rate was increased, the reaction zone 110 temperature increased and the temperature of the reaction zone 110 was regulated with heat exchanger 120 via lines 122 and 124. Samples of the reaction zone effluent were taken every 30 minutes. Upon initiation of ethylene flow, heavy solids were observed in the reaction zone effluent samples and the reactor pressure increased rapidly and would not decrease, suggesting that a plug in the reaction effluent line 118 had occurred. The ethylene oligomerization run was then terminated prior to achieving the maximum ethylene feed rate. Upon disassembling the autoclave reactor, massive plugging was observed in the reaction zone inlets 111, 113 and reaction zone outlet 117. Solids recovered from the reactor had a mass of 19.7416 g.

Run data and conditions are shown in Table 4 for a selection of the samples from Example 2.

aluminum, 5 mL ethylbenzene, and 60 mL of methylcyclohexane. The reaction zone pretreatment was accomplished by charging reaction zone 110 with 20 mL of the pretreatment solution and heating reaction zone 110 to 70° C. The flow of the pretreatment solution from the scrub agent source 170 to the reaction zone 110 via line 172, line 162, pump 180, line 191, mixing device 190 (which was a static mixer), and line 192 was then adjusted to a flow rate of 20 mL/hour. The organic reaction medium (cyclohexane) flow was then initiated from organic reaction medium source 160 to reaction zone 110 via line 162, pump 180, line 191, mixing device 190, and line 192 and was adjusted to a flow rate of 500 g/hour. Then the hydrogen flow was initiated from the hydrogen source to the reaction zone 110 via line 144, line 142, line 191, mixing device 190, and line 192. The pretreatment solution flowed through the reactor for 1 hour at 70° C.

The ethylene oligomerization was initiated by discontinuing the flow of the pretreatment solution and initiating the flow of catalyst system solution from catalyst system source 150 to reaction zone 110 via line 152 at the designated flow rate indicated in Table 3. Thirty minutes after the catalyst system flow to reaction zone 110 was initiated, ethylene flow

TABLE 4

| | Example 2 Sample # | | | | | |
|---|---|---|---|---|---|---|
| | 1 | 3 | 5 | 7 | 9 | 11 |
| Reaction Zone Run Parameters | | | | | | |
| Run Time (min) | 30 | 90 | 150 | 210 | 270 | 330 |
| Catalyst System Flow Rate (mL/h) | 12.5 | 12.5 | 12.5 | 12.5 | 12.5 | 12.5 |
| Organic Reaction Medium Flow Rate (g/h) | 500 | 340 | 450 | 600 | 512 | 500 |
| Ethylene Flow Rate (g/h) | 115 | 170 | 210 | 258 | 320 | 340 |
| Hydrogen Flow Rate (g/h) | 0.188 | 0.180 | 0.187 | 0.183 | 0.180 | 0.180 |
| $H_2$ to $C_2^=$ Mass Ratio (g $H_2$/kg $C_2^=$) | 1.64 | 1.06 | 0.89 | 0.71 | 0.56 | 0.53 |
| Reactor Temp. (° C.) | 71.4 | 72.3 | 72.6 | 74.1 | 75.9 | 78.8 |
| Reactor Coolant Input Temp. (° C.) | 77.6 | 61.7 | 58.7 | 52.3 | 44.4 | 34.9 |
| Residence Time (min) | 34.1 | 41.1 | 31.8 | 24.4 | 25.2 | 25.0 |
| Calc. Reactor [Cr] (PPM by mass) | 0.45 | 0.54 | 0.42 | 0.32 | 0.33 | 0.33 |
| Calc. Reactor [Al] (PPM by mass) | 189 | 228 | 176 | 135 | 140 | 139 |
| Al:Cr Molar Ratio | 812 | 812 | 812 | 812 | 812 | 812 |
| Oligomer Product | | | | | | |
| Total Liquid Product Production (g) | 4.5 | 73.9 | 267 | 532 | 879 | 1295 |
| Total ($C_6 + C_8$) Production (g) | 4 | 72 | 256 | 503 | 827 | 1212 |
| $C_6$ in liquid oligomer product, wt. % | 88.95 | 96.54 | 94.45 | 93.32 | 93.32 | 92.57 |
| $C_6$ Purity (wt. % 1-hexene) | 97.01 | 99.29 | 98.90 | 98.97 | 99.06 | 99.35 |
| $C_8$ in liquid oligomer product, wt. % | 2.53 | 1.57 | 1.01 | 0.80 | 0.69 | 0.64 |
| $C_8$ Purity (wt. % 1-octene) | 99.99 | 98.19 | 97.05 | 96.01 | 96.33 | 97.41 |
| $C_{10}$ in liquid oligomer product, wt. % | 8.51 | 1.88 | 4.54 | 5.89 | 5.98 | 6.80 |
| Reaction Zone Efficiencies | | | | | | |
| ($C_6 + C_8$) Productivity g ($C_6 + C_8$)/g Cr | 10,363 | 151,368 | 326,583 | 400,831 | 504,066 | 615,800 |
| ($C_6 + C_8$) Productivity g ($C_6 + C_8$)/g Al | 25 | 359 | 775 | 951 | 1,196 | 1,462 |
| g Total Liquid Product/g Cat | 1,168 | 14,183 | 32,587 | 41,093 | 51,682 | 63,857 |
| g Total Liquid Product/g Al | 31 | 379 | 870 | 1,097 | 1,380 | 1,705 |
| % Ethylene Conversion | 3.9 | 28.8 | 53.3 | 54.6 | 55.3 | 64.3 |
| % Ethylene Conversion to ($C_6 + C_8$) | 3.5 | 28.1 | 50.3 | 50.9 | 51.5 | 59.6 |
| Reactor Efficiency (lb $C_6$/gal/h) | 0.1 | 0.8 | 1.8 | 2.2 | 2.8 | 3.4 |

Example 3

Example 3 used a reaction system having the configuration shown in FIG. 1 with an autoclave reactor as the reaction zone 110. As discussed in detail herein, the catalyst system feed line 142 in FIG. 1 is fed directly to the reaction zone 110 in FIG. 1, and ethylene is combined with the organic reaction medium feed line 162 to yield the ethylene feedstock mixture in line 191.

Prior to run initiation, the reaction zone 110 was treated with pretreatment solution composed of 5 mL neat triethylwas initiated from ethylene source 140 to reaction zone 100 via line 144, line 142, line 191, mixing device 190, and line 192 at a rate of 100 g/hour by opening valve 143. The ethylene flow rate was then gradually increased from 100 g/hour to 400 g/hour over a period of 2 hours. As the ethylene flow rate was increased, the reaction zone temperature increased and the temperature was regulated with heat exchanger 120 via line 122 and 124. Samples of the reaction zone effluent were taken every 30 minutes. The reaction zone effluent samples were remarkably clearer than the samples obtained in Example 2. By the time a 200 g/h of ethylene feed rate was achieved, very little polymer was observed in the samples. Eventually, the maximum ethylene feed rate of 400 g/h was achieved. The run of Example 3 was terminated after about 10 hours due to the expenditure of the catalyst system solution and not due to plugging or fouling of the reactor components.

After opening the reactor, a thin layer of polyethylene covering every surface of the reactor was observed. No major build-up on any of the reactor components was observed. Solids recovered from the reactor were 4.8889 g.

Run data and conditions are shown in Tables 5-A and 5-B for a selection of the samples from Example 3.

TABLE 5-A

| | Sample # | | | | |
|---|---|---|---|---|---|
| | 1 | 3 | 5 | 7 | 9 |
| Reaction Zone Run Parameters | | | | | |
| Run Time (min) | 30 | 90 | 150 | 210 | 270 |
| Catalyst System Flow Rate (mL/h) | 12.5 | 12.5 | 12.5 | 12.5 | 12.5 |
| Organic Reaction Medium Flow Rate (g/h) | 450 | 450 | 590 | 450 | 550 |
| Ethylene Flow Rate (g/h) | 100 | 160 | 240 | 290 | 365 |
| Hydrogen Flow Rate (g/h) | 0.185 | 0.183 | 0.175 | 0.186 | 0.171 |
| $H_2$ to $C_2^=$ Mass Ratio (g $H_2$/kg $C_2^=$) | 1.85 | 1.14 | 0.73 | 0.64 | 0.47 |
| Reactor Temp. (° C.) | 71.8 | 71.5 | 71.7 | 71.8 | 71.9 |
| Reactor Coolant Input Temp. (° C.) | 74.9 | 68.4 | 62.6 | 59.0 | 54.2 |
| Residence Time (min) | 38.1 | 34.4 | 25.3 | 28.3 | 22.9 |
| Calc. Reactor [Cr] (PPM by mass) | 0.50 | 0.45 | 0.33 | 0.37 | 0.30 |
| Calc. Reactor [Al] (PPM by mass) | 211.03 | 190.31 | 139.93 | 156.92 | 126.94 |
| Al:Cr Molar Ratio | 812 | 812 | 812 | 812 | 812 |
| Oligomer Product | | | | | |
| Total Liquid Product Production | 19.8 | 192 | 451 | 801 | 1232 |
| Total ($C_6 + C_8$) Production (g) | 19 | 181 | 420 | 740 | 1138 |
| $C_6$ in liquid oligomer product, wt. % | 97.04 | 93.62 | 92.58 | 92.15 | 92.60 |
| $C_6$ Purity (wt. % 1-hexene) | 99.58 | 98.84 | 98.64 | 98.71 | 98.89 |
| $C_8$ in liquid oligomer product, wt. % | 1.82 | 0.46 | 0.42 | 0.49 | 0.63 |
| $C_8$ Purity (wt. % 1-octene) | 100.00 | 94.11 | 94.38 | 95.02 | 97.72 |
| $C_{10}$ in liquid oligomer product, wt. % | 1.14% | 5.92 | 6.99 | 7.36 | 6.77 |
| Reaction Zone Efficiencies | | | | | |
| ($C_6 + C_8$) Productivity g ($C_6 + C_8$)/g Cr | 61,257 | 285,811 | 386,475 | 503,824 | 627,290 |
| ($C_6 + C_8$) Productivity g ($C_6 + C_8$)/g Al | 145 | 678 | 917 | 1,196 | 1,489 |
| g Total Liquid Product/g Cat | 5,618 | 29,394 | 40,836 | 53,578 | 65,614 |
| g Total Liquid Product/g Al | 150 | 785 | 1,090 | 1,431 | 1,752 |
| % Ethylene Conversion | 19.8 | 63.1 | 58.4 | 63.3 | 61.6 |
| % Ethylene Conversion to ($C_6 + C_8$) | 19.5 | 58.7 | 53.5 | 57.9 | 56.7 |
| Reactor Efficiency (lb $C_6$/gal/h) | 0.3 | 1.6 | 2.1 | 2.8 | 3.5 |

TABLE 5-B

| | Sample # | | | | |
|---|---|---|---|---|---|
| | 11 | 13 | 15 | 17 | 19 |
| Reaction Zone Run Parameters | | | | | |
| Run Time (min) | 330 | 390 | 450 | 510 | 570 |
| Catalyst System Flow Rate (mL/h) | 12.5 | 12.5 | 12.5 | 12.5 | 12.5 |
| Organic Reaction Medium Flow Rate (g/h) | 560 | 560 | 460 | 652 | 690 |
| Ethylene Flow Rate (g/h) | 385 | 400 | 400 | 401 | 402 |
| Hydrogen Flow Rate (g/h) | 0.172 | 0.178 | 0.180 | 0.190 | 0.179 |
| $H_2$ to $C_2^=$ Mass Ratio (g $H_2$/kg $C_2^=$) | 0.45 | 0.45 | 0.45 | 0.47 | 0.44 |
| Reactor Temp. (° C.) | 72.2 | 72.6 | 73.1 | 74.0 | 75.1 |
| Reactor Coolant Input Temp. (° C.) | 56.6 | 51.3 | 49.9 | 43.5 | 40.5 |
| Residence Time (min) | 22.2 | 21.9 | 24.4 | 19.9 | 19.2 |
| Calc. Reactor [Cr] (PPM by mass) | 0.29 | 0.29 | 0.32 | 0.26 | 0.25 |
| Calc. Reactor [Al] (PPM by mass) | 122.92 | 121.00 | 135.05 | 110.32 | 106.39 |
| Al:Cr Molar Ratio | 812 | 812 | 812 | 812 | 812 |
| Oligomer Product | | | | | |
| Total Liquid Product Production (g) | 1727 | 2212 | 2699 | 3185 | 3671 |
| Total ($C_6 + C_8$) Production (g) | 1598 | 2055 | 2516 | 2973 | 3429 |
| $C_6$ in liquid oligomer product, wt. % | 93.02 | 94.21 | 94.21 | 93.29 | 92.86 |
| $C_6$ Purity (wt. % 1-hexene) | 99.16 | 99.12 | 99.57 | 99.25 | 99.64 |

TABLE 5-B-continued

| | Sample # | | | | |
|---|---|---|---|---|---|
| | 11 | 13 | 15 | 17 | 19 |
| $C_8$ in liquid oligomer product, wt. % | 0.79 | 0.97 | 1.08 | 1.04 | 0.94 |
| $C_8$ Purity (wt. % 1-octene) | 98.25 | 98.76 | 98.92 | 98.84 | 98.66 |
| $C_{10}$ in liquid oligomer product, wt. % | 6.19 | 4.81 | 4.71 | 5.67 | 6.20 |
| Reaction Zone Efficiencies | | | | | |
| $(C_6 + C_8)$ Productivity g $(C_6 + C_8)$/g Cr | 716,604 | 675,271 | 728,197 | 695,254 | 706,148 |
| $(C_6 + C_8)$ Productivity g $(C_6 + C_8)$/g Al | 1,701 | 1,603 | 1,728 | 1,650 | 1,676 |
| g Total Liquid Product/g Cat | 73,630 | 67,447 | 71,922 | 70,507 | 71,878 |
| g Total Liquid Product/g Al | 1,966 | 1,801 | 1,920 | 1,883 | 1,919 |
| % Ethylene Conversion | 65.5 | 57.7 | 61.6 | 60.2 | 61.2 |
| % Ethylene Conversion to $(C_6 + C_8)$ | 60.9 | 54.5 | 58.4 | 56.4 | 57.2 |
| Reactor Efficiency (lb $C_6$/gal/h) | 3.9 | 3.6 | 3.9 | 3.8 | 3.8 |

Table 6 below summarizes calculations obtained for comparative Example 2 and Example 3.

TABLE 6

| | Example 2 (comparative) | Example 3 |
|---|---|---|
| Max Productivity (g NAO/g Cr) | 615,800 | 737,606 |
| Max Productivity (g NAO/g Al) | 1,462 | 1,751 |
| $(C_6 + C_8)$ Selectivity (%) | 92.4 | 93.2 |
| $C_6$ Purity (%) | 98.9 | 99.2 |
| $C_8$ Purity (%) | 97.4 | 97.2 |
| Ethylene Conversion (%) | 44.4 | 58.9 |
| Cr Concentration (ppm by mass) | 0.4 | 0.3 |
| Al Concentration (ppm by mass) | 168 | 127 |

As can be seen in Table 6, Example 3 achieved a higher maximum productivity than Example 2 (on both a Cr basis and an Al basis). It can also be seen in Table 6, Example 3 also provided improved $(C_6+C_8)$ selectivity, $C_6$ purity, $C_8$ purity, $C_2H_4$ conversion, Cr concentration, and Al concentration as compared to the process, system, and/or reaction system where ethylene and the organic reaction system were not contacted prior to ethylene contacting the catalyst system as performed in Example 2.

Figure 5:
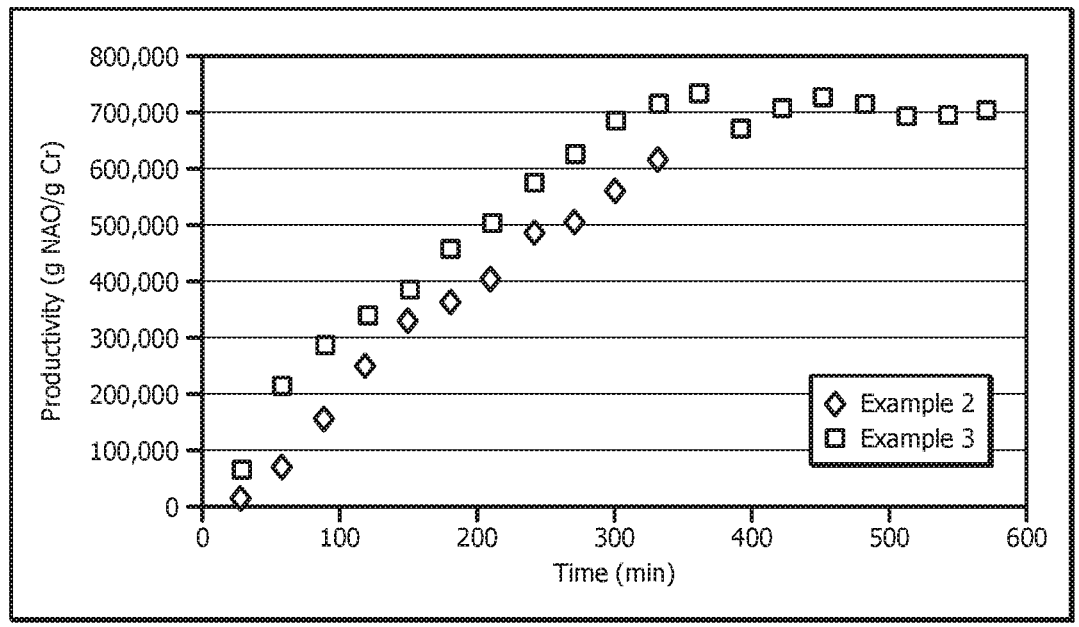
FIG. 5 shows a graph of productivity versus time for Example 2 and Example 3.

FIG. 5 shows the productivity of Example 2 and Example 3 over time. The productivity of Example 3 at any given point in time was over 100 g NAO/g Cr higher than Example 2. Also shown in FIG. 5, without ethylene dilution before contact with the catalyst system in Example 2, the maximum ethylene feed rate (400 g/h) was not achieved because the oligomerization reaction was stopped due to fouling/plugging with polyethylene. Thus, while productivity increased over time for Example 2, overall production was impeded due to reactor shutdown because of plugging/fouling. In contrast, the productivity of Example 3 increased over time until the maximum ethylene feed rate (400 g/h) was reached, at which point the productivity remained relativity constant until the reactor was shut down at about 600 minutes according to end-of-day shutdown procedures (the reactor was not shut down because of fouling/plugging).

Figure 6:
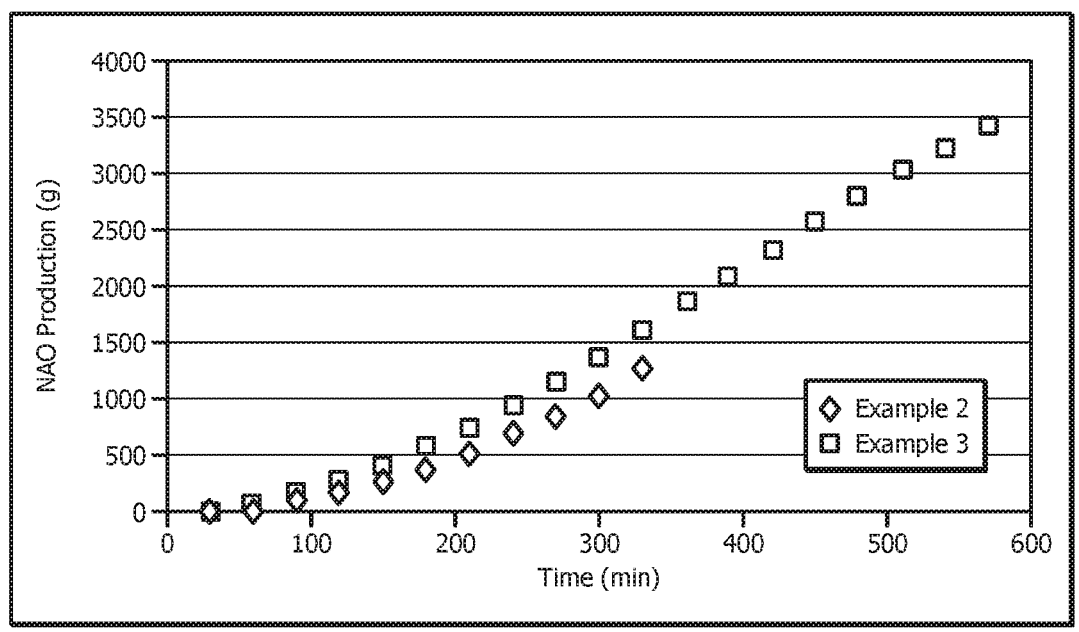
FIG. 6 shows a graph of normal alpha olefin (NAO) production versus time for Example 2 and Example 3.

FIG. 6 shows the normal alpha olefin (NAO) production over time for both Example 2 and Example 3. As can be seen, the NAO production for Example 3 was greater than the NAO production for Example 2 at any point in time. Moreover, the overall NAO production of Example 3 was greater than Example 2, since the run Example 2 terminated early due to fouling. The run of Example 3 could have continued NAO production past 600 minutes and was only terminated due to end-of-day shutdown procedures.

Table 7 below shows solids production data for Example 2 and Example 3.

TABLE 7

| | Example 2 (comparative) | Example 3 |
|---|---|---|
| Isolated Polyethylene (g) | 19.7416 | 4.8889 |
| Wt. % of Normal Alpha Olefin (%) | 1.63 | 0.14 |
| Solids Ratio (g Polyethylene/kg Normal Alpha Olefin) | 16.3 | 1.43 |

The isolated polyethylene is the amount of solids recovered from the reactor. Surprisingly, roughly four times the amount of polyethylene solids was recovered in Example 2 as compared to the amount of polyethylene solids recovered in Example 3. Relative to the amount of normal alpha olefin produced, Example 2 has an order of magnitude higher level of solids ratio than Example 3, which is surprising and unexpected.

In summary, the surprising and unexpected results observed in Example 3 over Example 2 include:

i) a four-times reduction in polymer recovered from the reactor in Example 3 versus the polymer recovered from the reactor in Example 2;

ii) improved catalyst system productivity;

iii) an order of magnitude reduction in the solids to oligomer product ratio when comparing Example 3 with Example 2;

iv) the oligomerization reaction in Example 3 was only terminated due to end of day;

v) the amount of solids observed in the samples of Example 3 decreased over time; and vi) the selectivity and $C_6$ purity improved for Example 3 as compared to Example 2.

While Example 3 utilized the configuration of reaction system 100 shown in FIG. 1, it is expected that the configuration of reaction system 200 in FIG. 2 would perform similarly (and processes and/or systems using the same contact means) because an ethylene feedstock mixture is formed prior to contact of ethylene with the catalyst system, even though the contact in FIG. 2 is outside the reaction zone 110. Thus, it is expected that system 200 (and processes and/or systems using the same contact means) would have the same surprising and unexpected results as reaction system 100.

ADDITIONAL DISCLOSURE

Accordingly, the scope of protection is not limited by the description set out above but is only limited by the claims which follow, that scope including all equivalents of the subject matter of the claims. Each and every claim is incorporated into the specification as an aspect of the present invention. Thus, the claims are a further description and are an addition to the detailed description of the present invention. The disclosures of all patents, patent applications, and publications cited herein are hereby incorporated by reference.

Embodiment 1

A process comprising: contacting 1) ethylene, 2) a catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane, 3) an organic reaction medium, and optionally 4) hydrogen; and forming an oligomer product in a reaction zone; wherein the ethylene is contacted with at least a portion of the organic reaction medium to form an ethylene feedstock mixture prior to contacting ethylene with the catalyst system.

Embodiment 2

A process of embodiment 1, wherein the ethylene and the organic reaction medium are dispersed in the ethylene feedstock mixture prior to contact of the ethylene feedstock mixture with the catalyst system.

Embodiment 3

The process of embodiment 1 or 2, wherein the catalyst system and the ethylene feedstock mixture are contacted prior to entering the reaction zone.

Embodiment 4

The process of embodiment 1 or 2, wherein the catalyst system is introduced into the reaction zone separately from the ethylene feedstock mixture.

Embodiment 5

The process of any one of embodiments 1-4, wherein substantially all of the ethylene is introduced to the reaction zone via the ethylene feedstock mixture.

Embodiment 6

A process comprising: introducing a catalyst system to a reaction zone, the catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane; introducing an ethylene feedstock mixture to the reaction zone separately from the catalyst system, the ethylene feedstock mixture comprising ethylene and at least a portion of an organic reaction medium used in the process, wherein the ethylene feedstock mixture is substantially free of the catalyst system; optionally introducing hydrogen to the reaction zone; and contacting the catalyst system and the ethylene feedstock mixture in the reaction zone to form an oligomer product.

Embodiment 7

A process comprising: feeding a catalyst system mixture to a reaction zone, the catalyst system mixture comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane; separately feeding to the reaction zone an ethylene feedstock mixture comprising ethylene and at least a portion of an organic reaction medium, wherein the ethylene feedstock mixture is substantially free of the catalyst system; contacting the catalyst system mixture and the ethylene feedstock mixture in the reaction zone; and forming an oligomer product in the reaction zone.

Embodiment 8

A process comprising: contacting in a reaction zone 1) ethylene, 2) a catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane, 3) an organic reaction medium, and 4) optionally hydrogen to form an oligomer product; wherein: the catalyst system is fed to the reaction zone, an ethylene feedstock mixture comprising the ethylene and at least a portion of the organic reaction medium is fed separately from the catalyst system to the reaction zone, and the ethylene feedstock mixture is substantially free of the catalyst system.

Embodiment 9

A process comprising: a) diluting an ethylene feed stream by addition of at least a portion of an organic reaction medium to the ethylene feed stream prior to contact of the ethylene feed stream with a catalyst system in a reaction zone; (b) contacting in the reaction zone the diluted ethylene feed stream with the catalyst system, wherein the catalyst system comprises i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane; and c) forming an oligomer product in the reaction zone.

Embodiment 10

A process comprising: a) contacting ethylene and at least a portion of an organic reaction medium to form an ethylene feedstock mixture; b) subsequent to a), contacting in a reaction zone the ethylene feedstock mixture with a catalyst system mixture comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane; and c) forming an oligomer product in the reaction zone.

Embodiment 11

A system comprising: a feedstock mixture comprising a mixture of ethylene and an organic reaction medium; a catalyst stream comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane; and a reaction zone receiving the feed stream separately from the catalyst stream, wherein ethylene is dispersed with the organic reaction medium to form the mixture prior to introduction of the mixture into the reaction zone via the feed stream.

Embodiment 12

The subject matter of any one of embodiments 1-11, wherein the at least a portion of the organic reaction medium is contacted with a scrub agent (e.g., an alkylaluminum compound) prior to introduction of the at least a portion of the organic reaction medium to the reaction zone.

Embodiment 13

The subject matter of any one of embodiments 1-12, wherein the at least a portion of the organic reaction medium is contacted with a scrub agent (e.g., an alkylaluminum compound) prior to contact of ethylene with the at least a portion of the organic reaction medium.

Embodiments 14

The subject matter of any one of embodiments 1-13, wherein the ethylene feedstock mixture is contacted with a scrub agent (e.g., an alkylaluminum compound) prior to introduction of the ethylene feedstock mixture to the reaction zone.

Embodiments 15

The subject matter of any one of embodiments 1-14, wherein the catalyst system is dispersed in a diluent prior to contacting ethylene.

Embodiment 16

The subject matter of any one of embodiments 1-5, wherein the diluent comprises the organic reaction medium.

Embodiment 17

The subject matter of any one of embodiments 1-6, wherein the oligomer product is formed at a temperature in a range of 0° C. to 200° C.

Embodiment 18

The subject matter of any one of embodiments 1-17, wherein the oligomer product is formed at an ethylene partial pressure in a range of 50,000:1 to 5,000,000:1.

Embodiment 19

The subject matter of any one of embodiments 1-18, wherein the oligomer product is formed at a temperature in a range of 50° C. to 100° C., an ethylene:chromium mass ratio from 250,000:1 to 1,500,000:1, and a hydrogen:chromium mass ratio from 100:1 to 10,000:1 based upon the total mass in the reaction zone.

Embodiment 20

The subject matter of any one of embodiments 1-19, wherein the oligomer product comprises hexenes and/or octenes; or alternatively, comprises (a) at least 70 wt. % hexenes, (b) at least 70 wt. % octenes, or (c) a total of at least 70 wt. % hexenes and octenes.

Embodiment 21

The subject matter of any one of embodiments 1-20, wherein a reaction zone effluent comprising the oligomer product is removed from the reaction zone.

Embodiments 22

The subject matter of embodiment 21, wherein hexenes and/or or octenes are separated from the reaction zone effluent.

Embodiment 23

The subject matter of embodiment 21 or 22, wherein the ethylene feedstock mixture, the catalyst system, and optionally, hydrogen are periodically or continuously introduced into the reaction zone and a reaction zone effluent comprising the oligomer product is periodically or continuously removed from the reaction zone.

Embodiment 24

The subject matter of any one of embodiments 1-23, wherein a mass of polymer per mass of oligomer in the reaction zone is less than a mass of polymer per mass of oligomer in the reaction zone of an otherwise similar process which does not: i) contact ethylene with the at least a portion of the organic reaction medium prior to contact of ethylene with the catalyst system, and/or ii) introduce or feed the ethylene feedstock mixture into the reaction zone separately from the catalyst system.

Embodiment 25

The subject matter of any one of embodiments 1-23, having a productivity greater than a productivity in an otherwise similar process which does not: i) contact ethylene with the at least a portion of the organic reaction medium prior to contact of ethylene with the catalyst system, and/or ii) introduce or feed the ethylene feedstock mixture into the reaction zone separately from the catalyst system.

Embodiment 26

A reaction system comprising: a reaction zone; a first reaction zone inlet configured to introduce a catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane to the reaction zone; a second reaction zone inlet configured to introduce an ethylene feedstock mixture comprising ethylene and an organic reaction medium to the reaction zone, wherein the ethylene feedstock mixture is substantially free of the catalyst system; and one or more reaction zone outlets configured to discharge a reaction zone effluent comprising an oligomer product from the reaction zone.

Embodiment 27

The reaction system of embodiment 26, further comprising: a catalyst system feed line flowing the catalyst system to the first reaction zone inlet; an ethylene feed line comprising the ethylene; and an organic reaction medium feed line comprising the organic reaction medium; wherein the organic reaction medium feed line and the ethylene feed line combine to yield the ethylene feedstock mixture which is introduced to the second reaction zone inlet.

Embodiment 28

The reaction system of embodiment 26 or 27, further comprising: a pump in fluid communication with the second reaction zone inlet located upstream of a point where the ethylene feed line and the organic reaction medium feed line join to produce the ethylene feedstock mixture.

Embodiment 29

The reaction system of any one of embodiments 26-28, further comprising: a mixing device positioned between i) the joining of the ethylene feed line and the organic reaction medium feed line, and ii) the second reaction zone inlet, to disperse the ethylene and the organic reaction medium in the ethylene feedstock mixture prior to the ethylene feedstock mixture entering the reaction zone.

Embodiment 30

The reaction system of embodiment 29, wherein the mixing device is a static mixer.

Embodiment 31

The reaction system of any one of embodiments 26-30, wherein the first reaction zone inlet is configured to periodically or continuously introduce the catalyst system to the reaction zone, the second reaction zone inlet is configured to periodically or continuously introduced the ethylene feedstock mixture to the reaction zone, and the one or more reaction zone outlets is configured to periodically or continuously discharge the reaction zone effluent comprising the oligomer product from the reaction zone.

Embodiment 32

The reaction system of any one of embodiments 26-31, wherein the reaction zone is one or more reactors selected from a stirred tank reactor, a plug flow reactor, and any combination thereof; or alternatively, an autoclave reactor, a continuous stirred tank reactor, a loop reactor, a gas phase reactor, a solution reactor, a tubular reactor, a recycle reactor, a bubble reactor, and any combination thereof.

Embodiment 33

A reaction system comprising: a reaction zone having a reaction zone inlet; an ethylene feed line in fluid communication with the reaction zone inlet and comprising ethylene; an organic reaction medium feed line in fluid communication with the reaction zone inlet and comprising an organic reaction medium, wherein the ethylene feed line and the organic reaction medium feed line join to produce an ethylene feedstock mixture prior to the reaction zone inlet; a catalyst system feed line in fluid communication with the reaction zone inlet and comprising a catalyst system and which combines with the ethylene feedstock mixture to yield a combined feed line, wherein the combined feed line flows to the reaction zone via the reaction zone inlet; a reaction zone outlet configured to discharge a reaction zone effluent comprising an oligomer product from the reaction zone; wherein the catalyst system comprises i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane.

Embodiment 34

The reaction system of embodiment 33, further comprising: a pump in fluid communication with the reaction zone inlet and which is located upstream of a point where the ethylene feed line and the organic reaction medium feed line join to produce the ethylene feedstock mixture.

Embodiment 35

The reaction system of embodiment 33 or 34, further comprising: a mixing device positioned between i) the joining of the ethylene feed line and the organic reaction medium feed line and ii) the reaction zone inlet to disperse the ethylene and the organic reaction medium in the ethylene feedstock mixture prior to the ethylene feedstock mixture joining with the catalyst system and entering the reaction zone.

Embodiment 36

The reaction system of embodiment 35, wherein the mixing device is a static mixer.

Embodiment 37

The reaction system of any one of embodiments 33-36, wherein the reaction zone inlet is configured to periodically or continuously introduce the combined feed line to the reaction zone, and the reaction zone outlet is configured to periodically or continuously discharge the reaction zone effluent from the reaction zone.

Embodiment 38

The reaction system of any one of embodiments 33-37, wherein the reaction zone is one or more reactors selected from autoclave reactor, a continuous stirred tank reactor, a loop reactor, a gas phase reactor, a solution reactor, a tubular reactor, a recycle reactor, a bubble reactor, or a combination thereof.

The invention illustratively disclosed herein suitably can be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above can vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

All publications and patents mentioned herein are incorporated herein by reference. The publications and patents mentioned herein can be utilized for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Therefore, the present invention is well adapted to attain the ends and advantages mentioned as well as those that are inherent therein. This concludes the detailed description. The particular embodiments disclosed above are illustrative only, as the invention can be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above can be altered or modified and all such variations are considered within the scope and spirit of the invention. Accordingly, the protection sought herein is as set forth in the claims herein.

What is claimed is:

1. A process comprising:
contacting 1) ethylene, 2) a catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane, 3) an organic reaction medium, and optionally 4) hydrogen to form an oligomer product in a reaction zone,
wherein the ethylene is contacted with at least a portion of the organic reaction medium to form an ethylene feedstock mixture prior to contacting ethylene with the catalyst system,
wherein the catalyst system is introduced into the reaction zone separately from the ethylene feedstock mixture, wherein:
A) a mass of polymer per mass of oligomer in the reaction zone is less than a mass of polymer per mass of oligomer in the reaction zone of an otherwise similar process which does not: it contact ethylene with the at least a portion of the organic reaction medium prior to contact of ethylene with the catalyst system, and ii) introduce or feed the ethylene feedstock mixture into the reaction zone separately from the catalyst system,
or
B) the process has a productivity greater than a productivity in an otherwise similar process which does not: i) contact ethylene with the at least portion of the organic reaction medium prior to contact of ethylene with the catalyst system, and ii) introduce or feed the ethylene feedstock mixture into the reaction zone separately from the catalyst system.

2. The process of claim 1, wherein the ethylene and the organic reaction medium are dispersed in the ethylene feedstock mixture prior to contact of the ethylene feedstock mixture with the catalyst system.

3. The process of claim 2, wherein the ethylene and the organic reaction medium are dispersed in a mixing device.

4. The process of claim 3, wherein the mixing device comprises a static mixer, an impeller, or a propeller.

5. The process of claim 1, wherein the oligomer product comprises hexenes and/or octenes.

6. The process of claim 1, wherein the ethylene feedstock mixture, the catalyst system, and optionally, hydrogen are periodically or continuously introduced into the reaction zone and a reaction zone effluent comprising the oligomer product is periodically or continuously removed from the reaction zone.

7. The process of claim 1, wherein the reaction zone comprises one or more reactors selected from an autoclave reactor, a continuous stirred tank reactor, a loop reactor, a gas phase reactor, a solution reactor, a tubular reactor, a recycle reactor, a bubble reactor, or any combination thereof.

8. The process of claim 1, the mass of polymer per mass of oligomer in the reaction zone is decreased by at least 10% relative to the otherwise similar process which does not: i) contact ethylene with the at least a portion of the organic reaction medium prior to contact of ethylene with the catalyst system, and/or ii) introduce or feed the ethylene feedstock mixture into the reaction zone separately from the catalyst system.

9. The process of claim 1, wherein the organic reaction medium is selected from aliphatic hydrocarbons.

10. The process of claim 1, further comprising:
contacting the organic reaction medium with a scrub agent prior to contacting the at least a portion of the organic reaction medium with ethylene.

11. The process of claim 10, further comprising:
contacting hydrogen with the ethylene prior to contacting the ethylene with the at least a portion of the organic reaction medium.

12. The process of claim 1, further comprising:
contacting hydrogen with the ethylene prior to contacting the ethylene with the at least a portion of the organic reaction medium.

13. A process comprising:
introducing a catalyst system to a reaction zone, the catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane;
introducing an ethylene feedstock mixture to the reaction zone separately from the catalyst system, the ethylene feedstock mixture comprising ethylene and at least a portion of an organic reaction medium, wherein the ethylene feedstock mixture is substantially free of the catalyst system;
optionally introducing hydrogen to the reaction zone; and
contacting the catalyst system and the ethylene feedstock mixture in the reaction zone to form an oligomer product,
wherein:
A) a mass of polymer per mass of oligomer in the reaction zone is less than a mass of polymer per mass of oligomer in the reaction zone of an otherwise similar process which does not: i) contact ethylene with the at least a portion of the organic reaction medium prior to contact of ethylene with the catalyst system, and ii) introduce or feed the ethylene feedstock mixture into the reaction zone separately from the catalyst system, or B) the process has a productivity greater than a productivity in an otherwise similar process which does not: i) contact ethylene with the at lea a portion of the organic reaction medium prior to contact of ethylene with the catalyst system, and ii) introduce or feed the ethylene feedstock mixture into the reaction zone separately from the catalyst system.

14. The process claim 13, wherein the oligomer product comprises hexenes and/or octenes.

15. The process of claim 13, wherein the ethylene feedstock mixture, the catalyst system, and optionally, hydrogen are periodically or continuously introduced into the reaction zone and a reaction zone effluent comprising the oligomer product is periodically or continuously removed from the reaction zone.

16. The process of claim 13, wherein the reaction zone comprises one or more reactors selected from an autoclave reactor, a continuous stirred tank reactor, a loop reactor, a gas phase reactor, a solution reactor, a tubular reactor, a recycle reactor, a bubble reactor, or any combination thereof.

17. The process of claim 13, the mass of polymer per mass of oligomer in the reaction zone is decreased by at least 10% relative to the otherwise similar process which does not: i) contact ethylene with the at least a portion of the organic reaction medium prior to contact of ethylene with the catalyst system, and/or ii) introduce or feed the ethylene feedstock mixture into the reaction zone separately from the catalyst system.

* * * * *